US006861254B1

(12) United States Patent
Rosenberg et al.

(10) Patent No.: US 6,861,254 B1
(45) Date of Patent: Mar. 1, 2005

(54) HEPARAN SULFATE D-GLUCOSAMINYL 3-O-SULFOTRANSFERASES, AND USES THEREFOR

(75) Inventors: Robert D. Rosenberg, Boston, MA (US); Nicholas W. Shworak, Westwood, MA (US); Jian Liu, Chapel Hill, NC (US); Linda M. S. Fritze, Sharon, MA (US); John J. Schwartz, Newtonville, MA (US); Lijuan Zhang, Winthrop, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/557,262

(22) Filed: Apr. 24, 2000

Related U.S. Application Data

(63) Continuation of application No. PCT/US98/22597, filed on Oct. 23, 1998.
(60) Provisional application No. 60/062,762, filed on Oct. 24, 1997, and provisional application No. 60/065,437, filed on Oct. 31, 1997.

(51) Int. Cl.$^7$ .......................... C12N 5/00; C12N 15/63; C07N 21/04
(52) U.S. Cl. ................... 435/325; 536/23.5; 435/320.1
(58) Field of Search .............................. 536/23.4, 23.5, 536/23.1; 435/325; 800/13, 15, 6, 17, 18

(56) References Cited

U.S. PATENT DOCUMENTS 5,650,550 A   7/1997   Korach et al. ................. 880/2

FOREIGN PATENT DOCUMENTS

| GB | 2295012 | 5/1996 |
| WO | WO 93/19096 | 9/1993 |
| WO | WO 93/25659 | 12/1993 |
| WO | WO 94/21689 | 9/1994 |
| WO | WO 96/13606 | 5/1996 |

OTHER PUBLICATIONS

Ko et al. Systematic analyses of mouse genes expressed in embryo implantation site pp. 3–4 1997.*
Ko et al. Systematic analyses of mouse genes expressed in embryo implantation site pp. 7–8 1997.*
JU Bowie et al., Science, "Deciphering the Message in Protein Sequences: Tolerance to Amino Acid Substitutions," Mar. 1990. vol. 247, pp. 1306–1310.*
F Gandolfi, Transgenic Research, "Spermatozoa, DNA binding and transgenic animals," 1998, 7:147–155.*
JT Ngo et al., Protein Folding Problem and Tertiary Structure Prediction," Computational Complexity, Protein Structure Prediction. and the Levinthal Paradox," 491–495.*
J Rudinger, Peptide Hormones, "Characteristics of the amino acids as components of a peptide hormone sequence," Jun. 1976, pp. 1–7.*

M Marra et al., Est Database Accession No. W62484, Jun. 1996.*
M Marra et al., Est Database Accession No. AA041885, Sep. 1996.*
P Philippsen et al., Sequence 906, Pat. No. 6,239,264.*
ER Cameron, Molecular Biotechnology, "Recent Advances in Transgenic Technology," 1997, vol. 7, pp. 253–265.
JJ Mullins et al., Hypertension, "Transgenesis in Nonmurine Species." vol. 22, No. 4, pp. 630–633.
RF Seamark, Reprod. Fertil.Dev.,"Progress and Emerging Problems in Livestock Transgenesis: a Summary Perspective," 1994, 6, pp. 653–657.
RL Gardner et al., Int.J.Dev.Biol., "Reflections on the biology of embryonic stem (ES) cells," 1997, 41:235–243.
McCormick. et al., (Jun. 1998) "The Putative Tumour Suppressor EXT1 Alters the Expression of Cell–Surface Heparan Sulfate," *Nature of Genetics*, vol. 19, pp. 158–161.
Fernandez C. J. and Warren G., (Jul. 24, 1998) "In Vitro Synthesis of Sulfated Glycosaminoglycans Coupled to Inter– compartmental Golgi Transport." *The Journal of Biological Chemistry*, vol. 273, No. 30, pp. 19030–19039.
Zhang, et al., (1998) "The Retinoic Acid and cAMP–dependent Up–regulation of 3–O–Sulfotransferase–1 Leads to a Dramatic Augmentation of Anticoagulantly Active Heparan Sulfate Biosynthesis in F9 Embryonal Carcinoma Cells." *The Journal of Biological Chemistry*, vol. 273.
DiGabriele, et al., (Jun. 1998) "Structure of a heparin–linked biologically active dimer of fibroblast growth factor." *Nature*, vol. 393, No. 6687, pp. 812–817.
Kjellén, I., and Lindahl, U., (1991) "Proteoglycans: Structures and Interactions." *Annual Review Biochemistry*, vol. 60, pp. 443–475.
Rosenberg, et al., (May 1997) "Heparan Sulfate Proteoglycans of the Cardiovascular System. Specific Structures Emerge But How is Synthesis Regulated?," *Journal for Clinical Investigation*. vol. 99, No. 9, pp. 2062–2070.
Shworak et al., (Oct. 1997) "Molecular Cloning and Expression of Mouse and Human cDNAs Encoding Heparan Sulfate D–Glycosaminul 3–O–Sulfotransferase," *The Journal of Biological Chemistry*, vol. 272, No. 44, pp. 28008–28019.

(List continued on next page.)

*Primary Examiner*—Ram R. Shukla
(74) *Attorney, Agent, or Firm*—Eitan, Pearl, Latzer & Cohen Zedek, LLP; Mark S. Cohen

(57) ABSTRACT

Disclosed are novel isolated nucleic acids and substantially pure protein preparations for naturally occurring and synthetic or chimeric heparan sulfate D-glicosaminyl 3-O-sulfo-transferases (3-OSTs). Also disclosed are uses for these genes and proteins, including uses for the modification and sequencing of glycosaminoglycans.

18 Claims, 3 Drawing Sheets

OTHER PUBLICATIONS

Shworak et al., (Oct. 25, 1996) "Cell–free Synthesis of Anticoagulant Heparan Sulfate Reveals a Limiting Converting Activity That Modifies an Excess Precursor Pool," *The Journal of Biological Chemistry*, vol. 271, No. 4, pp. 27063–27071.

Shworak et al., (Aug. 19, 1994) "Characterization of Ryudocan Glycosaminoglycan Acceptor Sites." *The Journal of Biological Chemistry*, vol. 269, No. 33, pp. 21204–21214.

Liu et al., (Oct. 25, 1996) "Purification of Heparan Sulfate D–Glucosaminyl 3–O–Sulfotransferase." *The Journal of Biological Chemistry*, vol. 271, No. 43, pp. 27072–27082.

EMEST19 Database, Accession No. AA041885, Sep. 05, 1996 (Rel. 49, Created) glycosaminoglycan N–acetylglucosaminyl N–deacetylase. Marra M. et al.

Shworak, et al., (Oct. 21, 1997) "Control of the Systhesis of Anticoagulant Heparan Sulfate: Molecular Cloning and Expression of the Rate Limiting Enzymes, 3—O—Sulfotransferase," *Meeting Info: 70th Scientific Sessions of the American Heart Association*, vol. 96, No. 8, pp. 1412.

EMEST18 Database, Accession No. AA407647, May 04, 1997 (Rel. 51, Created) Ko M.S.H. et al.

EMEST11 Datebase, Accession No. AA460705, Jun. 13, 1997 (Rel. 52. Created) Hillier L. et al.

Eriksson I et al. "cDNA cloning and sequencing of mouse mastocytoma glucosaminyl. N–deacetylase/N–sulfotransferase. an enzyme involved in the biosynthesis of heparin." J Biol. Chem., Apr. 8, 1994, 269 (14), P10438–43.

EMBL Database, Accession No. F07258, Feb. 15, 1995, Auffray C. et al.

EMBL Database, Accession No. W89350, Marra M. et al , Jul. 07, 1996, similar to glycosaminoglycan N–acetylglucosaminyl N–deacetylase.

EMBL Database, Accession No. N71828, Hillier et al., Mar. 20, 1996.

EMBL Datebase, Accession No. T75445, Hillier et al., Mar. 24, 1995, similar to glycosaminoglycan N–acetylglucosaminyl N–deacetylase.

EMBL Database, Accession No. F13088, Mar. 05, 1995, Genexpress.

International Search Report in PCT/US98/22597 (Annex to Form PCT/ISA/220) dated Jun. 30, 1999, (12 pages).

* cited by examiner

| | | | | | |
|---|---|---|---|---|---|
| m3-OST-1 | MTLLLLGAVL | LVAQPQLVHS | HPAAPGPGLK | QQELLRKVII | 40 |
| h3-OST-1 | MAALLLGAVL | LVAQPQLVPS | RPA----ELG | QQELLRKAGT | 36 |
| m3-OST-1 | LPEDTGEGTA | SNGSTQQLPQ | TIIIGVRKGG | TRALLEMLSL | 80 |
| h3-OST-1 | LQDDVRDGVA | PNGSAQQLPQ | TIIIGVRKGG | TRALLEMLSL | 76 |
| m3-OST-1 | HPDVAAAENE | VHFFDWEEHY | SQGLGWYLTQ | MPFSSPHQLT | 120 |
| h3-OST-1 | HPDVAAAENE | VHFFDWEEHY | SHGLGWYLSQ | MPFSWPHQLT | 116 |
| m3-OST-1 | VEKTPAYFTS | PKVPERIHSM | NPTIRLLLIL | RDPSERVLSD | 160 |
| h3-OST-1 | VEKTPAYFTS | PKVPERVYSM | NPSIRLLLIL | RDPSERVLSD | 156 |
| m3-OST-1 | YTQVLYNHLQ | KHKPYPPIED | LLMRDGRLNL | DYKALNRSLY | 200 |
| h3-OST-1 | YTQVFYNHMQ | KHKPYPSIEE | FLVRDGRLNV | DYKALNRSLY | 196 |
| m3-OST-1 | HAHMLNWLRF | FPLGHIHIVD | GDRLIRDPFP | EIQKVERFLK | 240 |
| h3-OST-1 | HVHMQNWLRF | FPLRHIHIVD | GDRLIRDPFP | EIQKVERFLK | 236 |
| m3-OST-1 | LSPQINASNF | YFNKTKGFYC | LRDSGKDRCL | HESKGRAHPQ | 280 |
| h3-OST-1 | LSPQINASNF | YFNKTKGFYC | LRDSGRDRCL | HESKGRAHPQ | 276 |
| m3-OST-1 | VDPKLLDKLH | EYFHEPNKKF | FKLVGRTFDW | H | 311 |
| h3-OST-1 | VDPKLLNKLH | EYFHEPNKKF | FELVGRTFDW | H | 307 |

Figure 1

```
599  KTCDRFPKLLIIGPQKTGTTALYLFLGMHPDLSSNYPSSETFEEIQFFN GHNYHKGIDWYMEFFPIPSNTTSDFYFEKS          NST-1
598  KTCDRLPKFLIVGPQKTGTTAIHFFLSLHPAVTSSFPSPSTFEEIQFFN SPNYHKGIDWYMDFFPVPSNASTDFLFEKS          NST-2
 23  TSKKRFPDAIIVGVKKSGTRALLEFLRVNPLI                  KAPGPEVHFFDKNFN  KGLEWYREQMPETKFGEV TIEKS  ce3-OST
193  GEKK LPQALIIGVKKGGTRALLEFLRVHPDV                  RAVGVEPHFFDRN    YEKGLEWYRNVMPKTLD GQITMEKT 3-OST-4
148  GS KQLPQAIIIGVKKGGTRALLEFLRVHPDV                  RAVGAEPHFFDRS    YDKGLAWYRDLMPRTLD GQITMEKT 3-OST-3A
110  GT KRLPQALIVGVKKGGTRAVLEFIRVHPDV                  RALGTEPHFFDRN    YGRGLDWYRSLMPRTLE SQITLEKT 3-OST-2
 49  GSAQQLPQTIIGVRKGGTRALLEMLSLHPDV                   AAAENEVHFFDWEEHYSHGLGWYLSQMPFSWP HQLTVEKT   3-OST-1

678  ANYFDSEVAPRRAAALLPKAKVLTILINPADRAYSWYQHQRAHDDPVALKYTFHEVITAGSDA                           NST-1
677  ATYFDSEVVPRRGAALLPRAKIITVLTNPADRAYSWYQHQRAHGDPVALNYTFYQVISASSQT                           NST-2
 93  PAYFHSKMAPERIKSLNPNTKIIIVVRDPVTRAISDYTQSSSKRKRVGLM PSFETMAVGNCANWLRTNCTTKTRGVNAG           ce3-OST
262  PSYFVTNEAPKRIHSMAKDIKLIVVVRNPVTRAISDYTQT           LSKKPEIPTFEVLAFKNRT                     3-OST-4
217  PSYFVTREAPARISAMSKDTKLIVVVRDPVTRAISDYTQT           LSKRPDIPTFESLTFKNRT                     3-OST-3A
179  PSYFVTQEAPRRIFNMSRDTKLIVVVRNPVTRAISDYTQT           LSKKPDIPTFEGLSFRNRT                     3-OST-2
121  PAYFTSPKVPERVYSMNPSIRLLLILRDPSERVLSDYTQVFYNHMQKHKPYPSIEEFLVRD        GRLNVD                3-OST-1

749  NRCLVPGWYATHIERWLSAYHANQILVLDGKLLRTEPAKVMDMVQKFLGVTNTIDYHKTLAFDPKKGFWC  QLLEGGKT           NST-1
748  NRCLVPGYYSTHLQRWLTYYPSGQLLIVDGQELRTNPAASMESIQKFLGITPFLNYTRTLRFDDDKGFWC  QGLEGGKT           NST-2
172  WGAIRIGVYHKHMKRWLDHFPIENIHIVDGEKLISNPADEISATEKFLGLKPVAK PEKFGVDPIKKFPCIK  NEDGKL           ce3-OST
328  WSAIRIGIYALHLENWLQYFPLSQILFVSGERLIVDPAGEMAKVQDFLGLKRVVT KKHFYENKTKGFPCLKKPEDSSAP           3-OST-4
283  WSAIQIGIYAKHLEHWLRHFPIRQMLFVSGERLISDPAGELGRVQDFLGLKRIIT DKHFYENKTKGFPCLKKAEGSSRP           3-OST-3A
245  WNAIRIGMYVLHLESWLQYFPLAQIHFVSGERLITDPAGEMGRVQDFLGIKRFIT DKHFYENKTKGFPCLKKTESSLLP           3-OST-2
188  YKALNRSLYHVHMQNWLRFFPLRHIHIVDGDRLIRDPFPEIQKVERFLKLSPQIN ASNFYENKTKGFYCLR     DSGRD         3-OST-1

827  KCLGKSKGRKYPEMDLDSRAFLKDYYRDHNIELSKLLYKMGQTLPTWLREDLQNTR           NST-1
826  RCLGRSKGRRYPDMDTESRLFLTDFFRNHNLELSKLLISRLGQPVPSWLREELQHSSLG        NST-2
249  HCLGKTKGRHHPDVEPSVLKTLREFYGPENKKFYQMINHWFDW                        ce3-OST
407  RCLGKSKGRTHPRIDPDVIHRLRKFYKPFNLMFYQMTGQDFQWEQEEGDK                 3-OST-4
362  HCLGKTKGRTHPEIDREVVRLREFYRPFNLKFYQMTGHDFGWDG                       3-OST-3A
324  RCLGKSKGRTHVQIDPEVIDQLREFYRPYNIKFYETVGQDFRWE                       3-OST-2
264  RCLHESKGRAHPQVDPKLLNKLHEYFHEPNKKFFELVGRTFDWH                       3-OST-1
```

Figure 2

SEQUENCE LISTING

```
<160> NUMBER OF SEQ ID NOS: 16

<210> SEQ ID NO 1
<211> LENGTH: 1685
<212> TYPE: DNA
<213> ORGANISM: Mus musculus
<220> FEATURE:
<221> NAME/KEY: CDS
<222> LOCATION: (323)..(1255)
<223> OTHER INFORMATION: mouse 3-OST-1

<400> SEQUENCE: 1
tgcattgcaa tgtgaagtgt tcctgaataa acctgcttga agaaggacaa cgtggtgttg      60
cgtctttcct gctggtcggg gtggaataga cacctcccct ttttaacttg ggtgacctca     120
tgaacataaa agaacttaaa ggtagcaagc catggactta aagtaggctg accttgaact     180
cagagatctt cttggcaatg tctctggaga ttaaagtaat tggcaactgg agatactcat     240
gttccagtaa tcaagaggga gccttgctgc tacttcatga tccaggcgcg tgtggcccag     300
tgaagtccct gagctgtaca gc atg acc ttg ctg ctc ctg ggt gcg gtg ctg     352
                         Met Thr Leu Leu Leu Leu Gly Ala Val Leu
                           1               5                  10 ctg gtg gcc cag ccc cag ctt gtg cat tcc cac ccg gct gct cct ggc     400
Leu Val Ala Gln Pro Gln Leu Val His Ser His Pro Ala Ala Pro Gly
                 15                  20                  25 ccg ggg ctc aaa cag cag gag ctt ctg agg aag gtg att att ctc cca     448
Pro Gly Leu Lys Gln Gln Glu Leu Leu Arg Lys Val Ile Ile Leu Pro
             30                  35                  40
```

-continued

| | |
|---|---|
| gag gac acc gga gaa ggc aca gca tcc aat ggt tcc aca cag cag ctg<br>Glu Asp Thr Gly Glu Gly Thr Ala Ser Asn Gly Ser Thr Gln Gln Leu<br>45 50 55 | 496 |
| cca cag acc atc atc att ggg gtg cgc aag ggt ggt acc cga gcc ctg<br>Pro Gln Thr Ile Ile Ile Gly Val Arg Lys Gly Gly Thr Arg Ala Leu<br>60 65 70 | 544 |
| cta gag atg ctc agc ctg cat cct gat gtt gct gca gct gaa aac gag<br>Leu Glu Met Leu Ser Leu His Pro Asp Val Ala Ala Ala Glu Asn Glu<br>75 80 85 90 | 592 |
| gtc cat ttc ttt gac tgg gag gag cat tac agc caa ggc ctg ggc tgg<br>Val His Phe Phe Asp Trp Glu Glu His Tyr Ser Gln Gly Leu Gly Trp<br>95 100 105 | 640 |
| tac ctc acc cag atg ccc ttc tcc tcc cct cac cag ctc acc gtg gag<br>Tyr Leu Thr Gln Met Pro Phe Ser Ser Pro His Gln Leu Thr Val Glu<br>110 115 120 | 688 |
| aag aca ccc gcc tat ttc act tcg ccc aaa gtg cct gag aga atc cac<br>Lys Thr Pro Ala Tyr Phe Thr Ser Pro Lys Val Pro Glu Arg Ile His<br>125 130 135 | 736 |
| agc atg aac ccc acc atc cgc ctg ctg ctt atc ctg agg gac cca tca<br>Ser Met Asn Pro Thr Ile Arg Leu Leu Leu Ile Leu Arg Asp Pro Ser<br>140 145 150 | 784 |
| gag cgc gtg ctg tcc gac tac acc cag gtg ttg tac aac cac ctt cag<br>Glu Arg Val Leu Ser Asp Tyr Thr Gln Val Leu Tyr Asn His Leu Gln<br>155 160 165 170 | 832 |
| aag cac aag ccc tat cca ccc att gag gac ctc cta atg cgg gac ggt<br>Lys His Lys Pro Tyr Pro Pro Ile Glu Asp Leu Leu Met Arg Asp Gly<br>175 180 185 | 880 |
| cgg ctg aac ctg gac tac aag gct ctc aac cgc agc ctg tac cat gca<br>Arg Leu Asn Leu Asp Tyr Lys Ala Leu Asn Arg Ser Leu Tyr His Ala<br>190 195 200 | 928 |
| cac atg ctg aac tgg ctg cgt ttt ttc ccg ttg ggc cac atc cac att<br>His Met Leu Asn Trp Leu Arg Phe Phe Pro Leu Gly His Ile His Ile<br>205 210 215 | 976 |
| gtg gat ggc gac cgc ctc atc aga gac cct ttc cct gag atc cag aag<br>Val Asp Gly Asp Arg Leu Ile Arg Asp Pro Phe Pro Glu Ile Gln Lys<br>220 225 230 | 1024 |
| gtc gaa aga ttc ctg aag ctt tct cca cag atc aac gcc tcg aac ttc<br>Val Glu Arg Phe Leu Lys Leu Ser Pro Gln Ile Asn Ala Ser Asn Phe<br>235 240 245 250 | 1072 |
| tac ttt aac aaa acc aag ggc ttc tac tgc ctg cgg gac agt ggc aag<br>Tyr Phe Asn Lys Thr Lys Gly Phe Tyr Cys Leu Arg Asp Ser Gly Lys<br>255 260 265 | 1120 |
| gac cgc tgc tta cac gag tcc aaa ggc cgg gcg cac ccc cag gtg gat<br>Asp Arg Cys Leu His Glu Ser Lys Gly Arg Ala His Pro Gln Val Asp<br>270 275 280 | 1168 |
| ccc aaa cta ctt gat aaa ctg cac gaa tac ttt cat gag cca aat aag<br>Pro Lys Leu Leu Asp Lys Leu His Glu Tyr Phe His Glu Pro Asn Lys<br>285 290 295 | 1216 |
| aaa ttt ttc aag ctc gtg ggc aga aca ttc gac tgg cac tgatttgccg<br>Lys Phe Phe Lys Leu Val Gly Arg Thr Phe Asp Trp His<br>300 305 310 | 1265 |
| tctcctaggc tcgggacttt tcctgttgtt aacttctggt gtacatctga aggggggagg | 1325 |
| aaaataattt taaaaaggca tttaagctat aatttatttg taaaacccac aaatgacttc | 1385 |
| tgtacagtat tagattcaca gttgccatat atagtagtta tattttttcta cttgttaaat | 1445 |
| ggagggcgtt ttgtattgtt tttcatggtt gttaacattg tgtatatgtc tctataatat | 1505 |
| gaaggaactt aactattgca ctgaaaaaat aagagatttt ttttttctgg agacctcttt | 1565 |

```
ttttgttgtt gttgtttttaa atataattaa cctgcctcca atccaaaata gctctttgtt    1625
ttcacctcct tgtcaaatct ataatctttt tctgcttaaa aaatttattg gtattatgga    1685
```

<210> SEQ ID NO 2
<211> LENGTH: 311
<212> TYPE: PRT
<213> ORGANISM: Mus musculus

<400> SEQUENCE: 2

```
Met Thr Leu Leu Leu Gly Ala Val Leu Val Ala Gln Pro Gln
 1               5                  10                  15

Leu Val His Ser His Pro Ala Ala Pro Gly Pro Gly Leu Lys Gln Gln
            20                  25                  30

Glu Leu Leu Arg Lys Val Ile Ile Leu Pro Glu Asp Thr Gly Glu Gly
        35                  40                  45

Thr Ala Ser Asn Gly Ser Thr Gln Gln Leu Pro Gln Thr Ile Ile Ile
    50                  55                  60

Gly Val Arg Lys Gly Gly Thr Arg Ala Leu Leu Glu Met Leu Ser Leu
 65                  70                  75                  80

His Pro Asp Val Ala Ala Ala Glu Asn Glu Val His Phe Phe Asp Trp
                85                  90                  95

Glu Glu His Tyr Ser Gln Gly Leu Gly Trp Tyr Leu Thr Gln Met Pro
            100                 105                 110

Phe Ser Ser Pro His Gln Leu Thr Val Glu Lys Thr Pro Ala Tyr Phe
        115                 120                 125

Thr Ser Pro Lys Val Pro Glu Arg Ile His Ser Met Asn Pro Thr Ile
    130                 135                 140

Arg Leu Leu Leu Ile Leu Arg Asp Pro Ser Glu Arg Val Leu Ser Asp
145                 150                 155                 160

Tyr Thr Gln Val Leu Tyr Asn His Leu Gln Lys His Lys Pro Tyr Pro
                165                 170                 175

Pro Ile Glu Asp Leu Leu Met Arg Asp Gly Arg Leu Asn Leu Asp Tyr
            180                 185                 190

Lys Ala Leu Asn Arg Ser Leu Tyr His Ala His Met Leu Asn Trp Leu
        195                 200                 205

Arg Phe Phe Pro Leu Gly His Ile His Ile Val Asp Gly Asp Arg Leu
    210                 215                 220

Ile Arg Asp Pro Phe Pro Glu Ile Gln Lys Val Glu Arg Phe Leu Lys
225                 230                 235                 240

Leu Ser Pro Gln Ile Asn Ala Ser Asn Phe Tyr Phe Asn Lys Thr Lys
                245                 250                 255

Gly Phe Tyr Cys Leu Arg Asp Ser Gly Lys Asp Arg Cys Leu His Glu
            260                 265                 270

Ser Lys Gly Arg Ala His Pro Gln Val Asp Pro Lys Leu Leu Asp Lys
        275                 280                 285

Leu His Glu Tyr Phe His Glu Pro Asn Lys Lys Phe Lys Leu Val
    290                 295                 300

Gly Arg Thr Phe Asp Trp His
305                 310
```

<210> SEQ ID NO 3
<211> LENGTH: 1305
<212> TYPE: DNA
<213> ORGANISM: Homo sapiens
<220> FEATURE:
<221> NAME/KEY: CDS
<222> LOCATION: (119)..(1039)
<223> OTHER INFORMATION: human 3-OST-1

<400> SEQUENCE: 3

```
cgcggctcag taattgaagg cctgaaacgc ccatgtgcca ctgactagga ggcttccctg      60
ctgcggcact tcatgaccca gcggcgcgcg gcccagtgaa gccaccgtgg tgtccagc      118
```

| | | |
|---|---|---|
| atg gcc gcg ctg ctc ctg ggc gcg gtg ctg ctg gtg gcc cag ccc cag<br>Met Ala Ala Leu Leu Leu Gly Ala Val Leu Leu Val Ala Gln Pro Gln<br>1               5                   10                  15 | 166 |
| cta gtg cct tcc cgc ccc gcc gag cta ggc cag cag gag ctt ctg cgg<br>Leu Val Pro Ser Arg Pro Ala Glu Leu Gly Gln Gln Glu Leu Leu Arg<br>            20                  25                  30 | 214 |
| aaa gcg ggg acc ctc cag gat gac gtc cgc gat ggc gtg gcc cca aac<br>Lys Ala Gly Thr Leu Gln Asp Asp Val Arg Asp Gly Val Ala Pro Asn<br>        35                  40                  45 | 262 |
| ggc tct gcc cag cag ttg ccg cag acc atc atc atc ggc gtg cgc aag<br>Gly Ser Ala Gln Gln Leu Pro Gln Thr Ile Ile Ile Gly Val Arg Lys<br>    50                  55                  60 | 310 |
| ggc ggc acg cgc gca ctg ctg gag atg ctc agc ctg cac ccc gac gtg<br>Gly Gly Thr Arg Ala Leu Leu Glu Met Leu Ser Leu His Pro Asp Val<br>65                  70                  75                  80 | 358 |
| gcg gcc gcg gag aac gag gtc cac ttc ttc gac tgg gag gag cat tac<br>Ala Ala Ala Glu Asn Glu Val His Phe Phe Asp Trp Glu Glu His Tyr<br>                85                  90                  95 | 406 |
| agc cac ggc ttg ggc tgg tac ctc agc cag atg ccc ttc tcc tgg cca<br>Ser His Gly Leu Gly Trp Tyr Leu Ser Gln Met Pro Phe Ser Trp Pro<br>            100                 105                 110 | 454 |
| cac cag ctc aca gtg gag aag acc ccc gcg tat ttc acg tcg ccc aaa<br>His Gln Leu Thr Val Glu Lys Thr Pro Ala Tyr Phe Thr Ser Pro Lys<br>        115                 120                 125 | 502 |
| gtg cct gag cga gtc tac agc atg aac ccg tcc atc cgg ctg ctg ctc<br>Val Pro Glu Arg Val Tyr Ser Met Asn Pro Ser Ile Arg Leu Leu Leu<br>    130                 135                 140 | 550 |
| atc ctg cga gac ccg tcg gag cgc gtg cta tct gac tac acc caa gtg<br>Ile Leu Arg Asp Pro Ser Glu Arg Val Leu Ser Asp Tyr Thr Gln Val<br>145                 150                 155                 160 | 598 |
| ttc tac aac cac atg cag aag cac aag ccc tac ccg tcc atc gag gag<br>Phe Tyr Asn His Met Gln Lys His Lys Pro Tyr Pro Ser Ile Glu Glu<br>                165                 170                 175 | 646 |
| ttc ctg gtg cgc gat ggc agg ctc aat gtg gac tac aag gcc ctc aac<br>Phe Leu Val Arg Asp Gly Arg Leu Asn Val Asp Tyr Lys Ala Leu Asn<br>            180                 185                 190 | 694 |
| cgc agc ctc tac cac gtg cac atg cag aac tgg ctg cgc ttt ttc ccg<br>Arg Ser Leu Tyr His Val His Met Gln Asn Trp Leu Arg Phe Phe Pro<br>        195                 200                 205 | 742 |
| ctg cgc cac atc cac att gtg gac ggc gac cgc ctc atc agg gac ccc<br>Leu Arg His Ile His Ile Val Asp Gly Asp Arg Leu Ile Arg Asp Pro<br>    210                 215                 220 | 790 |
| ttc cct gag atc caa aag gtc gag agg ttc cta aag ctg tcg ccg cag<br>Phe Pro Glu Ile Gln Lys Val Glu Arg Phe Leu Lys Leu Ser Pro Gln<br>225                 230                 235                 240 | 838 |
| atc aat gct tcg aac ttc tac ttt aac aaa acc aag ggc ttt tac tgc<br>Ile Asn Ala Ser Asn Phe Tyr Phe Asn Lys Thr Lys Gly Phe Tyr Cys<br>                245                 250                 255 | 886 |
| ctg cgg gac agc ggc cgg gac cgc tgc tta cat gag tcc aaa ggc cgg<br>Leu Arg Asp Ser Gly Arg Asp Arg Cys Leu His Glu Ser Lys Gly Arg<br>            260                 265                 270 | 934 |
| gcg cac ccc caa gtc gat ccc aaa cta ctc aat aaa ctg cac gaa tat<br>Ala His Pro Gln Val Asp Pro Lys Leu Leu Asn Lys Leu His Glu Tyr<br>        275                 280                 285 | 982 |

```
ttt cat gag cca aat aag aag ttc ttc gag ctt gtt ggc aga aca ttt      1030
Phe His Glu Pro Asn Lys Lys Phe Phe Glu Leu Val Gly Arg Thr Phe
    290                 295                 300 gac tgg cac tgatttgcaa taagctaagc tcagaaactt tcctactgta              1079
Asp Trp His
305 agttctggtg tacatctgag gggaaaaaga attttaaaaa agcatttaag gtataattta    1139 tttgtaaaat ccataaagta cttctgtaca gtattagatt cacaattgcc atatatacta    1199 gttatatttt tctacttgtt aaatggaggg cattttgtat tgttttcat ggttgttaac     1259 attgtgtaat atgtctctat atgaaggaac taaactattt cactga                    1305
```

<210> SEQ ID NO 4
<211> LENGTH: 307
<212> TYPE: PRT
<213> ORGANISM: Homo sapiens

<400> SEQUENCE: 4

```
Met Ala Ala Leu Leu Leu Gly Ala Val Leu Leu Val Ala Gln Pro Gln
  1               5                  10                  15

Leu Val Pro Ser Arg Pro Ala Glu Leu Gly Gln Gln Glu Leu Leu Arg
             20                  25                  30

Lys Ala Gly Thr Leu Gln Asp Asp Val Arg Asp Gly Val Ala Pro Asn
         35                  40                  45

Gly Ser Ala Gln Gln Leu Pro Gln Thr Ile Ile Gly Val Arg Lys
     50                  55                  60

Gly Gly Thr Arg Ala Leu Leu Glu Met Leu Ser Leu His Pro Asp Val
 65                  70                  75                  80

Ala Ala Ala Glu Asn Glu Val His Phe Phe Asp Trp Glu Glu His Tyr
                 85                  90                  95

Ser His Gly Leu Gly Trp Tyr Leu Ser Gln Met Pro Phe Ser Trp Pro
            100                 105                 110

His Gln Leu Thr Val Glu Lys Thr Pro Ala Tyr Phe Thr Ser Pro Lys
        115                 120                 125

Val Pro Glu Arg Val Tyr Ser Met Asn Pro Ser Ile Arg Leu Leu
    130                 135                 140

Ile Leu Arg Asp Pro Ser Glu Arg Val Leu Ser Asp Tyr Thr Gln Val
145                 150                 155                 160

Phe Tyr Asn His Met Gln Lys His Lys Pro Tyr Pro Ser Ile Glu Glu
                165                 170                 175

Phe Leu Val Arg Asp Gly Arg Leu Asn Val Asp Tyr Lys Ala Leu Asn
            180                 185                 190

Arg Ser Leu Tyr His Val His Met Gln Asn Trp Leu Arg Phe Phe Pro
        195                 200                 205

Leu Arg His Ile His Ile Val Asp Gly Asp Arg Leu Ile Arg Asp Pro
    210                 215                 220

Phe Pro Glu Ile Gln Lys Val Glu Arg Phe Leu Lys Leu Ser Pro Gln
225                 230                 235                 240

Ile Asn Ala Ser Asn Phe Tyr Phe Asn Lys Thr Lys Gly Phe Tyr Cys
                245                 250                 255

Leu Arg Asp Ser Gly Arg Asp Arg Cys Leu His Glu Ser Lys Gly Arg
            260                 265                 270

Ala His Pro Gln Val Asp Pro Lys Leu Leu Asn Lys Leu His Glu Tyr
        275                 280                 285
```

```
                        -continued

Phe His Glu Pro Asn Lys Lys Phe Glu Leu Val Gly Arg Thr Phe
    290                 295                 300

Asp Trp His
305

<210> SEQ ID NO 5
<211> LENGTH: 1951
<212> TYPE: DNA
<213> ORGANISM: Homo sapiens
<220> FEATURE:
<221> NAME/KEY: CDS
<222> LOCATION: (73)..(1173)
<223> OTHER INFORMATION: human 3-OST-2

<400> SEQUENCE: 5
cgcagggcca cagcagctca gccgccggtg cccctcgga  aaccatgacc cccggcgcgg      60
gcccatggag cc atg gcc tat agg gtc ctg ggc cgc gcg ggg cca cct cag    111
              Met Ala Tyr Arg Val Leu Gly Arg Ala Gly Pro Pro Gln
                1               5                   10 ccg cgg agg gcg cgc agg ctg ctc ttc gcc ttc acg ctc tcg ctc tcc      159
Pro Arg Arg Ala Arg Arg Leu Leu Phe Ala Phe Thr Leu Ser Leu Ser
        15                  20                  25 tgc act tac ctg tgt tac agc ttc ctg tgc tgc tgc gac gac ctg ggt      207
Cys Thr Tyr Leu Cys Tyr Ser Phe Leu Cys Cys Cys Asp Asp Leu Gly
 30                  35                  40                  45 cgg agc cgc ctc ctc ggc gcg cct cgc tgc ctc cgc ggc ccc agc gcg      255
Arg Ser Arg Leu Leu Gly Ala Pro Arg Cys Leu Arg Gly Pro Ser Ala
                 50                  55                  60 ggc ggc cag aaa ctt ctc cag aag tcc cgc ccc tgt gat ccc tcc ggg      303
Gly Gly Gln Lys Leu Leu Gln Lys Ser Arg Pro Cys Asp Pro Ser Gly
             65                  70                  75 ccg acg ccc agc gag ccc agc gct ccc agc gcg ccc gcc gcc gtg          351
Pro Thr Pro Ser Glu Pro Ser Ala Pro Ser Ala Pro Ala Ala Val
         80                  85                  90 ccc gcc cct cgc ctc tcc ggt tcc aac cac tcc ggc tca ccc aag ctg      399
Pro Ala Pro Arg Leu Ser Gly Ser Asn His Ser Gly Ser Pro Lys Leu
     95                 100                 105 ggt acc aag cgg ttg ccc caa gcc ctc att gtg ggc gtg aag aag ggg      447
Gly Thr Lys Arg Leu Pro Gln Ala Leu Ile Val Gly Val Lys Lys Gly
110                 115                 120                 125 ggc acc cgg gcc gtg ctg gag ttt atc cga gta cac ccg gac gtg cgg      495
Gly Thr Arg Ala Val Leu Glu Phe Ile Arg Val His Pro Asp Val Arg
                130                 135                 140 gcc ttg ggc acg gaa ccc cac ttc ttt gac agg aac tac ggc cgc ggg      543
Ala Leu Gly Thr Glu Pro His Phe Phe Asp Arg Asn Tyr Gly Arg Gly
            145                 150                 155 ctg gat tgg tac agg agc ctg atg ccc agg acc ctc gag agc cag atc      591
Leu Asp Trp Tyr Arg Ser Leu Met Pro Arg Thr Leu Glu Ser Gln Ile
        160                 165                 170 acg ctg gag aag acg ccc agc tac ttt gtc act caa gag gct cct cga      639
Thr Leu Glu Lys Thr Pro Ser Tyr Phe Val Thr Gln Glu Ala Pro Arg
    175                 180                 185 cgc atc ttc aac atg tcc cga gac acc aag ctg atc gtg gtt gtg cgg      687
Arg Ile Phe Asn Met Ser Arg Asp Thr Lys Leu Ile Val Val Val Arg
190                 195                 200                 205 aac cct gtg acc cgt gcc atc tct gat tac acg cag aca ctc tcc aag      735
Asn Pro Val Thr Arg Ala Ile Ser Asp Tyr Thr Gln Thr Leu Ser Lys
                210                 215                 220 aag ccc gac atc ccg acc ttt gag ggc ctc tcc ttc cgc aac cgc acc      783
Lys Pro Asp Ile Pro Thr Phe Glu Gly Leu Ser Phe Arg Asn Arg Thr
            225                 230                 235
```

-continued

```
ctg ggc ctg gtg gac gtg tcg tgg aac gcc atc cgc atc ggc atg tac      831
Leu Gly Leu Val Asp Val Ser Trp Asn Ala Ile Arg Ile Gly Met Tyr
        240                 245                 250 gtg ctg cac ctg gag agc tgg ctg cag tac ttc ccg cta gct cag att      879
Val Leu His Leu Glu Ser Trp Leu Gln Tyr Phe Pro Leu Ala Gln Ile
    255                 260                 265 cac ttc gtc agt ggc gag cga ctc atc act gac ccg gcc ggc gag atg      927
His Phe Val Ser Gly Glu Arg Leu Ile Thr Asp Pro Ala Gly Glu Met
270                 275                 280                 285 ggg cga gtc cag gac ttc ctg ggc att aag aga ttc atc acg gac aag      975
Gly Arg Val Gln Asp Phe Leu Gly Ile Lys Arg Phe Ile Thr Asp Lys
                290                 295                 300 cac ttc tat ttc aac aag acc aaa gga ttc cct tgc ttg aaa aaa aca     1023
His Phe Tyr Phe Asn Lys Thr Lys Gly Phe Pro Cys Leu Lys Lys Thr
            305                 310                 315 gaa tcg agc ctc ctg cct cga tgc ttg ggc aaa tca aaa ggg aga act     1071
Glu Ser Ser Leu Leu Pro Arg Cys Leu Gly Lys Ser Lys Gly Arg Thr
        320                 325                 330 cat gta cag att gat cct gaa gtg ata gac cag ctc cga gaa ttt tat     1119
His Val Gln Ile Asp Pro Glu Val Ile Asp Gln Leu Arg Glu Phe Tyr
    335                 340                 345 aga ccg tat aat atc aaa ttt tat gaa acc gtt ggg cag gac ttc agg     1167
Arg Pro Tyr Asn Ile Lys Phe Tyr Glu Thr Val Gly Gln Asp Phe Arg
350                 355                 360                 365 tgg gaa taagcccacg aaaggaaagg gctctcaagg gctcttctgc tcatctcttc     1223
Trp Glu cgtgagattt gctcccagac cctcttatct ccctccaaca aaccctggct ccagcccct   1283 ttcccaactt gagttgcatc atcttggaac caggaagccc agctaaagcc aagagaccag   1343
agagtctctg ccactagttt tcatcagtct gttcaagcaa agttgatctg ctcctggcac   1403
gtccagtaaa ttccagaatc attctccttt ctgcccataa agggccttgg agaattgctt   1463
taagaagagt gaatgttcca atgatgatag atattataag cgacgatggt tctgttgcta   1523
tgaacacagc agtcggtccc tgtcattgtc cacccaggag tggccttgtt aattccaagt   1583
ggcatgtatc ttccctctga gcttcatttc ttcaagatgc tctgggtggt gggatgggag   1643
accatcctca gccctcctca gaccttatca attcattgag agattgcaaa gctgaaagca   1703
cctccggcca ctcctgggag acagaccctt tggtgatgaa ataaaccagt gacttcagag   1763
cctatggtct caactgtgct tgaaaaacac tgtctctgaa acaactttg tgattctccc    1823 tgctccctgt ggacaaaagc acataattct gctgttacgg gtactttgct catacgagct   1883
ttcatgttca gcatgcaatg gaatcatgct tgtccatgtg aaataaatat ggctctctcg   1943
tgtcctta                                                             1951
```

<210> SEQ ID NO 6
<211> LENGTH: 367
<212> TYPE: PRT
<213> ORGANISM: Homo sapiens

<400> SEQUENCE: 6

```
Met Ala Tyr Arg Val Leu Gly Arg Ala Gly Pro Pro Gln Pro Arg Arg
  1               5                  10                  15

Ala Arg Arg Leu Leu Phe Ala Phe Thr Leu Ser Leu Ser Cys Thr Tyr
             20                  25                  30

Leu Cys Tyr Ser Phe Leu Cys Cys Cys Asp Asp Leu Gly Arg Ser Arg
         35                  40                  45
```

-continued

```
Leu Leu Gly Ala Pro Arg Cys Leu Arg Gly Pro Ser Ala Gly Gly Gln
 50                  55                  60
Lys Leu Leu Gln Lys Ser Arg Pro Cys Asp Pro Ser Gly Pro Thr Pro
 65                  70                  75                  80
Ser Glu Pro Ser Ala Pro Ser Ala Pro Ala Ala Val Pro Ala Pro
                 85                  90                  95
Arg Leu Ser Gly Ser Asn His Ser Gly Ser Pro Lys Leu Gly Thr Lys
                100                 105                 110
Arg Leu Pro Gln Ala Leu Ile Val Gly Val Lys Lys Gly Thr Arg
            115                 120                 125
Ala Val Leu Glu Phe Ile Arg Val His Pro Asp Val Arg Ala Leu Gly
        130                 135                 140
Thr Glu Pro His Phe Phe Asp Arg Asn Tyr Gly Arg Gly Leu Asp Trp
145                 150                 155                 160
Tyr Arg Ser Leu Met Pro Arg Thr Leu Glu Ser Gln Ile Thr Leu Glu
                165                 170                 175
Lys Thr Pro Ser Tyr Phe Val Thr Gln Glu Ala Pro Arg Arg Ile Phe
                180                 185                 190
Asn Met Ser Arg Asp Thr Lys Leu Ile Val Val Val Arg Asn Pro Val
            195                 200                 205
Thr Arg Ala Ile Ser Asp Tyr Thr Gln Thr Leu Ser Lys Lys Pro Asp
        210                 215                 220
Ile Pro Thr Phe Glu Gly Leu Ser Phe Arg Asn Arg Thr Leu Gly Leu
225                 230                 235                 240
Val Asp Val Ser Trp Asn Ala Ile Arg Ile Gly Met Tyr Val Leu His
                245                 250                 255
Leu Glu Ser Trp Leu Gln Tyr Phe Pro Leu Ala Gln Ile His Phe Val
                260                 265                 270
Ser Gly Glu Arg Leu Ile Thr Asp Pro Ala Gly Glu Met Gly Arg Val
            275                 280                 285
Gln Asp Phe Leu Gly Ile Lys Arg Phe Ile Thr Asp Lys His Phe Tyr
        290                 295                 300
Phe Asn Lys Thr Lys Gly Phe Pro Cys Leu Lys Lys Thr Glu Ser Ser
305                 310                 315                 320
Leu Leu Pro Arg Cys Leu Gly Lys Ser Lys Gly Arg Thr His Val Gln
                325                 330                 335
Ile Asp Pro Glu Val Ile Asp Gln Leu Arg Glu Phe Tyr Arg Pro Tyr
            340                 345                 350
Asn Ile Lys Phe Tyr Glu Thr Val Gly Gln Asp Phe Arg Trp Glu
        355                 360                 365
```

<210> SEQ ID NO 7
<211> LENGTH: 2314
<212> TYPE: DNA
<213> ORGANISM: Homo sapiens
<220> FEATURE:
<221> NAME/KEY: CDS
<222> LOCATION: (799)..(2016)
<223> OTHER INFORMATION: human 3-OST-3A

<400> SEQUENCE: 7

```
cagcggcggc ccaggaggca gccggtgagc gcctgcgagc agagtggcgg gggccgctga      60
caggtcccgc gcagcccagc ccagcccagc cacgcggctc acaggtgggg tccaagagca     120
gtttggagca acccgcgct acggagaggg gtggacggct ctgcacggc ctcctgtctc      180 ccgctcgggc agagggactc gggggggacct cgctccttgg ccgagagaac ctgaactcgg     240
```

```
                                                                -continued gcggagagaa cgcgcccagg cgggcaaggg gaccagagaa agccggggct ggaagtcact    300
gtcgctcgcc actgtctgga gcgcacgagc gcagaggcc cggcagccgc gcgtgccctc    360
ccggggaccg agccagtgat gcaggatcgc tgagcggaga tccgcgccga gaagtctctc    420
ggggccgggg ctgagacgca cgccttcgac accgctgcca agaccccgat tccggcgact    480
cttgcgggga accgagggcc caaggctgcc ccaagctcag gacttgggcg agtctaagac    540
gatggtttct taagcacgga cccgcgttcc ccttcccgcc ccctcgactg gaggcaggga    600
tcctgcgcgg ggccccgggg attccgtttc cccgcggagc cccggccgct gcctcccggg    660
acagttcgca cggccacagg ggcgcacggc gatgtggcct ccgtccagcg cgctggcccg    720 ccgggggggat gctctggcac ctgtcggggt ccaggcctag catggccggc gcgttgcccg    780
acgtcgcctc cggctagg atg gcc cct ccg ggc ccg gcc agt gcc ctc tcc     831
                    Met Ala Pro Pro Gly Pro Ala Ser Ala Leu Ser
                     1               5                  10 acc tcg gcc gag ccg ctg tcc cgc agc atc ttc cgg aag ttc ttg ctg    879
Thr Ser Ala Glu Pro Leu Ser Arg Ser Ile Phe Arg Lys Phe Leu Leu
         15                  20                  25 atg ctc tgc tcc ctg ctc acg tcc ctt tac gtc ttc tac tgc ctg gcc    927
Met Leu Cys Ser Leu Leu Thr Ser Leu Tyr Val Phe Tyr Cys Leu Ala
     30                  35                  40 gag cgc tgc cag acc ctg tcc ggc ccc gtc gtg ggg ctg tcc ggc ggc    975
Glu Arg Cys Gln Thr Leu Ser Gly Pro Val Val Gly Leu Ser Gly Gly
 45                  50                  55 ggc gag gag gcg ggg gcc cct ggt ggc ggc gtc ctg gcc gga ggc ccg   1023
Gly Glu Glu Ala Gly Ala Pro Gly Gly Gly Val Leu Ala Gly Gly Pro
 60                  65                  70                  75 agg gag ctg gcg gtg tgg ccg gcg gcg gca cag aga aag cgc ctc ctg   1071
Arg Glu Leu Ala Val Trp Pro Ala Ala Ala Gln Arg Lys Arg Leu Leu
                 80                  85                  90 caa ctg ccg cag tgg cgg agg cgc cgg ccg ccc gcg ccc cgc gac gac   1119
Gln Leu Pro Gln Trp Arg Arg Arg Pro Pro Ala Pro Arg Asp Asp
                 95                 100                 105 ggc gag gag gcg gcc tgg gaa gaa gag tcc cct ggc ctg tca ggg ggt   1167
Gly Glu Glu Ala Ala Trp Glu Glu Glu Ser Pro Gly Leu Ser Gly Gly
        110                 115                 120 ccg ggc ggc tcc ggg gcc gga agc acc gtg gcc gag gcc ccg ccg ggg   1215
Pro Gly Gly Ser Gly Ala Gly Ser Thr Val Ala Glu Ala Pro Pro Gly
125                 130                 135 acc ctg gcg ctg ctc ctg gac gaa ggc agc aag cag ctg ccg cag gcc   1263
Thr Leu Ala Leu Leu Leu Asp Glu Gly Ser Lys Gln Leu Pro Gln Ala
140                 145                 150                 155 atc atc atc gga gtg aag aag ggc ggc acg cgg gcg ctg ctg gag ttc   1311
Ile Ile Ile Gly Val Lys Lys Gly Gly Thr Arg Ala Leu Leu Glu Phe
                160                 165                 170 ctg cgc gtg cac ccc gac gtg cgc gcc gtg ggc gcc gag ccc cac ttc   1359
Leu Arg Val His Pro Asp Val Arg Ala Val Gly Ala Glu Pro His Phe
            175                 180                 185 ttc gac cgc agc tac gac aag ggc ctc gcc tgg tac cgg gac ctg atg   1407
Phe Asp Arg Ser Tyr Asp Lys Gly Leu Ala Trp Tyr Arg Asp Leu Met
        190                 195                 200 ccc aga acc ctg gac ggg cag atc acc atg gag aag acg ccc agt tac   1455
Pro Arg Thr Leu Asp Gly Gln Ile Thr Met Glu Lys Thr Pro Ser Tyr
205                 210                 215 ttc gtc acg cgg gag gcc ccc gcg cgc atc tcg gcc atg tcc aag gac   1503
Phe Val Thr Arg Glu Ala Pro Ala Arg Ile Ser Ala Met Ser Lys Asp
220                 225                 230                 235
```

-continued

| | | |
|---|---|---|
| acc aag ctc atc gtg gtg gtg cgg gac ccg gtg acc agg gcc atc tcg<br>Thr Lys Leu Ile Val Val Val Arg Asp Pro Val Thr Arg Ala Ile Ser<br>              240                         245                      250 | 1551 | |
| gac tac acg cag acg ctg tcc aag cgg ccc gac atc ccc acc ttc gag<br>Asp Tyr Thr Gln Thr Leu Ser Lys Arg Pro Asp Ile Pro Thr Phe Glu<br>        255                       260                       265 | 1599 | |
| agc ttg acg ttc aaa aac agg aca gcg ggc ctc atc gac acg tcg tgg<br>Ser Leu Thr Phe Lys Asn Arg Thr Ala Gly Leu Ile Asp Thr Ser Trp<br>    270                       275                      280 | 1647 | |
| agc gcc atc cag atc ggc atc tac gcc aag cac ctg gag cac tgg ctg<br>Ser Ala Ile Gln Ile Gly Ile Tyr Ala Lys His Leu Glu His Trp Leu<br>285                     290                       295 | 1695 | |
| cgc cac ttc ccc atc cgc cag atg ctc ttc gtg agc ggc gag cgg ctc<br>Arg His Phe Pro Ile Arg Gln Met Leu Phe Val Ser Gly Glu Arg Leu<br>300                   305                   310                 315 | 1743 | |
| atc agc gac ccg gcc ggg gag ctg ggc cgc gtg caa gac ttc ctg ggc<br>Ile Ser Asp Pro Ala Gly Glu Leu Gly Arg Val Gln Asp Phe Leu Gly<br>              320                       325                      330 | 1791 | |
| ctc aag agg atc atc acg gac aag cac ttc tac ttc aac aag acc aag<br>Leu Lys Arg Ile Ile Thr Asp Lys His Phe Tyr Phe Asn Lys Thr Lys<br>        335                       340                     345 | 1839 | |
| ggc ttc ccc tgc ctg aag aag gcg gag ggc agc agc cgg ccc cat tgc<br>Gly Phe Pro Cys Leu Lys Lys Ala Glu Gly Ser Ser Arg Pro His Cys<br>    350                       355                      360 | 1887 | |
| ctg ggc aag acc aag ggc agg acc cat cct gag atc gac cgc gag gtg<br>Leu Gly Lys Thr Lys Gly Arg Thr His Pro Glu Ile Asp Arg Glu Val<br>365                     370                       375 | 1935 | |
| gtg cgc agg ctg cgc gag ttc tac cgg cct ttc aac ctc aag ttc tac<br>Val Arg Arg Leu Arg Glu Phe Tyr Arg Pro Phe Asn Leu Lys Phe Tyr<br>380                     385                     390                 395 | 1983 | |
| cag atg acc ggg cac gac ttt ggc tgg gat gga taaccatata atttaaaaag<br>Gln Met Thr Gly His Asp Phe Gly Trp Asp Gly<br>              400                       405 | 2036 | |
| aaaaaaaaaa tcaaaatata atatattttt ttaccaatcg gtagagaaga gacagtttaa | 2096 | |
| tatttgtgct gaaaatatgt ttcagtattt ttttcaatga atgttaagag attgttctca | 2156 | |
| ctcccgcccc atcttaatgt ataaccaaca ccaaacacgt ggatcaacag aaaaggaaaa | 2216 | |
| tttcactcgt ctaaacactt tcaatttttca gttttttattt tatgttctat atacccagtc | 2276 | |
| ataaagtata agcatcagtt gtcattaaaa gttttcag | 2314 | |

<210> SEQ ID NO 8
<211> LENGTH: 406
<212> TYPE: PRT
<213> ORGANISM: Homo sapiens

<400> SEQUENCE: 8

Met Ala Pro Pro Gly Pro Ala Ser Ala Leu Ser Thr Ser Ala Glu Pro
1               5                   10                  15

Leu Ser Arg Ser Ile Phe Arg Lys Phe Leu Leu Met Leu Cys Ser Leu
            20                  25                  30

Leu Thr Ser Leu Tyr Val Phe Tyr Cys Leu Ala Glu Arg Cys Gln Thr
        35                  40                  45

Leu Ser Gly Pro Val Val Gly Leu Ser Gly Gly Glu Glu Ala Gly
    50                  55                  60

Ala Pro Gly Gly Gly Val Leu Ala Gly Gly Pro Arg Glu Leu Ala Val
65                  70                  75                  80

Trp Pro Ala Ala Ala Gln Arg Lys Arg Leu Leu Gln Leu Pro Gln Trp
                85                  90                  95

-continued

```
Arg Arg Arg Arg Pro Pro Ala Pro Arg Asp Asp Gly Glu Glu Ala Ala
            100                 105                 110
Trp Glu Glu Glu Ser Pro Gly Leu Ser Gly Pro Gly Gly Ser Gly
        115                 120                 125
Ala Gly Ser Thr Val Ala Glu Ala Pro Pro Gly Thr Leu Ala Leu Leu
        130                 135                 140
Leu Asp Glu Gly Ser Lys Gln Leu Pro Gln Ala Ile Ile Gly Val
145                 150                 155                 160
Lys Lys Gly Gly Thr Arg Ala Leu Leu Glu Phe Leu Arg Val His Pro
                165                 170                 175
Asp Val Arg Ala Val Gly Ala Glu Pro His Phe Asp Arg Ser Tyr
            180                 185                 190
Asp Lys Gly Leu Ala Trp Tyr Arg Asp Leu Met Pro Arg Thr Leu Asp
        195                 200                 205
Gly Gln Ile Thr Met Glu Lys Thr Pro Ser Tyr Phe Val Thr Arg Glu
    210                 215                 220
Ala Pro Ala Arg Ile Ser Ala Met Ser Lys Asp Thr Lys Leu Ile Val
225                 230                 235                 240
Val Val Arg Asp Pro Val Thr Arg Ala Ile Ser Asp Tyr Thr Gln Thr
                245                 250                 255
Leu Ser Lys Arg Pro Asp Ile Pro Thr Phe Glu Ser Leu Thr Phe Lys
            260                 265                 270
Asn Arg Thr Ala Gly Leu Ile Asp Thr Ser Trp Ser Ala Ile Gln Ile
        275                 280                 285
Gly Ile Tyr Ala Lys His Leu Glu His Trp Leu Arg His Phe Pro Ile
    290                 295                 300
Arg Gln Met Leu Phe Val Ser Gly Glu Arg Leu Ile Ser Asp Pro Ala
305                 310                 315                 320
Gly Glu Leu Gly Arg Val Gln Asp Phe Leu Gly Leu Lys Arg Ile Ile
                325                 330                 335
Thr Asp Lys His Phe Tyr Phe Asn Lys Thr Lys Gly Phe Pro Cys Leu
            340                 345                 350
Lys Lys Ala Glu Gly Ser Ser Arg Pro His Cys Leu Gly Lys Thr Lys
        355                 360                 365
Gly Arg Thr His Pro Glu Ile Asp Arg Glu Val Val Arg Arg Leu Arg
    370                 375                 380
Glu Phe Tyr Arg Pro Phe Asn Leu Lys Phe Tyr Gln Met Thr Gly His
385                 390                 395                 400
Asp Phe Gly Trp Asp Gly
                405
```

<210> SEQ ID NO 9
<211> LENGTH: 2032
<212> TYPE: DNA
<213> ORGANISM: Homo sapiens
<220> FEATURE:
<221> NAME/KEY: CDS
<222> LOCATION: (331)..(1500)
<223> OTHER INFORMATION: human 3-OST-3B

<400> SEQUENCE: 9

```
gtggccaggg cgcgagagtg caacgtcctc ctggccccga gcgcgtcgtc gcgccccggg      60
agcagaccct cgcccagcag ttaccgccgt cccgactttc cgttccagtt gcagctcctg     120
ccgggcaaca tgtcaagagc cgccgccgct acagctgccg ccgccacctg ggaagagca      180
gcagcagcag cggcggccgc gggcacacgg gggcaataaa ccgagccacc cgggcgtcca     240
```

```
gcgtgccggg gaaccctctc tgcgctcact gcccggcggg acccacgcca tgtgctgagc    300
catgtccctg gccgcgcccg cgggcagcgc atg ggg cag cgc ctg agt ggc ggc    354
                                Met Gly Gln Arg Leu Ser Gly Gly
                                  1               5 aga tct tgc ctc gat gtc ccc ggc cgg ctc cta ccg cag ccg ccg ccg    402
Arg Ser Cys Leu Asp Val Pro Gly Arg Leu Leu Pro Gln Pro Pro Pro
     10              15                  20 ccc ccg ccg ccg gtg agg agg aag ctc gcg ctg ctc ttc gcc atg ctc    450
Pro Pro Pro Pro Val Arg Arg Lys Leu Ala Leu Leu Phe Ala Met Leu
 25              30                  35              40 tgc gtc tgg ctc tat atg ttc ctg tac tcg tgc gcc ggc tcc tgc gcc    498
Cys Val Trp Leu Tyr Met Phe Leu Tyr Ser Cys Ala Gly Ser Cys Ala
                 45                  50                  55 gcc gcg ccg ggg ctg ctc ctg ggc tct ggg tcc cgc gcc gca cac        546
Ala Ala Pro Gly Leu Leu Leu Gly Ser Gly Ser Arg Ala Ala His
             60                  65                  70 gac ccg cca gcc ctg gcc aca gct ccg gac ggg acg ccc ccc agg ctg    594
Asp Pro Pro Ala Leu Ala Thr Ala Pro Asp Gly Thr Pro Pro Arg Leu
         75                  80                  85 ccg ttc cgg gcg ccg cca gcc acc cca ctg gct tca ggc aag gag atg    642
Pro Phe Arg Ala Pro Pro Ala Thr Pro Leu Ala Ser Gly Lys Glu Met
 90                  95                 100 gcc gag ggc gct gcg agc ccg gag gag cag agt ccc gag gtg ccg gac    690
Ala Glu Gly Ala Ala Ser Pro Glu Glu Gln Ser Pro Glu Val Pro Asp
105             110                 115                 120 tcc cca agc ccc atc tcc agc ttt ttc agt ggg tct ggg agc aag cag    738
Ser Pro Ser Pro Ile Ser Ser Phe Phe Ser Gly Ser Gly Ser Lys Gln
                125                 130                 135 ctg ccg cag gcc atc atc atc ggc gtg aag aag ggc ggc acg cgg gcg    786
Leu Pro Gln Ala Ile Ile Ile Gly Val Lys Lys Gly Gly Thr Arg Ala
            140                 145                 150 ctg ctg gag ttt ctg cgc gtg cac ccc gac gtg cgc gcc gtg ggc gcc    834
Leu Leu Glu Phe Leu Arg Val His Pro Asp Val Arg Ala Val Gly Ala
        155                 160                 165 gag ccc cat ttc ttc gat cgc agc tac gac aag ggc ctc gct tgg tac    882
Glu Pro His Phe Phe Asp Arg Ser Tyr Asp Lys Gly Leu Ala Trp Tyr
170                 175                 180 cgg gac ctg atg ccc aga acc ctg gac ggg cag atc acc atg gag aag    930
Arg Asp Leu Met Pro Arg Thr Leu Asp Gly Gln Ile Thr Met Glu Lys
185                 190                 195                 200 acg ccc agt tac ttc gtc acg cgg gag gcc ccc gcg cgc atc tcg gcc    978
Thr Pro Ser Tyr Phe Val Thr Arg Glu Ala Pro Ala Arg Ile Ser Ala
                205                 210                 215 atg tcc aag gac acc aag ctc atc gtg gtg gtg cgg gac ccg gtg acc   1026
Met Ser Lys Asp Thr Lys Leu Ile Val Val Val Arg Asp Pro Val Thr
            220                 225                 230 agg gcc atc tcg gac tac acg cag acg ctg tcc aag cgg ccc gac atc   1074
Arg Ala Ile Ser Asp Tyr Thr Gln Thr Leu Ser Lys Arg Pro Asp Ile
        235                 240                 245 ccc acc ttc gag agc ttg acg ttc aaa aac agg aca gcg ggc ctc atc   1122
Pro Thr Phe Glu Ser Leu Thr Phe Lys Asn Arg Thr Ala Gly Leu Ile
250                 255                 260 gac acg tcg tgg agc gcc atc cag atc ggc atc tac gcc aag cac ctg   1170
Asp Thr Ser Trp Ser Ala Ile Gln Ile Gly Ile Tyr Ala Lys His Leu
265                 270                 275                 280 gag cac tgg ctg cgc cac ttc ccc atc cgc cag atg ctc ttc gtg agc   1218
Glu His Trp Leu Arg His Phe Pro Ile Arg Gln Met Leu Phe Val Ser
                285                 290                 295
```

-continued

| | | |
|---|---|---|
| ggc gag cgg ctc atc agc gac ccg gcc ggg gag ctg ggc cgc gtg caa<br>Gly Glu Arg Leu Ile Ser Asp Pro Ala Gly Glu Leu Gly Arg Val Gln<br>300                          305                       310 | 1266 |
| gac ttc ctg ggc ctc aag agg atc atc acg gac aag cac ttc tac ttc<br>Asp Phe Leu Gly Leu Lys Arg Ile Ile Thr Asp Lys His Phe Tyr Phe<br>315                        320                       325 | 1314 |
| aac aag acc aag ggc ttc ccc tgc ctg aag aag gcg gag ggc agc agc<br>Asn Lys Thr Lys Gly Phe Pro Cys Leu Lys Lys Ala Glu Gly Ser Ser<br>330                        335                       340 | 1362 |
| cgg ccc cat tgc ctg ggc aag acc aag ggc agg acc cat cct gag atc<br>Arg Pro His Cys Leu Gly Lys Thr Lys Gly Arg Thr His Pro Glu Ile<br>345                        350                       355                       360 | 1410 |
| gac cgc gag gtg gtg cgc agg ctg cgc gag ttc tac cgg cct ttc aac<br>Asp Arg Glu Val Val Arg Arg Leu Arg Glu Phe Tyr Arg Pro Phe Asn<br>                        365                       370                       375 | 1458 |
| ctc aag ttc tac cag atg acc ggg cac gac ttt ggc tgg gat<br>Leu Lys Phe Tyr Gln Met Thr Gly His Asp Phe Gly Trp Asp<br>380                        385                       390 | 1500 |
| tgagcagacc cgggctatgt accttaccca cgtggcttat ctattgacag agattatatg | 1560 |
| tatgtaaaat gtacagaaat ctattttata ataatttatt tttaattcat aagcaattaa | 1620 |
| ttcactaagc tgcctagcca cactctttag agagttagct tcataatctg ttaacattcc | 1680 |
| aaagtgttta actctagtat ttcgttttct tcttcacaat tgatggtgct tctattttt | 1740 |
| cttctcccct acctgttata tttaaaacaa agaaaagcac aacttgagat ttttgttgtt | 1800 |
| acgggtattc agccttcagt caccgtctga gttctccagt tgctgcctcc ttgtcttgtc | 1860 |
| ttgggtctcc cattccagct tccctgtctc ttcctgcctg tgtacctcgt aggaacgctg | 1920 |
| agctgcctca acagggctgt attctgaagg gcaggcctca tgcagcagcc tccttgcaga | 1980 |
| tgtggtgtcc cgtccaatga tgtagcctga aagccacagc cctagggttc tg | 2032 |

<210> SEQ ID NO 10
<211> LENGTH: 390
<212> TYPE: PRT
<213> ORGANISM: Homo sapiens

<400> SEQUENCE: 10

Met Gly Gln Arg Leu Ser Gly Gly Arg Ser Cys Leu Asp Val Pro Gly
1               5                   10                  15

Arg Leu Leu Pro Gln Pro Pro Pro Pro Pro Val Arg Arg Lys
            20                  25                  30

Leu Ala Leu Leu Phe Ala Met Leu Cys Val Trp Leu Tyr Met Phe Leu
        35                  40                  45

Tyr Ser Cys Ala Gly Ser Cys Ala Ala Pro Gly Leu Leu Leu Leu
    50                  55                  60

Gly Ser Gly Ser Arg Ala Ala His Asp Pro Pro Ala Leu Ala Thr Ala
65                  70                  75                  80

Pro Asp Gly Thr Pro Pro Arg Leu Pro Phe Arg Ala Pro Pro Ala Thr
                85                  90                  95

Pro Leu Ala Ser Gly Lys Glu Met Ala Glu Gly Ala Ala Ser Pro Glu
            100                 105                 110

Glu Gln Ser Pro Glu Val Pro Asp Ser Pro Ser Pro Ile Ser Ser Phe
        115                 120                 125

Phe Ser Gly Ser Gly Ser Lys Gln Leu Pro Gln Ala Ile Ile Ile Gly
    130                 135                 140

Val Lys Lys Gly Gly Thr Arg Ala Leu Leu Glu Phe Leu Arg Val His
145                 150                 155                 160

-continued

```
Pro Asp Val Arg Ala Val Gly Ala Glu Pro His Phe Phe Asp Arg Ser
                165                 170                 175
Tyr Asp Lys Gly Leu Ala Trp Tyr Arg Asp Leu Met Pro Arg Thr Leu
            180                 185                 190
Asp Gly Gln Ile Thr Met Glu Lys Thr Pro Ser Tyr Phe Val Thr Arg
        195                 200                 205
Glu Ala Pro Ala Arg Ile Ser Ala Met Ser Lys Asp Thr Lys Leu Ile
210                 215                 220
Val Val Val Arg Asp Pro Val Thr Arg Ala Ile Ser Asp Tyr Thr Gln
225                 230                 235                 240
Thr Leu Ser Lys Arg Pro Asp Ile Pro Thr Phe Glu Ser Leu Thr Phe
                245                 250                 255
Lys Asn Arg Thr Ala Gly Leu Ile Asp Thr Ser Trp Ser Ala Ile Gln
            260                 265                 270
Ile Gly Ile Tyr Ala Lys His Leu Glu His Trp Leu Arg His Phe Pro
        275                 280                 285
Ile Arg Gln Met Leu Phe Val Ser Gly Glu Arg Leu Ile Ser Asp Pro
290                 295                 300
Ala Gly Glu Leu Gly Arg Val Gln Asp Phe Leu Gly Leu Lys Arg Ile
305                 310                 315                 320
Ile Thr Asp Lys His Phe Tyr Phe Asn Lys Thr Lys Gly Phe Pro Cys
                325                 330                 335
Leu Lys Lys Ala Glu Gly Ser Ser Arg Pro His Cys Leu Gly Lys Thr
            340                 345                 350
Lys Gly Arg Thr His Pro Glu Ile Asp Arg Glu Val Val Arg Arg Leu
        355                 360                 365
Arg Glu Phe Tyr Arg Pro Phe Asn Leu Lys Phe Tyr Gln Met Thr Gly
370                 375                 380
His Asp Phe Gly Trp Asp
385                 390
```

<210> SEQ ID NO 11
<211> LENGTH: 3658
<212> TYPE: DNA
<213> ORGANISM: Homo sapiens
<220> FEATURE:
<221> NAME/KEY: CDS
<222> LOCATION: (847)..(2214)
<223> OTHER INFORMATION: Predicted human 3-OST-4 hnRNA

<400> SEQUENCE: 11

```
gaggatatcc cgggcgagag aagggagggt cggggatggg ctgagttgga gtcccagagg    60
aaaagcggaa gcgagagctt cgtcacccgc tgtcttccag ctcccggtgc gcggcaccgg   120
aggcaggcgt tgggctttac ctctctaaaa gtactgggc aaaggaatgg agaacacggc   180
gtcccgagct cccaagggag gggagtaaac gaggtgggt ggggaacacc ccaagtgcgt   240
gcgtgctggg gggctggggg gcacgatctc cgttctcccg ggtgccccag ccctagcgca   300
cgcctccgct cccccgcccc cttcgcaggc gcgcgcgagg cgcaccccc ttccctcggc   360
ggcgccgggc gcgcgcccgg cccctcctc ctccctccg cgcctctcct ctctcccggc    420
agaaagttag cagcggggaa ggaactctgg gctgcaacag cgcgcggcgg cggcggcaga   480
ggctgaagca gaagccgcgg cggagccggg gaagcggggg cgctgcagac ggagcaggtg   540
ccgccggcgg gtccgcgcgc ccccctcggt ccccttgcct gaggctgagg gggggcggt    600
ggtgggggg ccactcggac tcggcgggca gcgtggggcg gggggccatg cggccgggct    660
```

-continued

```
cccccctggc gcagcgggac agcggccagg gccgggggcg cagcggcgtc gcttcatgca      720
gccggggcgg ctgggcagcg gcggcggcgg cggcggcggc ggcggcgggg gcggcggctg      780
aaaccatgtc cggcagcgc cggggctgc cgccgccgcc gccgccgccg cgagccggga       840 gccgcg atg gcc cgg tgg ccc gca cct cct ccg cct ccg cct ccg cct        888
       Met Ala Arg Trp Pro Ala Pro Pro Pro Pro Pro Pro Pro Pro
        1               5                  10 cca cct ctg gcc gcg ccg ccg ccg ccc ggc gcc tct gct aag ggg ccg       936
Pro Pro Leu Ala Ala Pro Pro Pro Gly Ala Ser Ala Lys Gly Pro
15              20                  25                  30 ccg gcg cgc aag ctg ctt ttt atg tgc acc ttg tcc ctg tct gtc acc       984
Pro Ala Arg Lys Leu Leu Phe Met Cys Thr Leu Ser Leu Ser Val Thr
            35                  40                  45 tac ctg tgc tac agc ctc ctg ggc ggc tcg ggc tcc ctg caa ttc cct      1032
Tyr Leu Cys Tyr Ser Leu Leu Gly Gly Ser Gly Ser Leu Gln Phe Pro
                50                  55                  60 ctg gcg ctg cag gag tcg ccg ggc gcc gcc gcc gag ccc ccg ccg agc      1080
Leu Ala Leu Gln Glu Ser Pro Gly Ala Ala Ala Glu Pro Pro Pro Ser
                65                  70                  75 ccg ccg cca ccc tct ctg ctg cct acc ccc gtg cgc ctc ggc gcc ccc      1128
Pro Pro Pro Pro Ser Leu Leu Pro Thr Pro Val Arg Leu Gly Ala Pro
80                  85                  90 tcg cag ccg ccc gcg ccg ccg ccg ctg gac aac gcg agc cac ggg gag      1176
Ser Gln Pro Pro Ala Pro Pro Pro Leu Asp Asn Ala Ser His Gly Glu
95                  100                 105                 110 ccg ccc gag ccc cca gag cag cca gcc gcc ccc ggg acc gac ggc tgg      1224
Pro Pro Glu Pro Pro Glu Gln Pro Ala Ala Pro Gly Thr Asp Gly Trp
                115                 120                 125 ggg ctg ccg agc ggc ggc gga ggc gcc cgg gac gcc tgg ctc cgg acc      1272
Gly Leu Pro Ser Gly Gly Gly Gly Ala Arg Asp Ala Trp Leu Arg Thr
                130                 135                 140 ccg ctg gcc ccc agc gag atg atc acg gct cag agc gcg ctg ccg gag      1320
Pro Leu Ala Pro Ser Glu Met Ile Thr Ala Gln Ser Ala Leu Pro Glu
            145                 150                 155 agg gaa gcg cag gag tcc agc acc acc gac gag gat ctc gca ggc cgg      1368
Arg Glu Ala Gln Glu Ser Ser Thr Thr Asp Glu Asp Leu Ala Gly Arg
            160                 165                 170 aga gcg gcc aac ggg agc agc gag agg ggc ggc gcc gtc agc acc ccc      1416
Arg Ala Ala Asn Gly Ser Ser Glu Arg Gly Gly Ala Val Ser Thr Pro
175                 180                 185                 190 gac tat ggg gag aag aag ctg cca cag gcg ctc atc atc ggg gtc aag      1464
Asp Tyr Gly Glu Lys Lys Leu Pro Gln Ala Leu Ile Ile Gly Val Lys
                195                 200                 205 aaa gga ggg acc cgc gcg ctg ctg gag gcg atc cgc gtg cac ccg gac      1512
Lys Gly Gly Thr Arg Ala Leu Leu Glu Ala Ile Arg Val His Pro Asp
                210                 215                 220 gtg cgg gcg gtg ggc gta gag ccg cac ttc ttc gac agg aac tac gaa      1560
Val Arg Ala Val Gly Val Glu Pro His Phe Phe Asp Arg Asn Tyr Glu
            225                 230                 235 aag ggg ttg gag tgg tac aga aat gtg atg ccc aag act ttg gat ggg      1608
Lys Gly Leu Glu Trp Tyr Arg Asn Val Met Pro Lys Thr Leu Asp Gly
    240                 245                 250 caa ata acc atg gag aag act cca agt tac ttt gtg aca aat gag gct      1656
Gln Ile Thr Met Glu Lys Thr Pro Ser Tyr Phe Val Thr Asn Glu Ala
255                 260                 265                 270 ccc aag cgc att cac tcc atg gcc aag gac atc aaa ctg att gtg gtg      1704
Pro Lys Arg Ile His Ser Met Ala Lys Asp Ile Lys Leu Ile Val Val
                275                 280                 285
```

```
gtg aga aac ccc gtg acc agg gcc atc tct gac tac acg cag aca ctg        1752
Val Arg Asn Pro Val Thr Arg Ala Ile Ser Asp Tyr Thr Gln Thr Leu
            290                 295                 300 tca aag aaa ccc gag atc ccc acc ttt gag gtg ctg gcc ttc aaa aac        1800
Ser Lys Lys Pro Glu Ile Pro Thr Phe Glu Val Leu Ala Phe Lys Asn
        305                 310                 315 cgg acc ctc ggg ctg atc gat gct tcc tgg agt gcc att cga ata ggg        1848
Arg Thr Leu Gly Leu Ile Asp Ala Ser Trp Ser Ala Ile Arg Ile Gly
    320                 325                 330 atc tat gcg ctg cat ctg gaa aac tgg ctc cag tat ttc ccc ctc tcc        1896
Ile Tyr Ala Leu His Leu Glu Asn Trp Leu Gln Tyr Phe Pro Leu Ser
335                 340                 345                 350 cag atc ctc ttt gtc agt ggt gag cga ctc att gtg gac ccc gcc ggg        1944
Gln Ile Leu Phe Val Ser Gly Glu Arg Leu Ile Val Asp Pro Ala Gly
                355                 360                 365 gaa atg gcc aaa gta cag gat ttt cta ggc ctc aaa cgt gtt gtg act        1992
Glu Met Ala Lys Val Gln Asp Phe Leu Gly Leu Lys Arg Val Val Thr
            370                 375                 380 aag aag cat ttc tat ttc aac aaa acc aag ggg ttc cct tgc cta aag        2040
Lys Lys His Phe Tyr Phe Asn Lys Thr Lys Gly Phe Pro Cys Leu Lys
        385                 390                 395 aag cca gaa gac agc agt gcc ccg agg tgc tta ggc aag agc aaa ggt        2088
Lys Pro Glu Asp Ser Ser Ala Pro Arg Cys Leu Gly Lys Ser Lys Gly
    400                 405                 410 cgg act cat cct cgc att gac cca gat gtc atc cac aga ctg agg aaa        2136
Arg Thr His Pro Arg Ile Asp Pro Asp Val Ile His Arg Leu Arg Lys
415                 420                 425                 430 ttc tac aaa ccc ttc aac ttg atg ttt tac caa atg act ggt caa gat        2184
Phe Tyr Lys Pro Phe Asn Leu Met Phe Tyr Gln Met Thr Gly Gln Asp
                435                 440                 445 ttt cag tgg gaa cag gaa gag ggt gat aaa tgaggctaga gaggcagagg          2234
Phe Gln Trp Glu Gln Glu Glu Gly Asp Lys
            450                 455 aaggctagtc aataagctaa ggaggctcct tgcctgagtc cttgaatacc ccagcttctg      2294
cagcttcact tgctggagtg ccaagtagat ctcctcctcc ttcatgcagc caggattgcc      2354
tccagtgctg ttagcttagg caaacaggtg gatcccatgg catccccatg gaggaaccag      2414
gcccatctgg gcagcagcat ctggttgacc agatggccac cagaacccac tgttcattct      2474
tatcttctgc tagttaatat agcctgaaga cagaggataa atagttgtca atgtcagaga      2534
cagtgctatt aatgtatatg tgagcgacaa aaaaggtctg ctttataggg gttctcactc      2594
tagcttgggg agcccagggt tctagccctg tatctgtcat gggcacctgc tgtctaaacc      2654
tctgcttggg cttctcccca gaatgcactt tgtggctgag tgctccagga ctcctaggga      2714
gcaagctcct ccctctaagg tgtttctagt cttctcttta aaggtctcat cccacaaccc      2774
ctgacttcct ccctccccac atcatgaagg cagaggcatg cacattcctc actgaaaaag      2834
aaaacacaca cccacccaca cacacacaca cagaagaaaa tgaaagctga cacacctcga      2894
agccttcttt ccaagagccc tctaaatggg gttgggtctc actcttcatg agtatcctgg      2954
gttgtgcaga agcttagcat atgcccttgt gttcggatca ggcccacagg gctgctcaaa      3014
gagtagagta attgtaaccg aggtcagagc tctggggttg gcagagatga gtggccatat      3074
ctgggggtaa aagaagaaat cctgtcctct tggtgggagg ttaccttacc tgaagaccat      3134
ctctcccaag cactgtagtt ctgagcatgt ttttggggtg gactctgtcc cctagggtcc      3194
ctagaagggc aaagaccaga gagttgacaa gtctgttatt aggaataatc cttagccatg      3254
taatggagaa aggagcagtc agcattcttc caatttgccc caccaccacc tcctcgggct      3314
```

-continued

```
tcattttctc tatttagaga tggcagagag tgaggtagtg gcgagaaagc tgactccatt    3374
catcagatcc agtttatgag ggttgggggt gagcaagggc tgtctgcaga aaccccatc     3434 aagagctgct gaatgaagtg tcccttccca tcagtttgat tcaattaaaa tgcatcattt    3494
gacataaagc acttgttcac agatctccaa aaccaggaat tgttctagta aaactggaaa    3554
tttgtatgag tggggggagt taaatctgtt cagctgttat taaactgtca tttctcccgc    3614
taaatgaaaa ccgtgttgtt ataaagctta atgcaacctg atta                    3658
```

<210> SEQ ID NO 12
<211> LENGTH: 456
<212> TYPE: PRT
<213> ORGANISM: Homo sapiens

<400> SEQUENCE: 12

```
Met Ala Arg Trp Pro Ala Pro Pro Pro Pro Pro Pro Pro Pro Pro
  1               5                  10                  15

Leu Ala Ala Pro Pro Pro Gly Ala Ser Ala Lys Gly Pro Pro Ala
                 20                  25                  30

Arg Lys Leu Leu Phe Met Cys Thr Leu Ser Leu Ser Val Thr Tyr Leu
                 35                  40                  45

Cys Tyr Ser Leu Leu Gly Gly Ser Gly Ser Leu Gln Phe Pro Leu Ala
             50                  55                  60

Leu Gln Glu Ser Pro Gly Ala Ala Ala Glu Pro Pro Ser Pro Pro
 65                  70                  75                  80

Pro Pro Ser Leu Leu Pro Thr Pro Val Arg Leu Gly Ala Pro Ser Gln
                 85                  90                  95

Pro Pro Ala Pro Pro Pro Leu Asp Asn Ala Ser His Gly Glu Pro Pro
                100                 105                 110

Glu Pro Pro Glu Gln Pro Ala Ala Pro Gly Thr Asp Gly Trp Gly Leu
            115                 120                 125

Pro Ser Gly Gly Gly Gly Ala Arg Asp Ala Trp Leu Arg Thr Pro Leu
        130                 135                 140

Ala Pro Ser Glu Met Ile Thr Ala Gln Ser Ala Leu Pro Glu Arg Glu
145                 150                 155                 160

Ala Gln Glu Ser Ser Thr Thr Asp Glu Asp Leu Ala Gly Arg Arg Ala
                165                 170                 175

Ala Asn Gly Ser Ser Glu Arg Gly Gly Ala Val Ser Thr Pro Asp Tyr
            180                 185                 190

Gly Glu Lys Lys Leu Pro Gln Ala Leu Ile Ile Gly Val Lys Lys Gly
        195                 200                 205

Gly Thr Arg Ala Leu Leu Glu Ala Ile Arg Val His Pro Asp Val Arg
    210                 215                 220

Ala Val Gly Val Glu Pro His Phe Phe Asp Arg Asn Tyr Glu Lys Gly
225                 230                 235                 240

Leu Glu Trp Tyr Arg Asn Val Met Pro Lys Thr Leu Asp Gly Gln Ile
                245                 250                 255

Thr Met Glu Lys Thr Pro Ser Tyr Phe Val Thr Asn Glu Ala Pro Lys
            260                 265                 270

Arg Ile His Ser Met Ala Lys Asp Ile Lys Leu Ile Val Val Val Arg
        275                 280                 285

Asn Pro Val Thr Arg Ala Ile Ser Asp Tyr Thr Gln Thr Leu Ser Lys
    290                 295                 300

Lys Pro Glu Ile Pro Thr Phe Glu Val Leu Ala Phe Lys Asn Arg Thr
305                 310                 315                 320
```

-continued

```
Leu Gly Leu Ile Asp Ala Ser Trp Ser Ala Ile Arg Ile Gly Ile Tyr
            325                 330                 335

Ala Leu His Leu Glu Asn Trp Leu Gln Tyr Phe Pro Leu Ser Gln Ile
            340                 345                 350

Leu Phe Val Ser Gly Glu Arg Leu Ile Val Asp Pro Ala Gly Glu Met
            355                 360                 365

Ala Lys Val Gln Asp Phe Leu Gly Leu Lys Arg Val Val Thr Lys Lys
            370                 375                 380

His Phe Tyr Phe Asn Lys Thr Lys Gly Phe Pro Cys Leu Lys Lys Pro
385                 390                 395                 400

Glu Asp Ser Ser Ala Pro Arg Cys Leu Gly Lys Ser Lys Gly Arg Thr
                405                 410                 415

His Pro Arg Ile Asp Pro Asp Val Ile His Arg Leu Arg Lys Phe Tyr
                420                 425                 430

Lys Pro Phe Asn Leu Met Phe Tyr Gln Met Thr Gly Gln Asp Phe Gln
                435                 440                 445

Trp Glu Gln Glu Glu Gly Asp Lys
            450                 455

<210> SEQ ID NO 13
<211> LENGTH: 284
<212> TYPE: PRT
<213> ORGANISM: Homo sapiens
<220> FEATURE:
<223> OTHER INFORMATION: human NST-1 (aa 599 to 882)

<400> SEQUENCE: 13

Lys Thr Cys Asp Arg Phe Pro Lys Leu Leu Ile Ile Gly Pro Gln Lys
  1               5                  10                  15

Thr Gly Thr Thr Ala Leu Tyr Leu Phe Leu Gly Met His Pro Asp Leu
                 20                  25                  30

Ser Ser Asn Tyr Pro Ser Ser Glu Thr Phe Glu Glu Ile Gln Phe Phe
             35                  40                  45

Asn Gly His Asn Tyr His Lys Gly Ile Asp Trp Tyr Met Glu Phe Phe
         50                  55                  60

Pro Ile Pro Ser Asn Thr Thr Ser Asp Phe Tyr Phe Glu Lys Ser Ala
 65                  70                  75                  80

Asn Tyr Phe Asp Ser Glu Val Ala Pro Arg Arg Ala Ala Ala Leu Leu
                 85                  90                  95

Pro Lys Ala Lys Val Leu Thr Ile Leu Ile Asn Pro Ala Asp Arg Ala
            100                 105                 110

Tyr Ser Trp Tyr Gln His Gln Arg Ala His Asp Asp Pro Val Ala Leu
            115                 120                 125

Lys Tyr Thr Phe His Glu Val Ile Thr Ala Gly Ser Asp Ala Ser Ser
130                 135                 140

Lys Leu Arg Ala Leu Gln Asn Arg Cys Leu Val Pro Gly Trp Tyr Ala
145                 150                 155                 160

Thr His Ile Glu Arg Trp Leu Ser Ala Tyr His Ala Asn Gln Ile Leu
                165                 170                 175

Val Leu Asp Gly Lys Leu Leu Arg Thr Glu Pro Ala Lys Val Met Asp
            180                 185                 190

Met Val Gln Lys Phe Leu Gly Val Thr Asn Thr Ile Asp Tyr His Lys
            195                 200                 205

Thr Leu Ala Phe Asp Pro Lys Lys Gly Phe Trp Cys Gln Leu Leu Glu
        210                 215                 220
```

```
Gly Gly Lys Thr Lys Cys Leu Gly Lys Ser Lys Gly Arg Lys Tyr Pro
225                 230                 235                 240

Glu Met Asp Leu Asp Ser Arg Ala Phe Leu Lys Asp Tyr Tyr Arg Asp
                245                 250                 255

His Asn Ile Glu Leu Ser Lys Leu Leu Tyr Lys Met Gly Gln Thr Leu
            260                 265                 270

Pro Thr Trp Leu Arg Glu Asp Leu Gln Asn Thr Arg
        275                 280

<210> SEQ ID NO 14
<211> LENGTH: 286
<212> TYPE: PRT
<213> ORGANISM: Homo sapiens
<220> FEATURE:
<223> OTHER INFORMATION: human NST-2 (aa 598 to 883)

<400> SEQUENCE: 14

Lys Thr Cys Asp Arg Leu Pro Lys Phe Leu Ile Val Gly Pro Gln Lys
  1               5                  10                  15

Thr Gly Thr Thr Ala Ile His Phe Phe Leu Ser Leu His Pro Ala Val
                 20                  25                  30

Thr Ser Ser Phe Pro Ser Pro Ser Thr Phe Glu Glu Ile Gln Phe Phe
             35                  40                  45

Asn Ser Pro Asn Tyr His Lys Gly Ile Asp Trp Tyr Met Asp Phe Phe
 50                  55                  60

Pro Val Pro Ser Asn Ala Ser Thr Asp Phe Leu Phe Glu Lys Ser Ala
 65                  70                  75                  80

Thr Tyr Phe Asp Ser Glu Val Val Pro Arg Arg Gly Ala Ala Leu Leu
                 85                  90                  95

Pro Arg Ala Lys Ile Ile Thr Val Leu Thr Asn Pro Ala Asp Arg Ala
            100                 105                 110

Tyr Ser Trp Tyr Gln His Gln Arg Ala His Gly Asp Pro Val Ala Leu
        115                 120                 125

Asn Tyr Thr Phe Tyr Gln Val Ile Ser Ala Ser Ser Gln Thr Pro Leu
130                 135                 140

Ala Leu Arg Ser Leu Gln Asn Arg Cys Leu Val Pro Gly Tyr Tyr Ser
145                 150                 155                 160

Thr His Leu Gln Arg Trp Leu Thr Tyr Tyr Pro Ser Gly Gln Leu Leu
                165                 170                 175

Ile Val Asp Gly Gln Glu Leu Arg Thr Asn Pro Ala Ala Ser Met Glu
            180                 185                 190

Ser Ile Gln Lys Phe Leu Gly Ile Thr Pro Phe Leu Asn Tyr Thr Arg
        195                 200                 205

Thr Leu Arg Phe Asp Asp Asp Lys Gly Phe Trp Cys Gln Gly Leu Glu
210                 215                 220

Gly Gly Lys Thr Arg Cys Leu Gly Arg Ser Lys Gly Arg Arg Tyr Pro
225                 230                 235                 240

Asp Met Asp Thr Glu Ser Arg Leu Phe Leu Thr Asp Phe Phe Arg Asn
                245                 250                 255

His Asn Leu Glu Leu Ser Lys Leu Leu Ser Arg Leu Gly Gln Pro Val
            260                 265                 270

Pro Ser Trp Leu Arg Glu Glu Leu Gln His Ser Ser Leu Gly
        275                 280                 285
```

<210> SEQ ID NO 15
<211> LENGTH: 291
<212> TYPE: PRT
<213> ORGANISM: Caenorhabditis elegans
<220> FEATURE:
<223> OTHER INFORMATION: putative C. elegans 3-OST

<400> SEQUENCE: 15

```
Met Lys Tyr Arg Leu Leu Ile Leu His Leu Ile Asp Leu Ile Ser
 1               5                  10                  15

Cys Gly Val Ile Pro Asn Thr Ser Lys Lys Arg Phe Pro Asp Ala Ile
                20                  25                  30

Ile Val Gly Val Lys Lys Ser Gly Thr Arg Ala Leu Leu Glu Phe Leu
            35                  40                  45

Arg Val Asn Pro Leu Ile Lys Ala Pro Gly Pro Glu Val His Phe Phe
        50                  55                  60

Asp Lys Asn Phe Asn Lys Gly Leu Glu Trp Tyr Arg Glu Gln Met Pro
 65                  70                  75                  80

Glu Thr Lys Phe Gly Glu Val Thr Ile Glu Lys Ser Pro Ala Tyr Phe
                 85                  90                  95

His Ser Lys Met Ala Pro Glu Arg Ile Lys Ser Leu Asn Pro Asn Thr
            100                 105                 110

Lys Ile Ile Ile Val Val Arg Asp Pro Val Thr Arg Ala Ile Ser Asp
        115                 120                 125

Tyr Thr Gln Ser Ser Ser Lys Arg Lys Arg Val Gly Leu Met Pro Ser
130                 135                 140

Phe Glu Thr Met Ala Val Gly Asn Cys Ala Asn Trp Leu Arg Thr Asn
145                 150                 155                 160

Cys Thr Thr Lys Thr Arg Gly Val Asn Ala Gly Trp Gly Ala Ile Arg
                165                 170                 175

Ile Gly Val Tyr His Lys His Met Lys Arg Trp Leu Asp His Phe Pro
            180                 185                 190

Ile Glu Asn Ile His Ile Val Asp Gly Glu Lys Leu Ile Ser Asn Pro
        195                 200                 205

Ala Asp Glu Ile Ser Ala Thr Glu Lys Phe Leu Gly Leu Lys Pro Val
    210                 215                 220

Ala Lys Pro Glu Lys Phe Gly Val Asp Pro Ile Lys Lys Phe Pro Cys
225                 230                 235                 240

Ile Lys Asn Glu Asp Gly Lys Leu His Cys Leu Gly Lys Thr Lys Gly
                245                 250                 255

Arg His His Pro Asp Val Glu Pro Ser Val Leu Lys Thr Leu Arg Glu
            260                 265                 270

Phe Tyr Gly Pro Glu Asn Lys Lys Phe Tyr Gln Met Ile Asn His Trp
        275                 280                 285

Phe Asp Trp
    290
```

<210> SEQ ID NO 16
<211> LENGTH: 4045
<212> TYPE: DNA
<213> ORGANISM: Homo sapiens
<220> FEATURE:
<223> OTHER INFORMATION: 3-OST-4  5' promoter/exon

<400> SEQUENCE: 16
gaattctgtg ggtgttggca ggggagacag aaaactatct tccatcgagt cttcggatcc    60
attgggaatg cctggatgac gtcagagttc gccctgtgta ggtagctccc acttttcatt   120

```
gtaggtttct caaggacttg ctcctagaaa aagcgtggct caaaagtaga taaaaaatag    180
gcaactgcct aagtgtgaaa tttacaaagt tcctctccaa aaaagcccgc ctcctcccta    240
tcacttgtgg gcctgacatt ttaccaaagg ggctctattc tttcaagagt ttgttattaa    300
agcgtgacta tttgaggatt ggaggcaaaa gggatactga gaaatgtcct tactagcagt    360
gtcaaggcaa gtgacataaa tgtgtgggggg ggcaacttgt atgagcactg tgaaaacggc    420
agcatgttca ctctacttct cagctctgac tgagggctc aaagttcagg atctgctgat    480
ttttcaacag taacgtcctc tccaaggtgt tttttttttt tccttttttg ggaaagcccc    540
cagtttaaac tattgcagcc agtttacatt tcttaatgtc actgtgctgg ccacattcag    600
agctccattt gccaccatcg gttttgatac cttttttacca aaacctttcg aaatttgaga    660
gcccatcttt agtaaaactg ggcatggagc agattcgttt ggattgctga gaggggagat    720
agaaaagttt gggtgctagg caggaactgc aaggaggacc tgggccatat gccagacatc    780
tagtgcctgg gccttgaaag ggagactggt cgctgacaag gcaatatctg ttgcaaccca    840
ggcttcctag atgaccacct tggatcatgg ctcggagcac agggagggct gggcagtgct    900
tgtgtttctc tccgttccag ttggccccctt cccattgaca ttacagtaat gcagttgtgt    960
gctgtttgaa aaagcatccc tagttacaca gaatgattta caggacacca gactctgcat   1020
ttcagaggtc tccagtgtac cataaaaaat atattataaa agaataatct ttatctgaac   1080
taaagctgca gtgaaggaaa ctcgtgtcca gctgagagca gcagtgagct tttgttcact   1140
cagggaaaag tccgtgttct ttatcttatt tgattaacat ttttttttctc tttggcacta   1200
ggtatctcgt taatatttag acattatata cattttcttt caactggttt tcctattacg   1260
tgatcaaaca aaaccagaga tgccagccac agcagccaac aagggaaaag cagccccgtc   1320
aggcacccag ctgtggctgg ggggcaaatg gtactcacta gagccacccc caggaggcac   1380
ctggcagagc tctgtgcaga gccagccccg gttgcagaaa gctgagtttg ttggagtgcc   1440
tcagttgatc actctgtctc tttctcccat ttccctcact tccctgagca aaatgcaaca   1500
ggaagcaaag tctagttgtg aatcttccaa agccttctga tgtttaccat gttcccccag   1560
gagagggagg tgagggggtgg agatctctct gcaaagaaaa tacacttaaa aaatttcagc   1620
gagccgatgc acagacaccc agcaacccag cttgtctccg cttattaggt gttcagagcg   1680
acagtggtcc cacactattt cagtccagga aaccatgaac tccgttagtg gcaatgcccc   1740
cgaagaggcg caggtgtgtg cacctgtgat taagggtgtc gaggaggggc agcctcatct   1800
cttgaagcag aaagtgttgt cacctggtga tgggacagag ggaaaagctc tggggctggg   1860
aaacctgggg gcttgtgtca agctccacc catcaggagc ttcaagagaa gatgggggggc   1920
ggggggcggt ggctggaaag atggaagttg ggatgggaaa gcggttgtag aaaaggattc   1980
actcctggac cgaaggcagg aggatatccc gggcgagaga agggagggtc gggatgggc    2040
tgagttggag tccagagga aaagcggaag cgagagcttc gtcacccgct gtcttccagc    2100
tcccggtgcg cggcaccgga ggcaggcgtt gggctttacc tctctaaaag tactggggca    2160
aaggaatgga gaacacggcg tcccgagctc ccaaggagg ggagtaaacg aggtgggtg     2220
gggaacaccc caagtgcgtg cgtgctgggg ggctgggggg cacgatctcc gttctcccgg   2280
gtgccccagc cctagcgcac gcctccgctc ccccgcccccc ttcgcaggcg cgcgcgaggc   2340
gcaccccct tccctcggcg gcgccgggcg cgcgcccggc ccctcctcc tccctccgc     2400
gcctctcctc tctcccggca gaaagttagc agcggggaag gaactctggg ctgcaacagc   2460
gcgcggcggc ggcggcagag gctgaagcag aagccgcggc ggagccgggg aagcggggc    2520
```

```
gctgcagacg gagcaggtgc cgccggcggg tccgcgcgcc cccctcggtc cccttgcctg    2580
aggctgaggg ggggcggtg gtggggggc cactcggact cggcgggcag cgtgggcgg      2640 ggggccatgc ggccgggctc ccccctggcg cagcgggaca gcggccaggg ccggggcgc    2700 agcggcgtcg cttcatgcag ccggggcggc tgggcagcgg cggcggcggc ggcggcggcg    2760
gcggcggggg cggcggctga aaccatgtcc gggcagcgcc gggggctgcc gccgccgccg    2820
ccgccgccgc gagccgggag ccgcgatggc ccggtgccc gcacctcctc cgcctccgcc     2880
tccgcctcca cctctggccg cgccgccgcc gcccggcgcc tctgctaagg ggccgccggc    2940
gcgcaagctg cttttatgt gcaccttgtc cctgtctgtc acctacctgt gctacagcct     3000
cctgggcggc tcgggctccc tgcaattccc tctggcgctg caggagtcgc cgggcgccgc    3060
cgccgagccc ccgccgagcc cgccgccacc ctctctgctg cctaccccg tgcgcctcgg     3120 cgcccctcg cagccgcccg cgccgccgcc gctggacaac gcgagccacg gggagccgcc     3180
cgagccccca gagcagccag ccgcccccgg gaccgacggc tgggggctgc cgagcggcgg    3240
cggaggcgcc cgggacgcct ggctccggac cccgctggcc cccagcgaga tgatcacggc    3300
tcagagcgcg ctgccggaga gggaagcgca ggagtccagc accaccgacg aggatctcgc    3360
aggccggaga gcggccaacg ggagcagcga gaggggcggc gccgtcagca ccccgacta     3420 tggggagaag aagctgccac aggcgctcat catcggggtc aagaaaggag ggaccccgcgc   3480 gctgctggag gcgatccgcg tgcacccgga cgtgcgggcg gtgggcgtag agccgcactt    3540
cttcgacagg aactacgaaa aggggttgga gtggtacagg taggaccctg ggctccgcgg    3600
gctggtggag acgcgtgggg gagacgcgga ggggaagccg cggctttcca cgcccttcga    3660
gcatccaggc accgtcccga gaggcccaag ccccgcgag ggctctgcaa accctggcgg     3720
cgttgctcag ggggatcggc tgagagggct ggactccagc gaaaggtcac tttatttcag    3780
ggcgagggga ggaggtgtca ccctgccctg cctcccgcgc tcctcatcca aggaggtgct    3840
gtctgaatct gcccagctcc aagcctggga accccagcc ctcctgcctg ctgggtgttt     3900
ccgaaaccag gctcttgcgg ggttctggga ttctgggcag aggactttga ggagtgagac    3960
aggatggcta aattgactaa ggggatttga ggtccctgg aatctcttaa aatcaccctc     4020
aaacgcattt gcgtggctgg aattc                                         4045
```

HEPARAN SULFATE D-GLUCOSAMINYL 3-O-SULFOTRANSFERASES, AND USES THEREFOR

CROSS-REFERENCE TO RELATED APPLICATION

This application is a Continuation of PCT International Patent Application Serial No. PCT/US98/22597, filed on Oct. 23, 1998, which claims priority of U.S. Provisional Patent Application Ser. No. 60/062,762, filed on Oct. 24, 1997 and U.S. Provisional Patent Application Ser. No. 60/065,437, filed on Oct. 31, 1997.

FIELD OF THE INVENTION

The present invention is related to the field of biochemistry and molecular biology, and in particular to the field of enzymology and heparan sulfate biosynthesis.

BACKGROUND OF THE INVENTION

The serine proteases of the intrinsic blood coagulation cascade art slowly neutralized by antithrombin (AT) (reviewed in (1)). This inhibition is secondary to the generation of 1:1 enzyme-AT complexes whose formation is dramatically enhanced by the mast cell product, heparin (2). Damus et al. (3) hypothesized that endothelial cell surface heparan sulfate proteoglycans (HSPGs) function in a similar fashion to accelerate coagulation enzyme inactivation by AT, and therefore are responsible for the non-thrombogenic properties of blood vessels. It was initially demonstrated that profusion of the hindlimbs of normal rodents and rodents deficient in mast cells with purified thrombin (T) and AT leads to a greatly elevated rate of T-AT complex formation and that the enzyme heparitinase as well as the natural heparin antagonist platelet factor 4 suppress the above acceleration (4, 5). It was subsequently showed that cultured cloned bovine macrovascular and rodent microvascular endothelial cells synthesize both anticoagulant HSPG (HSPG$^{act}$) as well as nonanticoagulant HSPG (HSPG$^{inact}$) (6-14 8). HSPG$^{act}$ bear glycosaminoglycan (GAG) chains that bind tightly to AT and accelerate T-AT complex generation (6–8).

The biosynthesis of HSPG$^{act}$ requires generation of a core protein, assembly of a linkage region of four neutral sugars on specific serine attachment sites of the core protein, elongation of a GAG backbone composed of alternating N-acetylglucosamine and glucuronic acid residues, and modification of this homogenous copolymer by partial N-deacetylation with coupled N-sulfation of glucosamine residues, partial epimerization of glucuronic acid to iduronic acid residues, partial 2-O-sulfation of uronic acid residues, and partial 6-O-sulfation and partial 3-O-sulfation of glucosamine residues (reviewed in 9)). This multienzyme pathway generates HSPG$^{act}$ with regions of defined structure that contain the primary AT binding domain sequence found in anticoagulant heparin: uronic acid→glucosamine (N-acetyl/N-sulfate) 6-O-sulfate→glucuronic acid→glucosamine N-sulfate 3-O-sulfate (6-O-sulfate)→ iduronic acid 2-O-sulfate→glucosamine N-sulfate 6-O-sulfate (10–17). These reactions also produce HSPG$^{inact}$ with regions of varying monosaccharide sequence that lack the primary AT-binding domain. The structure-function relationships of the AT binding domain have been elucidated with heparin/heparan sulfate oligosaccharides in association with fast reaction kinetics and equilibrium binding assays. The 6-O-sulfate group on residue 2 and the 3-O-sulfate group on residue 4 function in a thermodynamically linked fashion to supply half of the binding energy for interaction with AT, and trigger a conformational event that accelerates neutralization of specific coagulation proteases (11, 12). The amino and ester sulfate groups at residues 5 and 6, as well as carboxyl groups at other sites, provide the other half of the binding energy for interaction with protease inhibitor (10, 11). Furthermore, monosaccharide sequences outside the primary AT binding domain are essential in facilitating inhibition of coagulation proteases other than factor Xa (18, 19).

During the past eight years, several biosynthetic enzymes that generate HSPG$^{act}$ and HSPG$^{inact}$ have been purified. These proteins include an N-acetylglucosamine/glucuronic acid copolymerase (20), N-deacetylase/N-sulfotransferases (NST-1 and NST-2) (21, 22), a glucuronic acid/iduronic acid epimerase (23), an iduronic acid/glucuronic acid 2-O-sulfotransferase (2-OST) (24), a glucosamine 6-O-sulfotransferase (6-OST) (25) and a glucosamine 3-O-sulfotransferase (3-OST) (26, 35). However, the only enzymes that have also been molecularly cloned are two structurally and functionally distinct isoforms of N-deacetylase/N-sulfotransferase (NST-1 from liver and NST-2 from mastocytoma) (27–31), and the 2-OST and epimerase. The above enzymes must function in a coordinated manner to produce the AT binding domain because the abundance of this sequence is much greater than predicted from a random assembly of constituents (32). The postulated regulatory mechanism must direct the biosynthetic enzymes to carry out the appropriate sequence of epimerization/sulfation reactions to generate the AT binding domain (33, 34).

SUMMARY OF THE INVENTION

The present invention depends, in part, upon the identification and molecular cloning of novel genes encoding mammalian heparan sulfate D-glucosaminyl 3-O-sulfotransferases (3-OSTs). In particular, as disclosed herein, the present invention provides nucleic acid (SEQ ID NO: 1) and amino acid (SEQ ID NO: 2) sequences for murine 3-OST-1; nucleic acid (SEQ ID NO: 3) and amino acid (SEQ ID NO: 4) sequences for human 3-OST-1; nucleic acid (SEQ ID NO: 5) and amino acid (SEQ ID NO: 6) sequences for human 3-OST-2; nucleic acid (SEQ ID NO: 7) and amino acid (SEQ ID NO: 8) sequences for human 3-OST-3A; nucleic acid (SEQ ID NO: 9) and amino acid (SEQ ID NO: 10) sequences for human 3-OST-3B; and nucleic acid (SEQ ID NO: 11) and amino acid (SEQ ID NO: 12) sequences for human 3-OST-4. In addition, the invention provides amino acid (SEQ ID NO: 15) sequences for a *C. elegans* homologue, ce3-OST.

Thus, in one aspect, the present invention provides isolated nucleic acids encoding at least a functional fragment of a 3-OST protein. In preferred embodiments, the nucleic acid encodes a 3-OST protein comprising a mature murine or human 3-OST-1. In other embodiments, the nucleic acid encodes a 3-OST protein selected from 3-OST-1, 3-OST-2, 3-OST-3A, 3-OST-3B, 3-OST-4, and ce3-OST. In other preferred embodiments, the nucleic acid encodes a 3-O-sulfotransferase domain of a 3-OST protein selected from 3-OST-1, 3-OST-2, 3-OST-3A, 3-OST-3B, 3-OST-4, and ce3-OST. In particular embodiments, the nucleic acid comprises a nucleotide sequence selected from nucleotide sequences within: (a) SEQ ID NO: 1; (b) SEQ ID NO: 3; (c) SEQ ID NO: 5; (d) SEQ ID NO: 7; (e) SEQ ID NO: 9; (f) SEQ ID NO: 11; (g) a sequence having at least 60% nucleotide sequence identity with at least one of (a)–(f) and encoding a functional fragment having sequence-specific HS binding affinity or 3-O-sulfotransferase activity; and (h) a sequence differing from a sequence of (a)–(g) only by the substitution of synonymous codons. In other particular embodiments, the present invention provides an isolated nucleic acid encoding a polypeptide selected from: (a) residues 21–52, 260–269, 250–276, 53–311, or 21–307 of SEQ ID NO: 2; (b) residues 21–48, 256–265, 246–272, 49–307, or 21–303 of SEQ ID NO: 4; (c) residues 42–109, 313–325, 303–332, or 110–367 of SEQ ID NO: 6; (d) residues 44–147, 351–363, 341–370, or 148–406 of SEQ ID NO: 8; (e) residues 66–132, 336–348, 326–355, or 133–390 of SEQ ID NO: 10; (f) residues 396–408, 386–415, or 207–456 of SEQ ID NO: 12; (g) residues 240–250, 230–257, 23–291 of SEQ ID NO: 15, (h) a sequence having at least 60% amino acid sequence similarity with at least one of (a)–(g) and encoding a functional fragment having sequence-specific HS binding affinity or 3-O-sulfotransferase activity; and (i) a sequence comprising a chimera of at least two of sequences (a)–(h).

In another aspect, the present invention provides isolated nucleic acids comprising at least 16 consecutive nucleotides of a nucleotide sequence selected from SEQ ID NO: 1, SEQ ID NO: 3, SEQ ID NO: 5, SEQ ID NO: 7, SEQ ID NO: 9, and SEQ ID NO: 11.

In another aspect, the present invention provides for cells and cell lines transformed with the nucleic acids of the present invention. Thus, the invention provides host cells transformed with any of the above-described nucleic acids. The transformed host cells may be bacterial, yeast, or insect cells. Preferably, however, the host cells are mammalian cells, including endothelial cells, mast cells, fibroblasts, hybridomas, oocytes, and embryonic stem cells. Examples of preferred mammalian cells include COS-7 cells, murine primary cardiac microvascular endothelial cells (CME), murine mast cell line C57.1, primary human endothelial cells of umbilical vein (HUVEC), F9 embryonal carcinoma cells, rat fat pad endothelial cells (RFPEC), L cells (e.g., murine LTA tk⁻ cells), and cells derived from the transgenic animals of the invention. The transformed host cells may also be fetal cells, embryonic stem cells, zygotes, gametes, or germ line cells. Transformed embryonic stem cells, zygotes, gametes, and germ line cells, as well as other mammalian cells, may be used to produce transgenic animals in which the expression of 3-OST genes have been altered (e.g., knock-outs, enhanced expression, ectopic expression).

In another aspect, the present invention provides substantially pure protein preparations comprising at least a functional fragment of a 3-OST protein. Thus, in one embodiment, the present invention provides a substantially pure protein preparation comprising mature murine 3-OST-1 or mature human 3-OST-1. In another embodiment, the 3-OST protein is selected from the group consisting of 3-OST-1, 3-OST-2, 3-OST-3A, 3-OST-3B, 3-OST-4, and ce3-OST. In another embodiment, the fragment comprises a 3-O-sulfotransferase domain of a 3-OST protein selected from the group consisting of 3-OST-1, 3-OST-2, 3-OST-3A, 3-OST-3B, 3-OST-4; and ce3-OST. In particular embodiments, the present invention provides a substantially pure protein preparation in which the 3-OST protein comprises an amino acid sequence selected from: (a) SEQ ID NO: 2; (b) SEQ ID NO: 4; (c) SEQ ID NO: 6; (d) SEQ ID NO: 8; (e) SEQ ID NO: 10; (f) SEQ ID NO: 12; (g) SEQ ID NO 15; and (h) a sequence having at least 60% amino acid similarity with at least one of (a)–(g) and having sequence-specific HS binding affinity or 3-O-sulfotransferase activity. In other particular embodiments, the present invention provides a substantially pure protein preparation in which the 3-OST protein comprises an amino acid sequence selected from: (a) residues 21–52, 260–269, 250–276, 53–311, or 21–307 of SEQ ID NO: 2; (b) residues 21–48, 256–265, 246–272, 49–307, or 21–303 of SEQ ID NO: 4; (c) residues 42–109, 313–325, 303–332, or 110–367 of SEQ ID NO: 6; (d) residues 44–147, 351–363, 341–370, or 148–406 of SEQ ID NO: 8; (e) residues 66–132, 336–348, 326–355, or 133–390 of SEQ ID NO: 10; (f) residues 396–408, 386–415, or 207–456 of SEQ ID NO: 12; (g) residues 240–250, 230–257, 23–291 of SEQ ID NO: 15; (h) a sequence having at least 60% amino acid sequence similarity with at least one of (a)–(g) and encoding a functional fragment having sequence-specific HS binding affinity or 3-O-sulfotransferase activity; and (i) a sequence comprising a chimera of at least two of sequences (a)–(h).

In another aspect, the present invention provides for antibodies and methods for making antibodies which selectively bind with the 3-OST proteins. These antibodies include monoclonal and polyclonal antibodies, as well as functional antibody fragments such as F(ab) and Fc.

In another aspect, the present invention provides for methods for producing the above-described proteins. Thus, in one set of embodiments, the isolated nucleic acids of the invention may be used to transform host cells or create transgenic animals which express the proteins of the invention. The proteins may then be substantially purified from the cells or animals by standard methods. Alternatively, the isolated nucleic acids of the invention may be used in cell-free in vitro translation systems to produce the proteins of the invention.

In another aspect, the present invention provides methods for 3-O-sulfating saccharide residues within a preparation of glycosaminoglycan or proteoglycan polysaccharides by contacting the preparation with at least a 3-O-sulfotransferase domain of a 3-OST protein in the presence of a sulfate donor under conditions which permit sulfation of the residues, and wherein the 3-OST protein is selected from 3-OST-1, 3-OST-2, 3-OST-3A, 3-OST-3B, 3-OST-4, and ce3-OST proteins, as well as conservative substitution variants and/or chimeras thereof. In particular embodiments, the present invention provides methods for 3-O-sulfating saccharide residues within a preparation of glycosaminoglycan or proteoglycan polysaccharides in which the polysaccharides include a polysaccharide sequence of GlcA→GlcNS±6S. These methods comprise contacting the GlcA→GlcNS±6S-containing polysaccharide preparation with a 3-OST-1 protein in the presence of a sulfate donor under conditions which permit the 3-OST-1 to convert the GlcA→GlcNS±6S sequence to GlcA→GlcNS 3S±6S. In particular embodiments, the GlcA→GlcNS±6S sequence comprises a part of an HS$^{act}$ precursor sequence (i.e., IdoA→GlcNAc 6S→GlcA→GlcNS±6S→IdoA 2S→GlcNS 6S or IdoA→GlcNS 6S→GlcA→GlcNS±6S→IdoA 2S→GlcNS 6S) or a part of an HS$^{inact}$ precursor sequence (i.e., IdoA→GlcNAc→GlcA→GlcNS±6S→IdoA 2S→GlcNS 6S; IdoA→GlcNS→GlcA→GlcNS±6S→IdoA 2S→GlcNS 6S; IdoA→GlcNAc 6S→GlcA→GlcNS±6S→IdoA 2S→GlcNS; or IdoA→GlcNS 6S→GlcA→GlcNS±6S→IdoA 2S→GlcNS). Conversion of the HS$^{act}$ precursor pool to HS$^{act}$ increases the fraction with AT-binding activity and is particularly useful in the production of anticoagulant heparan sulfate products. Thus, in another embodiment, the present invention provides for means of enriching the AT-binding fraction of a heparan sulfate pool by contacting the polysaccharide preparation with 3-OST-1 protein in the presence of a sulfate donor under conditions which permit the 3-OST HS$^{act}$ conversion activity. The 3-OST-1 protein for use in these methods is selected from murine 3-OST-1, human 3-OST-1, mature murine 3-OST-1, mature human 3-OST-1, a functional fragment of a 3-OST-1 having 3-O-sulfotransferase activity, a conservative substitution variant of 3-OST-1 having 3-O-sulfotransferase activity, and a chimeric 3-OST-1 having 3-O-sulfotransferase activity. In preferred embodiments, the sulfate donor is 3'-phospho-adenosine 5'-phosphosulfate (PAPS).

Similarly, the present invention provides methods for 3-O-sulfating saccharide residues within a preparation of glycosaminoglycan or proteoglycan polysaccharides by contacting the preparation with at least a 3-O-sulfotransferase domain of a 3-OST protein in the presence of a sulfate donor under conditions which permit sulfation of the residues, and wherein the 3-OST protein is selected from 3-OST-2, 3-OST-3A, 3-OST-3B, 3-OST-4, ce3-OST and conservative substitution variants or chimeras thereof. In particular embodiments, the present invention provides methods for 3-O-sulfating saccharide residues within a preparation of glycosaminoglycan or proteoglycan polysaccharides in which the polysaccharides include a polysaccharide sequence of GlcA 2S→GlcNS. These methods comprise contacting the GlcA 2S→GlcNS-containing polysaccharide preparation with a 3-OST-2 protein in the presence of a sulfate donor under conditions which permit the 3-OST-2 protein to convert the GlcA 2S→GlcNS sequence to GlcA 2S→GlcNS 3S. In particular embodiments, the GicA 2S→GlcNS sequence comprises a part of a GlcNS→GlcA 2S→GlcNS sequence. In other particular embodiments, the present invention provides methods for 3-O-sulfating saccharide residues within a preparation of glycosaminoglycan or proteoglycan polysaccharides in which the polysaccharides include a polysaccharide sequence of IdoA 2S→GlcNS. These methods comprise contacting the IdoA 2S→GlcNS-containing polysaccharide preparation with a 3-OST-3 protein in the presence of a sulfate donor under conditions which permit the 3-OST-3 protein to convert the IdoA 2S→GlcNS sequence to IdoA 2S→GlcNS 3S. In particular embodiments, the IdoA 2S→GlcNS sequence comprises a part of a GlcNS→IdoA 2S→GlcNS sequence. The 3-OST proteins for use in these methods are selected from 3-OST-2, 3-OST-3A, 3-OST-3B, 3-OST-4ce3-OST, functional fragments of these 3-OSTs having 3-O-sulfotransferase activity, conservative substitution variants of these 3-OSTs having 3-O-sulfotransferase activity, and chimeric 3-OSTs having 3-O-sulfotransferase activity. In preferred embodiments, the sulfate donor is 3'-phospho-adenosine 5'-phosphosulfate (PAPS).

In another aspect, the present invention provides methods for partially sequencing complex polysaccharides such as heparan sulfates or other glycosaminoglycans (GAGs). In these methods, a pool of polysaccharides which includes sequences which may be 3-O-sulfated is contacted with a 3-OST protein in the presence of a sulfate donor (e.g., PAPS) under conditions which permit sulfation by the 3-OST. The treated polysaccharides are then subjected to degradation by enzymes which degrade polysaccharides in a sequence-specific manner (e.g., polysaccharide lyases; heparinase I, II or III; heparitinase) and the size profile of the resulting fragments is determined. An identical pool which has not been treated with 3-OST is similarly cleaved by the same enzymes and a size profile determined. Changes in the size profiles indicate that 3-OST activity has modified the saccharide units so as to prevent (or permit) cleavage at sites which previously were (or were not) cleaved. Thus, comparison of the profiles will indicate positions at which the target sequences for 3-OST activity are present and provide a partial polysaccharide sequence.

In another embodiment, the sequence of complex polysaccharides such as HS or GAGs may be partially determined using sequence specific polysaccharide affinity fractionation. To this end, 3-OST proteins which lack enzymatic function but retain sequence-specific HS or GAG binding capacity can be identified or produced (e.g., altering or deleting a portion of the catalytic ST domain by site-directed mutagenesis or deletion mutagenesis). These inactive forms will bind HS or GAGs in a sequence dependent manner and allow sequence-specific saccharide affinity fractionation from complex mixtures of GAGs. The purified structures may be degraded in a step-wise fashion with exolytic, endolytic enzymes and/or nitrous acid, and the resulting degradation products can be compared to standard compounds of known structure. This method will allow the quantitation and characterization of known structures contained within unknown complex polysaccharide samples.

In another embodiment, partial sequence information can be obtained using the 3-OSTs of the invention or other heparan sulfate sequence specific binding ligands as protective groups prior to treating the HS or GAG with modifying agents that detectably alter the HS or GAG. Useful protective groups include catalytically inactive enzymes, chimeric enzymes and small molecule ligands with identified sequence binding specificities. The protecting group is contacted with the heparan or other glycosaminoglycans (GAGs), and the resultant complex is treated with one or more modifying agents. Useful modifying agents include catalytically active heparan lyases, sulfotransferases, N-deacetylases, N-acetyltransferases, epimerases, or chimeric proteins of the invention. In embodiments where multiple protecting groups and/or modifying reagents are used in combination, the sample is first contacted with the protective group, then one or more modifying reagents may be with contacted with the protected polysaccharide, either simultaneously or in turn. The protective group(s) will interfere with the ability of a modifying agent to interact with, attach to and/or cleave specific GAG sequence motifs. The sample can then be analyzed for ligand-specific protection and/or cleavage to elucidate the sequence of the original GAG using separation and/or quantitation using methods known in the art.

In another aspect, the present invention also provides methods for diagnosing individuals with disorders involving heparan sulfate biosynthesis comprising assaying such individuals for the presence of mutations in 3-OST genes/proteins. Such assays include nucleic acid based assays (employing the nucleic acids of the present invention), protein based assays (employing the antibodies of the present invention), and HS based assays employing the glycosaminoglycan sequencing methods of the present invention.

These and other aspects of the present invention will be apparent to one of ordinary skill in the art from the following detailed description.

BRIEF DESCRIPTION OF THE DRAWINGS

FIG. 1 is an alignment of the amino acid sequences of murine and human 3-OST-1 proteins (SEQ ID NO: 2 and 4, respectively), showing the degree of homology. Vertical bars (|) between residues indicate identical residues.

FIG. 2 is an alignment of the sulfotransferase domains of human NST-1 (SEQ ID NO: 13), human NST-2 (SEQ ID NO: 14), *C. elegans* (residues 23–291 of SEQ ID NO: 15), human 3-OST-4 (residues 193–456 of SEQ ID NO: 12), human 3-OST-3A (residues 148–406 of SEQ ID NO: 8), human 3-OST-2 (residues 110–367 of SEQ ID NO: 6) and human 3-OST-1 (residues 49–307 of SEQ ID NO: 4).

DETAILED DESCRIPTION OF THE INVENTION

Definitions

Figure 3:
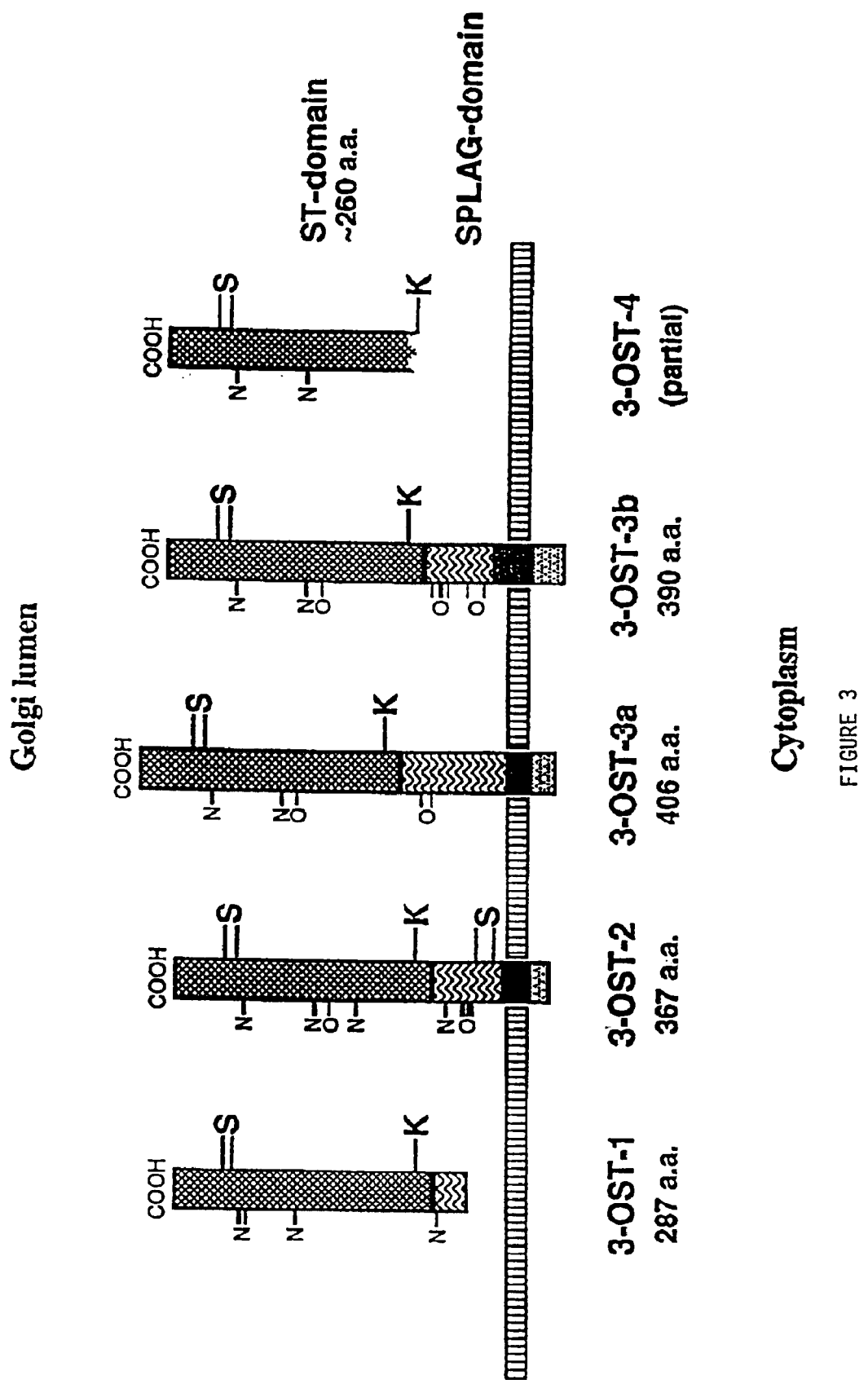
FIG. 3 is a schematic depiction of the structures of the 3-OST-1, 3-OST-2, 3-OST-3A, 3-OST-3B and 3-OST-4 proteins.

In order to more clearly and distinctly point out and describe the subject matter that applicants regard as the invention, the following definitions are provided for certain terms used in the following written description and the appended claims.

Isolated nucleic acids. As used herein with respect to nucleic acids derived from naturally-occurring sequences, the term "isolated nucleic acid" means a ribonucleic or deoxyribonucleic acid which comprises a naturally-occurring nucleotide sequence and which is manipulable by standard recombinant DNA techniques, but which is not covalently joined to the nucleotide sequences that are immediately contiguous on its 5' and 3' ends in the naturally-occurring genome of the organism from which it is derived. As used herein with respect to synthetic nucleic acids, the term "isolated nucleic acid" means a ribonucleic or deoxyribonucleic acid which comprises a nucleotide sequence which does not occur in nature and which is manipulable by standard recombinant DNA techniques. An isolated nucleic acid is manipulable by standard recombinant DNA techniques when it may be used in, for example, amplification by polymerase chain reaction (PCR), in vitro translation, ligation to other nucleic acids (e.g., cloning or expression vectors), restriction from other nucleic acids (e.g., cloning or expression vectors), transformation of cells, hybridization screening assays, or the like. The term "isolated nucleic acids" is also intended to embrace synthetic oligonucleotides such as peptide nucleic acids (PNAs), nucleotides joined by phosphorothioate or other non-phosphodiester linkages, nucleic acids incorporating functionally equivalent nucleotide analogs, and the like.

Transformation As used herein, means any method of introducing exogenous a nucleic acid into a cell including, but not limited to, transformation, transfection, electroporation, microinjection, direct injection of naked nucleic acid, particle-mediated delivery, viral-mediated transduction or any other means of delivering a nucleic acid into a host cell which results in transient or stable expression of said nucleic acid or integration of said nucleic acid into the genome of said host cell or descendant thereof.

Substantially pure. As used herein with respect to protein preparations, the term "substantially pure" means a preparation which contains at least 60% (by dry weight) the protein of interest, exclusive of the weight of other intentionally included compounds. Preferably the preparation is at least 75%, more preferably at least 90%, and most preferably at least 99%, by dry weight the protein of interest, exclusive of the weight of other intentionally included compounds. Purity can be measured by any appropriate method, e.g., column chromatography, gel electrophoresis, or HPLC analysis. If a preparation intentionally includes two or more different proteins of the invention, a "substantially pure" preparation means a preparation in which the total dry weight of the proteins of the invention is at least 60% of the total dry weight, exclusive of the weight of other intentionally included compounds. Preferably, for such preparations containing two or more proteins of the invention, the total weight of the proteins of the invention be at least 75%, more preferably at least 90%, and most preferably at least 99%, of the total dry weight of the preparation, exclusive of the weight of other intentionally included compounds. Thus, if the proteins of the invention are mixed with one or more other proteins (e.g., serum albumin, 6-OST) or compounds (e.g., diluents, detergents, excipients, salts, polysaccharides, sugars, lipids) for purposes of administration, stability, storage, and the like, the weight of such other proteins or compounds is ignored in the calculation of the purity of the preparation.

Similarity. As used herein with respect to amino acid sequences, the "similarity" between two sequences means the percentage of amino acid residue positions, after aligning the sequences according to standard techniques, at which the two sequences have identical or similar residues. In general, "similar" residues include those which are regarded in the art as "conservative substitutions" (see, e.g., Dayhoff et al. (1978), *Atlas of Protein Sequence and Structure* Vol. 5 (Suppl. 3), pp. 354–352, Natl. Biomed. Res. Found., Washington, D.C.); which fall within the groups (a) methionine, leucine, isoleucine and valine, (b) phenylalanine, tyrosine and tryptophan, (c) lysine, arginine and histidine, (d) alanine and glycine. (e) serine and threonine, (f) glutamine and asparagine. and (g) glutamate an aspartate; or which are otherwise shown to have no substantial effect on the biological activity of the protein. Numerical values for similarity were determined using the PileUp program. This program performed multiple sequence alignments based on methods of Feng and Doolittle (1987) *J. Mol. Evol.* 35: 351–360, and Higgins and Sharp (1998), *CABIOS* 5:151–153. Using these methods for each sequence alignment, the gap weight was set at 3.0 and the gap length was set at 0.10. Percentages of similarity recited in the appended claims may be determined by these methods.

Chimeric protein. As used herein, the term "chimeric protein" means a protein having an amino acid sequence which is a positionally conserved combination of the amino acid sequences of two or more other proteins. Thus, for a chimera of two or more reference proteins, the amino acid sequences of the reference proteins are aligned by standard techniques to identify residues which correspond at each position, allowing for relative insertions/deletions as necessary. Then, for each amino acid position of the chimeric protein, an amino acid residue is selected from the residues present at corresponding positions in the two or more reference proteins (allowing for no residue in the chimera when deletions are present amongst the reference proteins). The resultant chimera has an amino acid sequence which is a combination of the reference amino acid sequences, in which the relative position of each residue selected from the reference sequences is conserved within the chimera.

Heparan sulfate. As used herein, the term "heparan sulfate" or the abbreviation "HS" means a polysaccharide of the form ([→4-D-GlcAp$\beta$1 or →4-L-IdoAp$\alpha$1]→4-D-GlcNp[Ac or S]$\alpha$1→)$_n$ which is modified to a variable extent by sulfation of the 2-O-position of Glc and Ido residues, and the 6-O- and 3-O-positions of GlcN[Ac or S] residues. Therefore, this definition encompasses all glycosaminoglycan compounds referred to as heparan(s), heparan sulfate(s), heparin(s), heparin sulfate(s), heparitin(s), heparitin sulfate(s), heparanoid(s), heparosan(s). The heparan molecules may be pure glycosaminoglycans or can be linked to other molecules including other polymers such as proteins, and lipids, or small molecules such as biotin.

The Heparan Sulfate D-Glucosaminyl 3-O-Sulfotransferaseses. The present invention depends, in part, upon the identification and molecular cloning of cDNAs encoding mammalian heparan sulfate D-glucosaminyl 3-O-sulfotransferases (3-OSTs). These proteins have been designated 3-OST-1, 3-OST-2, 3-OST-3A, 3-OST-3B, and 3-OST-4. In addition, a nematode 3-OST from *C. elegans*, ce3-OST, has been identified.

3-OST-1s. Disclosed herein are the isolation and identification of murine and human 3-OST-1 cDNAs (SEQ ID NO: 1 and SEQ ID NO: 3, respectively). The coding regions of these cDNAs extend from, respectively, nucleotide positions 323–1255 of SEQ ID NO: 1 and positions 119–1039 of SEQ ID NO: 3. The protein coding portions of the cDNAs are 85% identical and encode proteins of 311 and 307 amino acids (SEQ ID NO: 2 and SEQ ID NO: 4, respectively) which are 93% similar. The murine and human protein sequences are aligned in FIG. 1. Each protein includes a twenty residue presumptive signal peptide (residues 1–20 of SEQ ID NO: 2 and SEQ ID NO: 4) which is cleaved off to form the mature form of these proteins. The mouse 3-OST-1 contains an extra four residues ($Ala^{24}$-$Pro^{25}$-$Gly^{26}$-$Pro^{27}$) not found in the human form. Each protein has five potential N-glycosylation sites (at residues 52–54, 141–143, 196–198, 246–248 and 253–255 of SEQ ID NO: 2, and residues 48–50, 137–139, 192–194, 242–244, 249–251 of SEQ ID NO: 4). N-glycosylation of at least some of these sites appears important to 3-OST protein stability, specificity and/or activity. After the 3-OST-1 signal peptide, there is a domain rich in the residues S, P, L, A, and G (SPLAG-rich domain) (residues 21–52 of SEQ ID NO: 2 and residues 21–48 of SEQ ID NO: 4). 3-OST-1 and all known NST species possess a homologous carboxy terminal sulfotransferase (ST) domain of ~260 amino acids (residues 53–311 of SEQ ID NO: 2 and residues 49–307 of SEQ ID NO: 4) that exhibits homology to all known sulfotransferases and which includes the minimal fragment necessary for sulfation activity. FIG. 2 shows a sequence alignment of the ST domains of the sulfotransferases NST-1 (SEQ ID NO: 13), NST-2 (SEQ ID NO: 14), OST-1, OST-2, OST-3A/B, and OST-4. Within this region is a conserved sequence (at residues 260–269 of SEQ ID NO: 2, and 256–265 of SEQ ID NO: 4) which is a presumptive cysteine-bridged peptide loop thought to be involved in heparan sulfate substrate specificity. This cysteine-bridged peptide loop is part of the larger HS-binding domain (residues 250–276 of SEQ ID NO: 2 and 246–272 of SEQ ID NO: 4). A conserved lysine residue (residue 68 of SEQ ID NO: 2, and 64 of SEQ ID NO: 4) is presumptively catalytic.

The 3-OST-1 proteins have 3-O-sulfotransferase activity on polysaccharide sequences including the sequence GlcA→GlcNS±6S, and convert this polysaccharide sequence to the sequence to GlcA→GlcNS 3S±6S. Of particular importance, the 3-OST-1 proteins are useful in converting $HS^{act}$ precursor sequences (i.e., IdoA→GlcNAc 6S→GlcAGlcNS±6S→IdoA 2S→GlcNS 6S; or IdoA→GlcNS 6S→GlcA→GlcNS±6S→IdoA 2S→GlcNS 6S) to $HS^{act}$. The 3-OST-1 proteins are highly expressed in endothelial cells, brain and kidney tissues, and to a lesser extent in heart, lung, skeletal muscle and placenta. The human 3-OST-1 gene has been syntactically localized to chromosome 4, and more particularly to chromosome segment 4p 15–16.

3-OST-2s. Also disclosed herein are the isolation and identification of a human 3-OST-2 cDNA (SEQ ID NO: 5). The coding region of this cDNA extends from nucleotide positions 73–1173 of SEQ ID NO: 5. The cDNA encodes a protein of 367 amino acids (SEQ ID NO: 6). The protein has four potential N-glycosylation sites (at residues 102–104, 193–195, 235–237 and 306–308 of SEQ ID NO: 6). N-glycosylation of at least some of these sites appears important to 3-OST protein stability, specificity and/or activity. The 3-OST-2 protein has a putative N-terminal cytoplasmic domain (residues 1–19 of SEQ ID NO: 6), followed by a putative transmembrane domain (residues 20–41 of SEQ ID NO: 6), followed by a SPLAG-rich domain (residues 42–109 of SEQ ID NO: 6). This is followed by the characteristic carboxy terminal ST domain of ~260 amino acids (residues 110–367 of SEQ ID NO: 6) that exhibits homology to all known sulfotransferases and which includes the minimal fragment necessary for sulfation activity. Within this region is a conserved sequence (at residues 313–325 of SEQ ID NO: 6) which is a presumptive cysteine-bridged peptide loop thought to be involved in heparan sulfate substrate specificity. This cysteine-bridged peptide loop is part of the larger HS-binding domain (residues 303–332 of SEQ ID NO: 6). A conserved lysine residue (residue 24 of SEQ ID NO: 6) is presumptively catalytic. A cDNA of an allelic variant has also been identified, which includes four silent nucleotide substitutions (G→A at bp 804, T→G at bp 1249, T→C at bp 1350, and C→T at bp 1507 of SEQ ID NO: 5) which do not affect the encoded protein.

The 3-OST-2 proteins have 3-O-sulfotransferase activity on polysaccharide sequences including the sequences GlcA 2S→GlcNS or GlcNS→GlcA 2S→GlcNS, and convert these polysaccharide sequences to GlcA 2S→GlcNS 3S or GlcNS→GlcA 2S→GlcNS 3S, respectively. The 3-OST-2 proteins are not expressed in endothelial cells, but are highly expressed in brain tissues, and to a lesser extent in heart, lung, skeletal muscle and placenta. The human 3-OST-2 gene has been localized to chromosome 16, and more particularly to chromosome segment 16p12.3.

3-OST-3As. Also disclosed herein are the isolation and identification of a human 3-OST-3A cDNA (SEQ ID NO: 7). The coding region of this cDNA extends from nucleotide positions 799–2016 of SEQ ID NO: 7. The cDNA encodes a protein of 406 amino acids (SEQ ID NO: 8). The protein has two potential N-glycosylation sites (at residues 273–275 and 344–346 of SEQ ID NO: 8). N-glycosylation of one or more of these sites appears important to 3-OST protein stability, specificity and/or activity. The 3-OST-3A protein has a putative N-terminal cytoplasmic domain (residues 1–24 of SEQ IDNO: 8), followed by a putative transmembrane domain (residues 25–43 of SEQ ID NO: 8), followed by a SPLAG-rich domain (residues 44–147 of SEQ ID NO: 8). This is followed by the characteristic carboxy terminal ST domain of ~260 amino acids (residues 148–406 of SEQ ID NO: 8) that exhibits homology to all known sulfotransferases and which includes the minimal fragment necessary for sulfation activity. Within this region is a conserved sequence (at residues 351–363 of SEQ ID NO: 8) which is a presumptive cysteine-bridged peptide loop thought to be involved in heparan sulfate substrate specificity. This cysteine-bridged peptide loop is part of the larger HS-binding domain (residues 341–370 of SEQ ID NO: 8). A conserved lysine residue (residue 162 of SEQ ID NO: 8) is presumptively catalytic.

The 3-OST-3A proteins have 3-O-sulfotransferase activity on polysaccharide sequences including the sequences IdoA 2S→GlcNS or GlcNS→IdoA 2S→GlcNS, and convert these polysaccharide sequences to IdoA 2S→GlcNS 3S or GlcNS→IdoA 2S→GlcNS 3S, respectively. The 3-OST-3A proteins are not expressed in endothelial cells, but are highly expressed in kidney, placenta and liver tissues, and to a lesser extent in brain, heart, lung, and skeletal muscle.

3-OST-3Bs. Also disclosed herein are the isolation and identification of a human 3-OST-3B cDNA (SEQ ID NO: 9). The coding region of this cDNA extends from nucleotide positions 331–1500 of SEQ ID NO: 9. The cDNA encodes a protein of 390 amino acids (SEQ ID NO: 10). The protein has two potential N-glycosylation sites (at residues 258–260 and 329–331 of SEQ ID NO: 10). N-glycosylation of one or more of these sites appears important to 3-OST protein stability, specificity and/or activity. The 3-OST-3B protein has a putative N-terminal cytoplasmic domain (residues 1–32 of SEQ ID NO: 10), followed by a putative transmembrane domain (residues 33–65 of SEQ ID NO: 10), followed by a SPLAG-rich domain (residues 66–132 of SEQ ID NO: 10). This is followed by the characteristic carboxy terminal ST domain of ~260 amino acids (residues 133–390 of SEQ ID NO: 10) that exhibits homology to all known sulfotransferases and which includes the minimal fragment necessary for sulfation activity. Within this region is a conserved sequence (at residues 336–348 of SEQ ID NO: 10) which is a presumptive cysteine-bridged peptide loop thought to be involved in heparan sulfate substrate specificity. This cysteine-bridged peptide loop is part of the larger HS-binding domain (residues 326–355 of SEQ ID NO: 10). A conserved lysine residue (residue 147 of SEQ ID NO: 10) is presumptively catalytic.

The 3-OST-3B proteins have 3-O-sulfotransferase activity on polysaccharide sequences including the sequences IdoA 2S→GlcNS or GlcNS→IdoA 2S→GlcNS, and convert these polysaccharide sequences to IdoA 2S→GlcNS 3S or GlcNS→IdoA 2S→GlcNS 3S, respectively. The 3-OST-3A proteins are not expressed in endothelial cells, but are highly expressed in kidney, placenta and liver tissues, and to a lesser extent in brain, heart, lung, and skeletal muscle.

3-OST-4s. Also disclosed herein are the isolation and identification of a human 3-OST-4 nucleic acid sequence (SEQ ID NO: 11). This sequence represents is a possible or predicted heteronuclear RNA species, and is a composite of 5' genomic sequences information and an overlapping partial cDNA. The coding region of this sequence extends from nucleotide positions 847–2214 of SEQ ID NO: 11, and encodes a protein of 456 amino acids (SEQ ID NO: 12). The protein has two potential N-glycosylation sites (at residues 318–320 and 389–391 of SEQ ID NO: 12). N-glycosylation of one or more of these sites appears important to 3-OST protein stability, specificity and/or activity. The 3-OST-4 includes the characteristic carboxy terminal ST domain of ~260 residues (residues 207–456 of SEQ ID NO: 12) that exhibits homology to all known sulfotransferases and which includes the minimal fragment necessary for sulfation activity. Within this region is a conserved sequence (at residues 396–408 of SEQ ID NO: 12) which is a presumptive cysteine-bridged peptide loop thought to be positioned near the active site. This cysteine-bridged peptide loop is part of the larger HS-binding domain (residues 386–415 of SEQ ID NO: 12). A conserved lysine residue (residue 207 of SEQ ID NO: 12) is presumptively catalytic.

The 3-OST-4 proteins have sulfotransferase activity, but the sequence specificity of this activity has not yet been determined. The 3-OST-4 proteins appear to be expressed at detectable levels only in the brain. The human 3-OST-4 gene has been localized to chromosome 16, and more particularly to chromosome segment 16p11.

C. elegans 3-OSTs. Also disclosed herein is the identification of a C. elegans homologue of the human 3-OSTs, ce3-OST. This protein is disclosed as SEQ ID NO: 15, and includes the characteristic carboxy terminal ST domain of ~260 residues (residues 23–291 of SEQ ID NO: 15) that exhibits homology to all known sulfotransferases and which includes the minimal fragment necessary for sulfation activity. Within this region is a conserved sequence (at residues 240–250 of SEQ ID NO: 15) which is a presumptive cysteine-bridged peptide loop thought to be positioned near the active site. This cysteine-bridged peptide loop is part of the larger HS-binding domain (residues 230–257 of SEQ ID NO: 15). A conserved lysine residue (residue 38 of SEQ ID NO: 15) is presumptively catalytic.

The C. elegans 3-OST proteins have sulfotransferase activity, but the sequence specificity of this activity has not yet been determined. BLAST and Genefinder anaysis of genomic cosmids predicts that ce3-OST is an intraluminal resident protein of 291 residues encoded by 4 exons (clone F52B10, Gban U41990; residues 26317–26090, 21886–21732, 21682–21395, and 21345–21140).

The homology between the sulfotransferase domain of the ce3-OST and the human 3-OST and NST proteins is illustrated in FIG. 2. BAsed on this sequence alignment, one may also produce chimeric proteins between and the C elegans protein and its human homologues.

Isolated Nucleic Acids

In one aspect, the present invention provides isolated nucleic acids encoding 3-OST proteins or functional fragments thereof. In preferred embodiments, the 3-OST proteins are 3-OST-1 proteins, 3-OST-2 proteins, 3-OST-3A proteins, 3-OST-3B proteins, 3-OST-4 proteins, or ce3-OST proteins. In particularly preferred embodiments, the 3-OST proteins are those disclosed as SEQ ID NO: 2, SEQ ID NO: 4, SEQ ID NO: 6, SEQ ID NO: 8, SEQ ID NO: 10, SEQ ID NO: 12, or SEQ ID NO: 15. As shown in the examples below, the isolated nucleic acids encoding all or a portion of one mammalian 3-OST protein may be used to isolate homologues in other species by standard techniques known to those of ordinary skill in the art. Thus, the present invention also enables isolated nucleic acids encoding the 3-OST proteins of other mammalian species including, for example, rats, goats, sheep, cows, pigs, and non-human primates. Similarly, the isolated nucleic acids disclosed herein may be used to screen additional human or other mammalian genetic libraries (e.g., genomic or cDNA libraries) to identify allelic variants of the particularly disclosed sequences. Thus, the present invention also enables isolated nucleic acids encoding human and other mammalian 3-OST allelic variants.

In another aspect, the present invention provides isolated nucleic acids encoding functional fragments of 3-OST proteins, 3-OST protein variants in which conservative substitutions have been made for certain residues, or encoding chimeric 3-OST proteins in which the sequences of two or more 3-OST proteins have been mixed, to produce non-naturally occurring variants which retain sequence-specific HS binding affinity and/or 3-O-sulfotransferase activity. The preferred amino acid sequences of such variants are described below.

In preferred embodiments, the isolated nucleic acids encoding a mammalian 3-OST or functional fragment thereof have at least 60%, preferably at least 70%, and more preferably at least 80% nucleotide sequence identity to the coding regions of the mammalian 3-OST sequences particularly disclosed herein (SEQ ID NO: 1, SEQ ID NO: 3, SEQ ID NO: 5, SEQ ID NO: 7, SEQ ID NO: 9 and SEQ ID NO: 11), and encode at least a functional fragment having sequence-specific HS binding affinity and/or 3-O-sulfotransferase activity. Most preferably, the sequences have at least 90% or 95% nucleotide sequence identity to the disclosed reference sequences.

As will be apparent to one of ordinary skill in the art, the degeneracy of the genetic code allows for numerous nucleotide substitutions in a given coding sequence which do not affect the amino acid sequence of the encoded protein. Thus, the present invention also provides for isolated nucleic acids which differ from any of the above-described sequences only by the substitution of such synonymous codons.

The isolated nucleic acids of the present invention may be joined to other nucleic acid sequences for use in various applications. Thus, for example, the isolated nucleic acids of the invention may be ligated into cloning or expression vectors, as are commonly known in the art and as described in the examples below. In addition, the nucleic acids of the invention may be joined in-frame to sequences encoding another polypeptide so as to form a fusion protein, as is commonly known in the art and as described in the examples below. Thus, in certain embodiments, the present invention provides cloning, expression and fusion vectors comprising any of the above-described nucleic acids.

In another aspect, the isolated nucleic acids of the present invention may comprise only a portion of a nucleotide sequence encoding a complete mammalian 3-OST protein. For example, and as described more fully below, the 3-OST-1 proteins comprise a signal sequence which is removed post-translationally to yield the mature proteins. In some instances (e.g., when translating 3-OST-1 proteins in vitro), it may be preferable to employ an isolated nucleic acid which encodes only the mature protein. In addition, the four C-terminal residues of 3-OST-1 are believed to be involved in localization of the protein within the Golgi apparatus. In some instances (e.g., when encoding 3-OST-1 proteins for use in vitro), it may be preferable to employ an isolated nucleic acid which does not encode these residues, as they will be unnecessary for in vitro function. As described above, an approximately 260 residue portion of the 3-OST proteins includes the catalytically active region (ST domain) and, therefore, it may be preferable to employ an isolated nucleic acid which encodes only this functional fragment which retains 3-O-sulfotransferase activity. Thus, in certain preferred embodiments, the present invention provides isolated nucleic acid sequences encoding mature forms of a mammalian 3-OST-1 protein, C-terminally truncated forms of the 3-OST proteins, or minimal functional fragments of the 3-OST proteins. In addition, as described above, these sequences may also encode conservative substitution variants or chimeras of 3-OST proteins, and may include synonymous codon substitutions.

In another aspect, the present invention provides for nucleic acids which comprise a sequence of at least 16–18, preferably 18–20 consecutive nucleotides from any one of SEQ ID NO: 1, SEQ ID NO: 3, SEQ ID NO: 5, SEQ ID NO: 7, SEQ ID NO: 9 and SEQ ID NO: 11. Such nucleic acid sequences have utility for determining the levels of expression of 3-OST transcripts in cells or tissues, for identifying tissues in which the 3-OST genes are differentially expressed (see above), for encoding peptide fragments which may be used to raise antibodies to corresponding regions of the 3-OST proteins, identifying chromosomes bearing the corresponding 3-OST sequences (see above), for priming polymerase chain reaction amplification of 3-OST sequences (e.g., prior to in vitro translation, see below), and for various other utilities which will be apparent to those skilled in the art. Particularly preferred sequences for PCR amplification include those which are 5' to and/or include the initiation codon, which are 5' to and/or include the codons encoding the signal peptide cleavage site, or which are 3' to and/or include the termination codon. Sequences useful for encoding peptide fragments include those which are located within the coding region.

Cell Lines and Transgenic Animals

The present invention also provides for cells or cell lines, both prokaryotic and eukaryotic, into which have been introduced the nucleic acids of the present invention so as to cause clonal propagation of those nucleic acids and/or expression of the proteins or peptides encoded thereby. Such cells or cell lines have utility in the propagation and production of the nucleic acids of the invention, as well as the production of the proteins of the present invention. As used herein, the term "transformed cell" is intended to embrace any cell, or the descendant of any cell, into which has been introduced any of the nucleic acids of the invention, whether by transformation, transfection, transduction, infection, or other means. Methods of producing appropriate vectors, transforming cells with those vectors, and identifying transformants are well known in the art and are only briefly reviewed here (see, for example, Sambrook et al. (1989) *Molecular Cloning: A Laboratory Manual*, 2nd ed., Cold Spring Harbor Laboratory Press, Cold Spring Harbor, N.Y.).

Prokaryotic cells useful for producing the transformed cells of the invention include members of the bacterial genera *Escherichia* (e.g., *E. coli*), *Pseudomonas* (e.g., *P. aeruginosa*), and *Bacillus* (e.g., *B. subtiilus, B. stearolhermophilus*), as well as many others well known and frequently used in the art. Prokaryotic cells are particularly useful for the production of large quantities of the proteins or peptides of the invention (e.g., naturally occurring or synthetic 3-OSTs, fragments of the 3-OSTs, fusion proteins of the 3-OSTs). Bacterial cells (e.g., *E. coli*) may be used with a variety of expression vector systems including, for example, plasmids with the T7 RNA polymerase/promoter system, bacteriophage λ regulatory sequences, or M13 Phage regulatory elements. Bacterial hosts may also be transformed with fusion protein vectors which create, for example, Protein A, lacZ, trpE, maltose-binding protein, poly-His tag, or glutathione-S-transferase fusion proteins. All of these, as well as many other prokaryotic expression systems, are well known in the art and widely available commercially (e.g., pGEX-27 (Amrad, USA) for GST fusions).

Eukaryotic cells and cell lines useful for producing the transformed cells of the invention include mammalian cells (e.g., endothelial cells, mast cells, COS cells, CHO cells, fibroblasts, hybridomas, oocytes, embryonic stem cells), insect cells lines (e.g., *Drosophila* Schneider cells), yeast, and fungi. Eukaryotic cells are particularly useful for embodiments in which it is necessary that the 3-OST proteins, or functional fragments thereof, be properly post-translationally modified (e.g., N-glycosylated) because N-glycosylation of these proteins appears to be important to their stability and/or activity. Currently preferred cells are mammalian cells and, in particular, COS-7 cells, CHO, cells, murine primary cardiac microvascular endothelial cells (CME), murine mast cell line C57.1, human primary endothelial cells of umbilical vein (HUVEC), F9 embryonal carcinoma cells, rat fat pad endothelial cells (RFPEC), L cells (e.g., murine LTA tk⁻ cells), and cells derived from the transgenic animals of the invention.

To accomplish expression in eukaryotic cells, a wide variety of vectors have been developed and are commercially available which allow inducible (e.g., LacSwitch expression vectors, Stratagene, La Jolla, Calif.) or constitutive (e.g., pcDNA3 vectors, Invitrogen, Chatsworth, Calif.) expression of 3-OST nucleotide sequences under the regulation of an artificial promoter element. Such promoter elements are often derived from CMV or SV40 viral genes, although other strong promoter elements which are active in eukaryotic cells can also be employed to induce transcription of 3-OST nucleotide sequences. Typically, these vectors also contain an artificial polyadenylation sequence and 3' UTR which can also be derived from exogenous viral gene sequences or from other eukaryotic genes. These expression systems are commonly available from commercial sources and are typified by vectors such as pcDNA3 and pZeoSV (Invitrogen, San Diego, Calif.). As described below, the vector pcDNA3 has been successfully used to cause expression of 3-OST-1 proteins in transfected COS-7 cells. Numerous expression vectors are available from commercial sources to allow expression of any desired 3-OST transcript in more or less any desired cell type, either constitutively or after exposure to a certain exogenous stimulus (e.g., withdrawal of tetracycline or exposure to IPTG).

Vectors may be introduced into the recipient or "host" cells by various methods well known in the art including, but not limited to, calcium phosphate transfection, strontium phosphate transfection, DEAE dextran transfection, electroporation, lipofection, microinjection, ballistic insertion on micro-beads, protoplast fusion or, for viral or phage vectors, by infection with the recombinant virus or phage.

Transgenic Animal Models

The present invention also provides for the production of transgenic non-human animal models in which wild type, allelic variant, chimeric, or antisense 3-OST sequences are expressed, or in which 3-OST sequences have been inactivated or deleted (e.g., "knock-out" constructs) or replaced with reporter or marker genes (e.g., "knock-in reporter construct"). The 3-OST sequences may be conspecific to the transgenic animal (e.g., murine sequences in a transgenic mouse) or transpacific to the transgenic animal (e.g. human sequence in a transgenic mouse). In such a transgenic animal, the trangenic sequences may be expressed inducibly, constitutively or ectopically. Expression may be tissue-specific or organism-wide. Engineered expression of 3-OST sequences in tissues and cells not normally containing 3-OST gene products may cause novel alterations of heparan polysaccharide structure and lead to novel cell or tissue phenotypes. Ectopic or altered levels of expression of 3-OST sequences may alter cell, tissue and/or developmental phenotypes. Transgenic animals are useful as models of thromboembolic and other disorders arising from defects in heparan sulfate biosynthesis or metabolism. Transgenic animals are also useful for screening compounds for their effects on HS biosynthesis mediated by 3-OSTs. Transgenic animals transformed with reporter constructs may be used to measure the transcriptional effects of small molecules, drugs, protein physiological mediators, carbohydrate effectors, mimetic compounds or physical perturbations on the expression of 3-OST loci in vivo. The transgenic animals of the invention, may be used to screen such compounds for therapeutic utility.

Animal species suitable for use in the animal models of the present invention include, but are not limited to, rats, mice, hamsters, guinea pigs, rabbits, dogs, cats, goats, sheep, pigs, and non-human primates (e.g., Rhesus monkeys, chimpanzees). For initial studies, transgenic rodents (e.g., mice) are preferred due to their relative ease of maintenance and shorter life spans. Transgenic non-human primates may be preferred for longer term studies due to their greater similarity to humans and their higher cognitive abilities.

Using the a nucleic acid disclosed and otherwise enabled herein, there are now several available approaches for the creation of a transgenic animal. Thus, the enabled animal models include: (1) animals in which sequences encoding at least a functional fragment of a wild type 3-OST gene has been recombinantly introduced into the genome of the animal as an additional gene, under the regulation of either an exogenous or an endogenous promoter element, and as either a minigene (i.e., a genetic construct of the 3-OST with the introns, if any, removed) or a large genomic fragment; (2) animals in which sequences encoding at least a functional fragment of a normal 3-OST gene have been recombinantly substituted for one or both copies of the animal's homologous 3-OST gene by homologous recombination or gene targeting; (3) animals in which one or both copies of one of the animal's homologous 3-OST genes have been recombinantly "humanized" by the partial substitution of sequences encoding the human homologue by homologous recombination or gene targeting; (4) animals in which sequences encoding 3-OST transcriptional elements linked to a reporter gene have replaced the endogenous 3-OST gene and transcriptional elements; (5) "knock-out" animals in which one or both copies of the animal's 3-OST sequences have been partially or completely deleted or have been inactivated by the insertion or substitution by homologous recombination or gene targeting of exogenous sequences (e.g., stop codons,); (6) animals in which additional genes related to the biosynthesis or metabolism of heparan sulfates have been altered (e.g., a murine transgenic in which all of the genes in the HS pathway have been humanized). These and other transgenic animals of the invention are useful as models of thromboembolic and other disorders arising from defects in heparan sulfate biosynthesis or metabolism. These animals are also useful for screening compounds for their effects on HS biosynthesis mediated by 3-OSTs.

To produce an animal model (e.g., a transgenic mouse), a wild type or allelic variant 3-OST sequence or a wild type or allelic variant of a recombinant nucleic acid encoding at least a functional fragment of a 3-OST is preferably inserted into a germ line or stem cell using standard techniques of oocyte or embryonic stem cell microinjection, or other form of transformation of such cells. Alternatively, other cells from adult organism may be employed. Animals produced by these or similar processes are referred to as transgenic. Similarly, if it is desired to inactivate or replace an endogenous 3-OST sequence, homologous recombination using oocytes, embryonic stem or other cells may be employed. Animals produced by these or similar processes are referred to as "knock-out" (inactivation) or "knock-in" (replacement) models.

For oocyte injection, one or more copies of the recombinant DNA constructs of the present invention may be inserted into the pronucleus of a just-fertilized oocyte. This oocyte is then reimplanted into a pseudo-pregnant foster mother. The liveborn animals are screened for integrants using analysis of DNA (e.g., from the tail veins of offspring mice) for the presence of the inserted recombinant transgene sequences. The transgene may be either a complete genomic sequence introduced into a host as a YAC, BAC or other chromosome DNA fragment, a cDNA with either the natural promoter or a heterologous promoter, or a minigene containing all of the coding region and other elements found to be necessary for optimum expression.

To create a transgene, the target sequence of interest (e.g., wild type or allelic variant 3-OST sequences) are typically ligated into a cloning site located downstream of some promoter element which will regulate the expression of RNA from the sequence. Downstream of the coding sequence, there is typically an artificial polyadenylation sequence. An alternative approach to creating a transgene is to use an exogenous promoter and regulatory sequences to drive expression of the transgene. Finally, it is possible to create transgenes using large genomic DNA fragments such as YACs which contain the entire desired gene as well as its appropriate regulatory sequences.

Animal models may be created by targeting endogenous 3-OST sequence in order to alter the endogenous sequence by homologous recombination. These targeting events can have the effect of removing endogenous sequence (knock-out) or altering the endogenous sequence to create an amino acid change associated with human disease or an otherwise abnormal sequence (e.g., a sequence which is more like the human sequence than the original animal sequence) (knock-in animal models). A large number of vectors are available to accomplish this and appropriate sources of genomic DNA for mouse and other animal genomes to be targeted are commercially available from companies such as GenomeSystems Inc. (St. Louis, Mo., USA). The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of the sequences included in the vector. Alternatively, the sequences can be chosen to cause deletion of sequences that would normally reside between the left and right arms of the vector surrounding the neomycin cassette. The former is known as a knock-in, the latter is known as a knock-out.

Retroviral infection of early embryos can also be done to insert the recombinant DNA constructs of the invention. In this method, the transgene (e.g., a wild type or allelic variant 3-OST sequence) is inserted into a retroviral vector which is used to directly infect embryos (e.g., mouse or non-human primate embryos) during the early stages of development to generate partially transgenic animals, some of which bear the transgenes in germline cells.

Alternatively, homologous recombination using a population of stem cells allows for the screening of the population for successful transformants. Once identified, these can be injected into blastocysts, and a proportion of the resulting animals will show germline transmission of the transgene.

Techniques of generating transgenic animals, as well as techniques for homologous recombination or gene targeting, are now widely accepted and practiced. A laboratory manual on the manipulation of the mouse embryo, for example, is available detailing standard laboratory techniques for the production of transgenic mice (69).

Finally, equivalents of transgenic animals, including animals with mutated or inactivated 3-OST sequences may be produced using chemical or x-ray mutagenesis of gametes, followed by fertilization. Using the isolated a nucleic acid disclosed or otherwise enabled herein, one of ordinary skill may more rapidly screen the resulting offspring by, for example, direct sequencing, SSCP, RFLP, PCR, or hybridization analysis to detect mutants, or Southern blotting to demonstrate loss of one allele by dosage.

Substantially Pure Proteins

In one aspect, the present invention provides substantially pure preparations of 3-OST proteins. In preferred embodiments, the 3-OST proteins are 3-OST-1, 3-OST-2, 3-OST-3A, 3-OST-3B, 3-OST-4 or ce3-OST proteins. In particularly preferred embodiments, the 3-OST proteins are those disclosed as SEQ ID NO: 2, SEQ ID NO: 4, SEQ ID NO: 6, SEQ ID NO: 8, SEQ ID NO: 10, SEQ ID NO: 12, or SEQ ID NO 15. As shown in the examples below, nucleic acids encoding all or a portion of one mammalian 3-OST protein may be used to isolate homologues in other species by standard techniques known to those of ordinary skill in the art. Thus, the present invention also enables substantially pure protein preparations of 3-OST proteins of other mammalian species including, for example, rats, goats, sheep, cows, pigs, and non-human primates. Similarly, the isolated nucleic acids disclosed herein may be used to screen additional human or other mammalian genetic libraries (e.g., genomic or cDNA libraries) to identify allelic variants of the particularly disclosed sequences. Thus, the present invention also enables substantially pure protein preparations of human and other mammalian 3-OST allelic variants.

In another aspect, the present invention provides 3-OST protein variants in which conservative substitutions have been made for certain residues, or chimeric 3-OST proteins in which the sequences of various 3-OST proteins have been mixed, to produce non-naturally occurring variants which retain 3-O-sulfotransferase activity. Conservative substitutions are preferably made in those regions of the proteins which are already known to vary amongst the human and murine sequences (see FIG. 1) or between the 3-OST-1, 3-OST-2, 3-OST-3A, 3-OST-3B 3-OST-4, and ce3-OST proteins (see, e.g., FIG. 2). Substitutions are to be avoided in those areas which have been implicated in catalysis (see above). Chimeric 3-OST proteins may be made using the disclosed sequences as reference sequences, and these chimeras may also be subjected to conservative substitutions as described above. In addition, based upon the homologies of the 3-OST proteins to other glucosaminyl sulfotransferases (e.g., 2-OST, NST-1, NST-2), one of ordinary skill in the art may produce chimeric 3-OSTs using those proteins as reference sequences (see, e.g., FIG. 2).

In preferred embodiments, the 3-OST proteins have at least 60%, preferably at least 70%, and more preferably at least 80% amino acid sequence similarity to the mammalian 3-OST sequences particularly disclosed herein, and retain 3-O-sulfotransferase activity. Most preferably, the sequences have at least 90% or 95% amino acid sequence similarity to the disclosed reference sequences. Such sequences may be routinely produced by those of ordinary skill in the art, and 3-O-sulfotransferase activity may be tested by routine methods such as those disclosed herein.

The substantially pure proteins of the present invention may be joined to other polypeptide sequences for use in various applications. Thus, for example, the proteins of the invention may be joined to one or more additional polypeptides so as to form a fusion protein, as is commonly known in the art and as described in the examples below. The additional polypeptides may be joined to the N-terminus, C-terminus or both termini of the 3-OST protein. Such fusion proteins may be particularly useful if the additional polypeptide sequences are easily identified (e.g., by providing an antigenic determinant) or easily purified (e.g., by providing a ligand for affinity purification).

In another aspect, the substantially pure 3-OST proteins of the present invention may comprise only a portion or fragment of the amino acid sequence of a complete mammalian 3-OST protein. For example, as described above, the 3-OST-1 proteins comprise a twenty amino acid signal sequence which is removed post-translationally to yield the mature proteins. In some instances (e.g., when employing 3-OST-1 proteins in vitro), it may be preferable to employ only the mature protein or a minimal fragment retaining 3-O-sulfotransferase activity. In addition, the four C-terminal residues of 3-OST-1 may be involved in localization of the protein within the Golgi apparatus. In some instances (e.g., when employing 3-OST-1 proteins in vitro), it may be preferable to employ a 3-OST-1 protein which does not include these residues, as they will be unnecessary for in vitro function. As described above, an approximately 260 amino acid portion of the 3-OST proteins includes the catalytically active region and, therefore, it may be preferable to employ a 3-OST protein which includes only this functional fragment which retains 3-O-sulfotransferase activity. Thus, in certain preferred embodiments, the present invention provides substantially pure 3-OST proteins including mature forms of a mammalian 3-OST-1 protein, C-terminally truncated forms, or minimal functional fragments thereof. In addition, as described above, these proteins may also comprise conservative substitution variants or chimeras of 3-OST proteins.

In another aspect, the present invention provides for substantially pure protein preparations which comprise a sequence of at least 6–12, preferably 10–16, more preferably 16–22 consecutive amino acid residues from any one of SEQ ID NO: 2, SEQ ID NO: 4, SEQ ID NO: 6, SEQ ID NO: 8, SEQ ID NO: 10, SEQ ID NO: 12, and SEQ ID NO: 15. Such polypeptides have utility to raise antibodies to corresponding regions of the 3-OST proteins. In particular, an analysis of the amino acid sequences of the 3-OST proteins suggests that there are regions which will have particular utility in generating antibodies. Thus, in preferred embodiments, the inventions provides antigenic 3-OST polypeptides selected from the group consisting of (a) residues 4–29, 144–152, 208–222, 31–42, 155–181, 72–94, 195–205, 278–293, 113–136, 56–66, 230–245, 257–263, 301–306, 267–272 and 101 –107 of SEQ ID NO 2; (b) residues 4–22, 140–148, 205–218, 68–90, 191–201, 274–289, 110–133, 51–62, 226–241, 253–259, 151–163, 168–181, 297–302, 27–34, 97–107 and 263–268 of SEQ ID NO: 4; (c) residues 18–44, 199–207, 114–123, 319–328, 250–275, 238–246, 128–143, 47–59, 83–98, 332–349, 178–186, 289–295, 310–316, 63–76, 4–9, 209–218, 170–176 and 300–305 of SEQ ID NO: 6; (d) residues 22–57, 236–256, 166–186, 151–161, 138–147, 77–85, 348–354, 87–94, 323–335, 360–366, 284–314, 217–224, 376–383, 4–20, 130–136, 67–73, 389–395 and 338–343 of SEQ ID NO: 8; (e) residues 221–241, 8–66, 151–171, 135–146, 333–339, 308–320, 345–351, 269–299, 202–209, 361–368, 86–100, 71–80, 115–129, 374–380 and 323–328 of SEQ ID NO: 10; and (f) residues 280–290, 321–364, 371–388, 211–231, 393–399, 310–316, 421–438, 405–411, 262–268 and 292–301 of SEQ ID NO: 12. Note that these polypeptides are listed in decreasing order of preference within in group (a) to (f). Preferred antigenic peptide sequences also include residues 218–231, 87–100, 167–180 and 275–288 of SEQ ID NO: 2, which have been successfully used to generate antibodies to m3-OST-1.

Thus, in another aspect, the present invention provides for antibodies and methods for making antibodies which selectively bind with the 3-OST proteins.

These antibodies include monoclonal and polyclonal antibodies, as well as functional antibody fragments such as F(ab) and Fc.

The proteins or peptides of the invention may be substantially purified by any of a variety of methods selected on the basis of the properties revealed by their protein sequences. As shown in the examples below, and previously described (26), cells naturally expressing 3-OST-1 proteins secrete the protein when grown in culture, and the proteins may be isolated from the cell culture medium. The 3-OST-2, 3-OST-3A, 3-OST-3B and 3-OST-4 proteins, however, appear to include transmembrane domains. Thus, these proteins are not expected to be secreted at high levels. Because the 3-OSTs are found in the Golgi apparatus and microsomal bodies of cells which naturally express them, a fraction of cells including these organelles may be isolated and the proteins may be extracted from this fraction by, for example, detergent solubilization. Alternatively the 3-OST proteins, fusion proteins, or fragments thereof, may be purified from cells transformed or transfected with expression vectors. For example, insect cells such as *Drosophila* Schneider cells and baculovirus expression systems may be employed with vectors such as pPLUEBAC and pMELBAC (Stratagene. La Jolla, Calif.); yeast expression systems with vectors such as pYESHIS Xpress vectors (Invitrogen, San Diego, Calif.); eukaryotic expression systems with vectors such as pcDNA3 (Invitrogen, San Diego, Calif.), which causes constitutive expression, or LacSwitch (Stratagene, La Jolla, Calif.) which is inducible; or prokaryotic expression systems with vectors such as pKK233-3 (Clontech, Palo Alto, Calif.). In the event that the protein or fragment localizes within microsomes derived from the Golgi apparatus, endoplasmic reticulum. or other membrane containing structures of such cells, the protein may be purified from the appropriate cell fraction. Alternatively, if the protein does not localize within these structures, or aggregates in inclusion bodies within the recombinant cells (e.g., prokaryotic cells), the protein may be purified from whole lysed cells or from solubilized inclusion bodies by standard means.

Purification can be achieved using standard protein purification procedures including, but not limited to, affinity chromatography, gel-filtration chromatography, ion-exchange chromatography, high-performance liquid chromatography (RP-HPLC, ion-exchange HPLC, size-exclusion HPLC), high-performance chromatofocusing chromatography, hydrophobic interaction chromatography, immunoprecipitation, or immunoaffinity purification. Gel electrophoresis (e.g., PAGE, SDS-PAGE) can also be used to isolate a protein or peptide based on its molecular weight, charge properties and hydrophobicity.

A 3-OST protein, or a fragment thereof, may also be conveniently purified by creating a fusion protein including the desired 3-OST sequence fused to another peptide such as an antigenic determinant (e.g., from Protein A, see below) or poly-His tag (e.g., QIAexpress vectors, QIAGEN Corp., Chatsworth, Calif.), or a larger protein (e.g., GST using the pGEX-27 vector (Amrad, USA) or green fluorescent protein using the Green Lantern vector (GlBCO/BRL. Gaithersburg, Md.). The fusion protein may be expressed and recovered from prokaryotic or eukaryotic cells and purified by any standard method based upon the fusion vector sequence. For example, the fusion protein may be purified by immunoaffinity or immunoprecipitation with an antibody to the non-3-OST portion of the fusion or, in the case of a poly-His tag, by affinity binding to a nickel column. The desired 3-OST protein or fragment can then be further purified from the fusion protein by enzymatic cleavage of the fusion protein. Methods for preparing and using such fusion constructs for the purification of proteins are well known in the art and numerous kits are now commercially available for this purpose.

Currently preferred methods for small scale purification of 3-OST-1 proteins from the media of LTA cells grown in culture may be found in Liu et al. (26), and methods for purification of 3-OSTs produced recombinantly in COS-7 cells, CHO cells, murine primary cardiac microvascular endothelial cells (CME), murine mast cell line C57.1, and human primary endothelial cells of umbilical vein (HUVEC) may be found in the examples below. These methods may also be adapted for use with other cell and expression systems to obtain substantially pure 3-OST proteins.

In another aspect, the present invention provides for methods for producing the above-described proteins. Thus, in one set of embodiments, the isolated nucleic acids of the invention may be used to transform host cells or create transgenic animals. The proteins of the invention may then be substantially purified by well known methods including, but notlimited to, those described in the examples below. Alternatively, the isolated nucleic acids of the invention may be used in cell-free in vitro translation systems. Such systems are also well known in the art and include, but are not limited to, that described in the examples below.

Antibodies

The present invention also provides antibodies and methods of making antibodies, which will selectively bind to and, thereby, isolate or identify wild type and/or variant forms of the 3-OST proteins. The antibodies of the invention have utility as laboratory reagents for, inter alia, immunoaffinity purification of the 3-OSTs, immunoaffinity purification of 3-OST conjugates or complexes (e.g., 3-OST-AT, 3-OST-HS), Western blotting to identify cells or tissues expressing the 3-OSTs, and immunocytochemistry or immunofluorescence techniques to establish the cellular or extracellular location of the protein.

The antibodies of the invention may be generated using the entire 3-OST proteins of the invention or using any 3-OST epitope which is characteristic of that protein and which substantially distinguishes it from other host proteins. Such epitopes may be identified by comparing sequences of amino acid residues from a 3-OST sequence to computer databases of protein sequences from the relevant host. Preferably, the epitopes are chosen so as to be highly immunogenic and specific.

In a preferred embodiment, the immunogen/epitope is a protein sequence of at least 6–12, preferably 10–16, more preferably 16–22 consecutive amino acid residues of the disclosed OST genes. In particular, an analysis of the amino acid sequences of the 3-OST proteins suggests that there are regions which will have particular utility in generating antibodies. Thus, in preferred embodiments, the inventions provides antigenic 3-OST polypeptides.

3-OST immunogen preparations may be produced from crude extracts (e.g., microsomal fractions of cells expressing the proteins), from proteins or peptides substantially purified from cells which naturally or recombinantly express them or, for small immunogens, by chemical peptide synthesis. The 3-OST immunogens may also be in the form of a fusion protein in which the non-3-OST region is chosen for its adjuvant properties and/or the ability to either and/or facilitate purification. As used herein, a 3-OST immunogen shall be defined as a preparation including a peptide comprising at least 4–8, and preferably at least 9–15 consecutive amino acid residues of the 3-OST proteins or nucleic acids encoding such a peptide coupled with transcriptional elements, as disclosed or otherwise enabled herein. Therefore, any 3-OST derived polypeptide or protein sequences which are employed to generate antibodies to the 3-OSTs should be regarded as 3-OST immunogens.

The antibodies of the invention may be polyclonal or monoclonal, or may be antibody fragments, including Fab fragments, F(ab')$_2$, and single chain antibody fragments. In addition, after identifying useful antibodies by the method of the invention, recombinant antibodies may be generated, including any of the antibody fragments listed above, as well as humanized antibodies based upon non-human antibodies to the 3-OST proteins. In light of the present disclosures of 3-OST proteins, as well as the characterization of other 3-OSTs enabled herein, one of ordinary skill in the art may produce the above-described antibodies by any of a variety of standard means well known in the art. For an overview of antibody techniques, see *Antibody Engineering,* 2nd Ed., Borrebaek. ed. Oxford University Press, Oxford (1995).

As a general matter, monoclonal anti-3-OST antibodies may be produced by first injecting a mouse, rabbit, goat or other suitable animal with a 3-OST immunogen in a suitable carrier or diluent. As above, carrier proteins or adjuvants may be utilized and booster injections (e.g., bi- or tri-weekly over 8–10 weeks) are recommended. After allowing for development of a humoral response, the animals are sacrificed and their spleens are removed and resuspended in, for example, phosphate buffered saline (PBS). The spleen cells serve as a source of lymphocytes, some of which are producing antibody of the appropriate specificity. These cells are then fused with an immortalized cell line (e.g., myeloma), and the products of the fusion are plated into a number of tissue culture wells in the presence of a selective agent such as HAT. The wells are serially screened and replated, each time selecting cells making useful antibody. Typically, several screening and replating procedures are carried out until over 90% of the wells contain single clones which are positive for antibody production. Monoclonal antibodies produced by such clones may be purified by standard methods such as affinity chromatography using Protein A Sepharose, by ion-exchange chromatography, or by variations and combinations of these techniques.

The antibodies of the invention may be labeled or conjugated with other compounds or materials for diagnostic and/or therapeutic uses. For example, they may be coupled to radionuclides, fluorescent compounds, or enzymes for imaging or therapy, or to liposomes for the targeting of compounds contained in the liposomes to a specific tissue location.

Assays for Drugs which Affect 3-OST Expression

In another series of embodiments, the present invention provides assays for identifying small molecules or other compounds which are capable of inducing or inhibiting the expression of the 3-OST genes and proteins. The assays may be performed in vitro using non-transformed cells, established cell lines, or the transformed cells of the invention, or in vivo using normal non-human animals or the transgenic animal models of the invention.

In particular, the assays may detect the presence of increased or decreased expression of nucleic acids under the transcriptional control of 3-OST promoter and regulatory sequences on the basis of increased or decreased mRNA expression (using, e.g., the nucleic acid probes disclosed and enabled herein), increased or decreased levels of protein products encoded for such nucleic acids (using, e.g., the anti-3-OST antibodies disclosed and enabled herein), or increased or decreased levels of activity of such a protein (e.g., β-galactosidase or luciferase).

Thus, for example, one may culture cells known to express a particular 3-OST, or recombination modified to express at least a functional fragment or epitope of 3-OST protein under the transcriptional control of 3-OST promoter and add to the culture medium one or more test compounds. After allowing a sufficient period of time (e.g., 0–72 hours) for the compound to induce or inhibit the expression of the 3-OST, any change in levels of expression from an established baseline may be detected using any of the techniques well known in the art. Using the nucleic acid probes and/or antibodies disclosed and enabled herein, detection of changes in the expression of a 3-OST, and thus identification of the compound as an inducer or inhibitor of 3-OST expression, requires only routine experimentation. For example, one may assay for 3-OST activity by measuring the conversion of $HS^{Inact}$ into $HS^{Act}$ by methods known in the art (70).

In other embodiments, a recombinant assay is employed in which a reporter gene is operably joined to 3-OST promoter and regulatory sequences so as to be under the transcriptional control of these sequences. The reporter gene may be any gene which encodes a transcriptional or transitional product which is readily assayed or which has a readily determinable affect or phenotype. Preferred reporter genes are those encoding enzymes with readily detectable activity, including without limitation β-galactosidase, green fluorescent protein, alkaline phosphatase, or luciferase is operably joined to the 5' regulatory regions of a 3-OST gene. The 3-OST regulatory regions, may be readily isolated and cloned by one of ordinary skill in the art in light of the present disclosure of the coding regions of these genes. The reporter gene and regulatory regions are joined in-frame (or in each of the three possible reading frames) so that transcription and translation of the reporter gene may proceed under the control of the 3-OST regulatory elements. The recombinant construct may then be introduced into any appropriate host cell as described herein. The transformed cells may be grown in culture and, after establishing the baseline level of expression of the reporter gene, test compounds may be added to the medium. The ease of detection of the expression of the reporter gene provides for a rapid, high through-put assay for the identification of inducers and inhibitors of the 3-OST gene.

Compounds identified by this method will have potential utility in modifying the expression of the 3-OST genes in vivo. These compounds may be further tested in the animal models disclosed and enabled herein to identify those compounds having the most potent in vivo effects.

Methods for Heparan Modification

In another aspect, the present invention provides methods for 3-O-sulfating saccharide residues within a preparation of glycosaminoglycan or proteoglycan polysaccharides in which the polysaccharides include a polysaccharide sequence of GlcA→GlcNS±6S. These methods comprise contacting the GlcA→GlcNS±6S-containing polysaccharide preparation with 3-OST protein in the presence of a sulfate donor under conditions which permit the 3-OST to convert the GlcA→GlcNS±6S sequence to GlcA→GlcNS 3S±6S. In particular embodiments, the GlcA→GlcNS±6S sequence comprises a part of an $HS^{act}$ precursor sequence (i.e., GlcA→GlcNS±6S→IdoA 2S→GlcNS±6S or IdoA→GlcNAc 6S→GlcA→GlcNS±6S→IdoA 2S→GlcNS 6S) or a part of an $HS^{inact}$ precursor sequence (i.e., IdoA→GlcNS 6S→GlcA→GlcNS±6S→IdoA 2S→GlcNS 6S; IdoA→GlcNAc→GlcA→GlcNS±6S→IdoA 2S→GlcNS 6S; IdoA→GlcNS→GlcA→GlcNS±6S→IdoA 2S→GlcNS 6S; IdoA→GlcNAc 6S→GlcA→GlcNS±6S→IdoA 2S→GlcNS or IdoA→GlcNS 6S→GlcA→GlcNS±6S→IdoA 2S→GlcNS). Conversion of the $HS^{act}$ precursor pool to $HS^{act}$ increases the fraction with AT-binding activity and is particularly useful in the production of anticoagulant heparan sulfate products. Thus, in another embodiment, the present invention provides for means of enriching the AT-binding fraction of a heparan sulfate pool by contacting the polysaccharide preparation with 3-OST protein in the presence of a sulfate donor under conditions which permit the 3-OST $HS^{act}$ conversion activity. In preferred embodiments, the sulfate donor is 3'-phospho-adenosine 5'-phosphosulfate (PAPS).

Methods of Partially Sequencing Complex Polysaccharides

In another aspect, the present invention provides methods for partially sequencing complex polysaccharides such as heparan sulfates (HS) or other glycosaminoglycans (GAGs). In these methods, a pool of polysaccharides which includes sequences which may be 3-O-sulfated is contacted with a 3-OST protein in the presence of a sulfate donor.(e.g., PAPS) under conditions which permit sulfation by 3-OST. The treated polysaccharides are then subjected to degradation by enzymes which degrade polysaccharides in a sequence-specific manner (e.g., polysaccharide lyases; heparinase I, II or III) and the size profile of the resulting fragments is determined. An identical pool which has not been treated with 3-OST is similarly cleaved by the same enzymes and a size profile determined. Changes in the size profiles indicate that 3-OST activity has modified the saccharide units so as to prevent (or permit) cleavage at sites which previously were (or were not) cleaved. Thus, comparison of the profiles will indicate positions at which the target sequences for 3-OST activity are present and provide a partial polysaccharide sequence.

In another embodiment, the sequence of complex polysaccharides such as HS or GAG may be partially determined using sequence specific polysaccharide affinity fractionation. To this end, 3-OST proteins which lack enzymatic function can be identified or produced (e.g., altering or deleting a portion of the catalytic ST domain by site-directed or deletion mutagenesis). These inactive forms will bind GAGs in a sequence dependent manner. For example, the 3-OST-1 protein normally, minimally, binds a GAG sequence containing GlcA-GlcNS±6S. When the active site of this protein is neutralized, the $k_d$ of the protein for these sequences will be relatively unaffected. This reagent will allow sequence-specific saccharide affinity fractionation from complex mixtures of GAGs. The purified structures can be degraded in a step-wise fashion with exolytic, endolytic enzymes and/or nitrous acid, and the resulting degradation products can be compared to standard compounds of known structure. This method will allow the quantitation and characterization of known structures contained within unknown complex polysaccharide samples.

In another embodiment, partial sequence can be obtained using the 3-OSTs of the invention or other heparan sulfate sequence specific binding ligands as protective groups prior to treating the IIS or GAG with modifying agents that detectably alter the HS or GAG. Useful protective groups include catalytically inactive enzymes, chimeric enzymes and small molecule ligands with identified sequence binding specificities. The protecting group is contacted with the heparan or other glycosaminoglycan (GAGs), and the resultant complex is treated with one or more modifying agents. Useful modifying agents include catalytically active heparan lyases, sulfotransferases, N-deacetylases, epimerases, or chimeric proteins of the invention. In embodiments where multiple protecting groups and/or modifying reagents in are used in combination, the sample is first contacted with the protective group, then each modifying reagent may be with contacted with the protected polysaccharide, either simultaneously or in turn. The protective group will interfere with the ability of a chemically modifying agent to interact with, attach to and/or cleave specific GAG sequence motifs. The sample can then be analyzed for ligand-specific protection and/or cleavage to elucidate the sequence of the original GAG using separation and/or quantitation using methods known in the art.

In some embodiments, as a preliminary step, full length heparans and GAG oligomers can be fractionated over an immobilized affinity ligand immobilized at their reducing ends via hydrazide chemistry. The fraction of GAG captured by the immobile phase permits a quantitation of the mass or total percent of the target sequence (out of total GAG.) Thus, unique heparan or other GAG structures may be concentrated and/or specifically eluted for further analysis.

One useful method for the detection binding is the Biomolecular Interaction Assay or "BIAcore" system developed by Pharmacia Biosensor and described in the manufacturer's protocol (LKB Pharmacia, Sweden). In light of the present disclosure, one of ordinary skill in the art is now enabled to employ this system, or a substantial equivalent, to identify proteins or other compounds having sequence-specific HS or GAG binding capacity, or HS or GAGs sequences having 3-OST binding capacity. Such systems utilize surface plasmon resonance, an optical phenomenon that detects changes in refractive indices. A sample of interest is passed over an immobilized ligand (e.g., a 3-OST fusion protein or specific GAG) and binding interactions are registered as changes in the refractive index.

EXAMPLES

Cell Lines and Cell Culture

The clonal L cell line LTA (35, 41), the generation of clone 33, an LTA transfectant that over-expresses the ryudocan$_{12CAS}$ cDNA (33), a rapidly growing revertant of clone 33, L-33$^+$ (26), and RFPEC, an immortalized line derived from rat fat-pad endothelial cells (8) have previously been described. Primary mouse neonatal endothelial cells from the cardiac microvasculature of day 3–5 neonates (CME cells) (from Dr. Jay Edelberg, MIT/Beth Israel Hospital) and COS-7 cells (ATCC) were employed. Primary human umbilical cells (HUVEC) were maintain according to the supplier's (Clonetics Inc.) protocol. Unless otherwise stated, all cell lines were maintained in logarithmic growth by subculturing biweekly in Dulbecco's modified Eagle medium (Life Technologies, Inc.) containing 10% fetal bovine serum, 100 μg/ml streptomycin, and 100 units/ml penicillin at 37° C. under 5% $CO_2$ humidified atmosphere, as previously described (42). Exponentially growing cultures were generated by inoculating 54,000 cells/cm$^2$ and incubating for two days, whereas post-confluent cultures were produced by inoculating 250,000 cells/cm$^2$ and allowing growth for 10 days with medium exchanges on days 4, 7, 8, and 9.

Peptide Purification and Sequencing

The purification of mouse 3-OST-1 from L-33$^+$ has been previously described (26) and the final step 4 product was concentrated by reverse phase chromatography on a HP 1090 M system (Hewlett Packard) equipped with a C4 reverse phase HPLC column (250×2.1 mm, 300 Å pore size. 5 μm particle size) (Vydac, number 214TP52) equilibrated in 1.6% acetonitrile (v/v), 0.1% TFA (v/v). After application of sample, the reverse phase matrix was washed with 60% acetonitrile, 0.1% TFA, and bound species were eluted with 78.4% acetonitrile, 0.1% TFA. Samples of 1.5 or 3 μg, from two independent purifications, were digested with 0.15 or 0.3 μg, respectively. of endopeptidase Lys-C (Waco) in a reaction volume of 100 μl containing 1% RTX100 (Calbiochem), 10% acetonitrile and 100 mM Tris-HCl pH 8.0, at 37° C. for ~16 h (43). Digestion products were chromatographed on an HP 1090 M system (Hewlett Packard) equipped with the above described C4 reverse phase HPLC column equilibrated in 98% Buffer A (0.1% TFA (v/v))/2% Buffer B (80% acetonitrile (v/v)/0.85% TFA (v/v)). After application of digestion products, the reverse phase matrix was washed with 98% Buffer A/2% Buffer B, and bound species were eluted with linear gradients of Buffer B increasing to 37.5% over 60 min, to 75% over 30 min, and to 98% over 15 min (44). The eluate was monitored for absorbance at 210 and 280 nm, peptide peaks were individually collected and analyzed with a model 477A/120A Protein Sequenator (Applied Biosystems). In addition, the $NH_2$-terminal sequence of 1 μg of concentrated 3-OST-1 sample was directly determined.

Isolation of Mouse 3-OST-1 Clones

Isolation of Cytoplasmic and Poly(A)$^+$ RNA. Cytoplasmic RNA (17.5 mg) was isolated from post-confluent cultures of LTA cells (12 flasks of 175 cm$^2$, ~1.6×10$^9$ cells) by a modification of the procedure of Favaloro (45). Monolayers were twice washed with PBS, cells were recovered by trypsinization and centrifugation (1000×g for 2 min), and cell pellets were washed by resuspension in PBS followed by centrifugation (1300×g for 4 min). Cells were lysed by vortexing for 30 sec in 12 ml of ice cold 50 mM Tris, pH 7.4, 140 mM NaCl, 5 mM EDTA, 1% Triton X-100, 5 mM vanadium ribonucleoside complexes (Life Sciences Technologies), samples were incubated on ice for 10 min and then vortexed for 1 min. Nuclei were pelleted by centrifugation at 6000×g for 10 min, the supernatant was mixed with an equal volume of 200 mM Tris, pH 7.4, 300 mM NaCl, 2% SDS, 25 mM EDTA, containing 200 μg/ml of proteinase K (Boehringer Mannheim), and the mixture was incubated at 65° C. for 2 hr. Samples were extracted twice against an equal volume of phenol/chloroform/isoamyl alcohol (25:24:1), the aqueous phase was combined with 0.7 volumes of isopropanol, cytoplasmic RNA was pelleted by centrifugation at 3500×g for 10 min, and was resuspended in 3.6 ml of 10 mM Tris, pH 7.4, 1 mM EDTA. Poly(A)$^+$ RNA (59 μg) was isolated from 16 mg of cytoplasmic RNA by two sequential purifications against 100 mg of oligo(dT) cellulose (Life Sciences Technologies, #15939-010) according to the manufacturer's specifications except that binding and wash buffers contained 0.1% SDS and LiCl was substituted for NaCl. The final eluate (1.5 ml) was extracted against 1.5 ml of phenol/chloroform/isoamyl alcohol (25:24:1), the aqueous phase was then adjusted to 100 mM LiCl and 260 mM NaCl, an equal volume of isopropanol was added, the mixture was centrifuged at 15,000×g for 30 min and the poly(A)$^+$ RNA pellet was recovered in 40 μl of diethyl pyrocarbonate treated water.

PCR Cloning and Generation of a Mouse 3-OST-1 Probe. Degenerate PCR primers 1S, 2S, 2A, and 3A (described in Shworak et al. (1997) *J. Biol. Chem.* 272, in press) were obtained from Bio Synthesis. First strand cDNA was generated in a 50 μl volume from 5 μg of LTA poly(A)$^+$ RNA primed with oligo(dT) using an RT-PCR kit (Stratagene, La Jolla, Calif.) according to the manufacturer's specifications. Touchdown PCR (46, 47) reactions (50 μl) contained 1 μl of first strand cDNA. 25 pmol of each primer, 0.25 μl of AmpliTaq Gold (Perkin Elmer). 200 μM of each dNTP and 1× GeneAmp PCR buffer. Two distinct sets of touchdown PCR conditions were required to obtain optimal yields of product. For amplification with primers 1S and 2A, reactions were heated to 95° C. for 9 min, subjected to 20 cycles of 94° C. for 30 see, and 68° C. for 1 min with a 0.5° C. reduction per cycle, followed by 20 cycles of 94° C. for 30 sec, 58° C. for 30 sec with a 0.5° C. reduction per cycle, and 75° C. for 30 sec, then 15 cycles of 94° C. for 30 sec, 55° C. for 10 sec, and ramping to 75° C. over 50 sec. Alternatively, for amplification with primers 1S and 3A or primers 2S and 3A, reactions were heated to 95° C. for 4 min, subjected to 47 cycles of 95° C. for 30 sec, and 69.5° C. for 2 min with 0.2° C. and 1 sec reductions per cycle, followed by 25 cycles of 95° C. for 30 see, 60° C. for 15 sec, and ramping to 75° C. over 1 min. Amplification products were purified as the retentate from centrifugal ultrafiltration against a 30,000 molecular weight cutoff membrane (Millipore, # SK1P343JO), then 200 ng of DNA was end polished with Pfu DNA polymerase and subcloned into pCR-Script Amp SK(+) (Stratagene, La Jolla, Calif., #211188) according to the manufacturer's specifications. A resulting plasmid, pNWS 182, contained the 1S/3A amplification product of 779 bp which was released by digestion with EcoRI and SacII, and isolated by low melting point agarose gel electrophoresis. A $^{32}$P-labeled primer extension probe was then generated with a random primer labeling kit (Stratagene, La Jolla, Calif., # 300385) by replacing the random primers with 5 $\mu$M of primer 3A.

Construction and Screening of an L Cell cDNA Library. Using the manufacturer's recommended conditions, an oligo (dT)-primed λ Zap Express cDNA library (Stratagene, La Jolla, Calif., # 200451) was generated from 5 $\mu$g of LTA poly(A)$^+$ RNA which had been pretreated with methylmercury hydroxide. About 1.5×10$^6$ primary recombinants were plaque amplified by infection into E. coli XL1-Blue MRF'. From the amplified library, 1.3×10$^6$ plaques were transferred to Colony/Plaque Screen (Du Pont-New England Nuclear) and screened with the above described $^{32}$P-labeled probe specific for 3-OST-1. Hybridizations were performed at 42° C. in 1.7×SSC, 8.3% dextran sulfate, 42% formamide, 0.8% SDS and filters were washed twice with 2×SSC, 1% SDS for 30 min at 65° C. Positive clones were plaque purified and then in viva) excised into pBK-CMV based phagemids by infection with ExAssist helper phage followed by transduction of filamentous phage particles into E. coil XLOLR.

Isolation of Human 3-OST-1 cDNA Clones

The National Center for Biotechnology Information data bank of I.M.A.G.E. Consortium (LLNL) expressed sequence tag cDNA clones (48) was probed with the deduced mouse 3-OST-1 amino acid sequence to reveal three partial length species. I.M.A.G.E. Consortium CloneID 220372 (accession numbers H86812 and H86876) was from the retinal library of Soares (N2b4HR), whereas clones 301725 (accession numbers N90867 and W16558) and 301726 (accession numbers N90856 and W16555) were from the fetal lung library of Soares (NbHL19W) and were obtained from the TIGR/ATCC Special Collection (ATCC). The EcoRI/NolI insert of clone 220372 was $^{32}$P labeled by random priming and used to screen 5×10$^5$ plaques from a λ TriplEx Brain cDNA library (Clontech, Palo Alto, Calif.), as described above. Positive plaques were purified, TriplEx based plasmids were in vivo excised according to the manufacturer's protocol, and were sequenced as described below.

Characterization of Mouse and Human 3-OST-1 cDNA Clones

The 5' and 3' regions of all partial and full length clones were enzymatically sequenced from flanking primer sites of the respective cloning vectors. For full length clones the remaining sequence of both strands was obtained with internally priming oligonucleotides. Automated fluorescence sequencing was performed with Perkin Elmer Applied Biosystems Models 373A and 477 DNA sequencers. Each reaction typically yielded 400 to 600 bases of high quality sequence. cDNA sequence files were aligned and compiled with the program Sequencher 3.0 (Gene Codes Corp.). All additional manipulations were performed with the University of Wisconsin Genetics Computer Group sequence analysis software package. Sequence comparison searches were performed on the databases of GenBank, EMBL, DDBJ, PDB, SwissProt, PIR, and dbEST.

Expression of 3-OST-1 cDNAs

Construction of Expression Plasmids. The plasmid pCMV-3-OST contains the mouse 3-OST-1 cDNA, an EcoRI/YhoI fragment from pNWS228, inserted between the CMV promoter and the bovine growth hormone polyadenylation signal of EcoRI/XhoI digested and phosphatase treated pcDNA3 (Invitrogen). The plasmid pCMV-ProA3-OST is of similar structure, except the first 26 amino acid of 3-OST-1 are replaced with 291 amino acids encoding a fusion protein of the transin leader sequence followed by Protein A and a factor Xa cleavage site. pCMV-ProA-3-OST was generated by ligating a BamHI/SmaI fragment containing the Protein A region from pRK5F10PROTA(49), and an XmaI (end-filled with T$_4$ polymerase)/XhoI fragment containing most of the mouse 3-OST-1 cDNA from pNWS228, into BamHI/XhoI digested and phosphatase treated pcDNA3 (Invitrogen.). The in vitro transcription plasmid, pNWS237, contains a T3 promoter site 5' of the human 3-OST-1 cDNA and was constructed by inserting complementary oligonucleotides (Bio Synthesis) into the EcoRI site of the TriplEx based plasmid, pJL30.

Transient Expression of the Mouse 3-OST-1 cDNA in COS-7 Cells. For each expression construct, three 175 cm$^2$ flasks were seeded with 3.6×10$^6$ COS-7 cells, 6 h later the medium was exchanged with DMEM containing 10% Nu-Serum (Life Technologies, Inc.) with 100 $\mu$g/ml streptomycin and 100 units/ml penicillin, and cells were grown for an additional day. Monolayers were washed with PBS then incubated at 37° C. for 2.5 h with 10 ml/flask of freshly prepared DMEM containing 235 $\mu$g/ml DEAE-dextran (M.W. 500,000, Pharmacia), 9.5 mM Tris-HCl, pH 7.4, 0.9 mM chloroquine-diphosphate (Sigma), and 3 $\mu$g/ml of the appropriate pcDNA3 based expression plasmid. Monolayers were then exposed to freshly prepared 10% DMSO in PBS for 1.5 min, washed twice with nonsupplemented DMEM, fed 30 ml/flask of DMEM containing 10% fetal bovine serum, 100 $\mu$g/ml streptomycin, and 100 units/ml penicillin, and cells were grown for an additional day. Monolayers were washed with PBS, then cells were grown in 40 ml/flask Serum-Free Medium (DMEM containing 25 mM HEPES, pH 8.0, 1% Nutridoma SP (Boehringer Mannheim) (v/v.), an additional 2 mM glutamine, 10 ng/ml biotin (Pierce), 100 $\mu$g/ml streptomycin, 100 units/ml penicillin, and 1× of a previously described Trace Metal Mix (26)) for 24 h. COS-cell conditioned Serum-Free Medium was harvested, debris was removed by centrifugation at 1,000×g for 10 min followed by filtration through a 0.45 $\mu$m membrane, then samples were either immediately processed or were snap frozen with liquid nitrogen and stored at −80° C. Occasionally, conditioned medium from a second incubation of 8–24 h was also collected.

Purification of Wild-type and Protein A Tagged Mouse Recombinant 3-OST-1. Wild-type mouse recombinantly expressed 3-OST-1 enzyme (r3-OST-1) was purified, at 4° C., from 240 ml. of freshly generated Serum-Free Medium conditioned by COS-7 cells transfected with pCMV-3-OST. The medium was adjusted to pH 8.0, mixed with an equal volume 2% glycerol, then loaded (25 ml/h) onto a heparin-AF Toyopearl-650M column (0.8×5.7 cm) (TosoHaas, Montgomeryville, Pa.) equilibrated in 50 mM NaCl, 10 mM Tris-HCl, pH 8.0, 1% glycerol (v/v) (Buffer C). The column was washed with 20 ml of Buffer C at a flow rate of 0.8 ml/min, then with 20 ml of 150 mM NaCl, 10 mM Tris-HCl, pH 8.0, 1% glycerol (v/v) at a flow rate of 0.5 ml/min, and protein was eluted at a flow rate of 0.25 ml/min with a 20 ml linear NaCl gradient extending from 150 mM to 750 mM NaCl in Buffer C. The fractions exhibiting $HS^{act}$ conversion activity (approximately 4 ml) were pooled, brought to a final concentration of 0.6% CHAPS (w/v) (Sigma) and dialyzed for 16 h against 4l of 25 mM MOPS (3-[N-morpholino] propanesulfonic acid) (Sigma), pH 7.0, 1% glycerol (v/v), 0.6% CHAPS (w/v) (MCG buffer) containing 50 mM NaCl. The dialysate was applied to a 3',5'-ADP-agarose column (0.8×1.2 cm, 3.7 mmol of 3',5'-ADP/ml of gel) (Sigma) and eluted as previously described (26). The fractions containing $HS^{act}$ conversion activity were pooled (approximately 4 ml), aliquoted, frozen in liquid nitrogen and stored at −80° C.

Protein A tagged mouse r3-OST-1 was purified, at 4° C., from 155 ml of previously frozen Serum-Free Medium conditioned by COS-7 cells transfected with pCMV-ProA3-OST. IgG agarose beads (310 µl of a 50/50 slurry; Sigma) were gently stirred with the conditioned medium for 3 h, recovered by centrifugation at 2,000×g for 10 min, and washed twice with 1 ml of MCG containing 250 mM NaCl to remove nonspecifically bound protein. Protein A fusion-protein was eluted from the beads with two sequential 30 min incubations in 100 µl of 50 mM sodium acetate, pH 4.5, 150 mM NaCl, 0.6% CHAPS and 1% glycerol. The pooled eluates were combined with an equal volume of 500 mM MOPS, pH 7.0, 0.6% CHAPS, and 1% glycerol, then aliquoted, frozen in liquid nitrogen and stored at −80° C.

Retroviral Transduction of CHO and MNE Cells with 3-OST-1

Plasmid retrovirus vector construction. A retroviral transduction system was used to transduce CHO cells and mouse neonatal endothelial (MNE) cells. This system may serve as a model for in vivo transduction for use in gene therapy.

The retrovirus backbone plasmid pMSCV-PGK-EGFP is a derivative of pMSCVpac a (Dr. Robert Hawley University of Toronto.) The puromycin acetyl transferase gene cassette in pMSCVpac was removed and replaced with an Enhanced GFP (Dr. David Baltimore MIT). The pMSCV-PGK-GFP vector was assembled by digestion of the plasmid with HindIII and ClaI, followed by treatment with Klenow fragment. The EGFP cistron 720 bp fragment was derived from the digestion of pMSCV-EGFPpac with EcoRI, and blunting with the Klenow fragment. The EGFP blunt-ended fragment was then ligated into the blunt-ended pMSCV vector. The resulting plasmids were tested for proper orientation by restriction analysis. The reporter virus, pMSCVPLAP, is designed to express the wild type human placental alkaline phosphatase (PLAP) transcribed from the 5' LTR. pMSCV-SEAP-PGK-EGFP was made by cloning the secreted alkaline phoshphatase (SEAP) BglII and HpaI 1.723 kb fragment from pSEAP2-basic plasmid (Clontech, Palo Alto, Calif.) into the BglII and HpaI cut pMSCV-PGKEGFP vector. pCMV3-OST was digested with BglII and XhoI to release the wild type mouse 3-OST-1 cDNA. The 1.623 kb 3-OST-1 cDNA fragment was cloned into the BglII and XhoI sites in pMSCV-PGK-EGFP. The occurrence of the insert of interest present in the correct orientation was ascertained by restriction analysis. All plasmid DNA prepared for transfection was made with the Invitrogen SNAP-MIDI kits according to the manufacturer's directions.

Cells and cell culture. Dulbecco's modified Eagle medium (DMEM), F-12 Ham's medium and penicillin/streptomycin, 0.25% trypsin, 10 mM EDTA, were obtained from Life Technologies, Inc., GlBCO-BRL (Gaithersburg, Md.). The PHOENIX ecotropic retroviral packaging cell line (ATCC #SD 3444) was grown, in DMEM, 10% heat-treated fetal bovine serum (FBS) (JRH Biosciences. Lenexa, Kans.), 100 units/ml penicillin, 100 µg/ml. PHOENIX cells were subcultured three times weekly at a split ratio of approximately 1:8 in a 37° C. humidified, 5.0% $CO_2$ incubator. CHOK1 ATCC CCL 61 cells (CHO) were grown in F-12 medium supplemented with 10% fetal bovine serum, and 100 units/ml penicillin, 100 µg/ml in a 37° C. humidified, 5.0% $CO_2$ incubator. CHO cells were subcultured three times weekly at a split ratio of approximately 1:4 in a 37° C. humidified, 5.0% $CO_2$ incubator. $1 \times 10^6$ CHO cells were transfected with 10 µg of pcB7-ECOTROPIC (generous gift of Dr. Harvey Lodish) by the standard calcium phosphate precipitation technique. Plasmid pcB7-ECOTROPIC expresses the MCAT1 gene (ecotropic retrovirus receptor cDNA) and hygromycin resistance gene transcribed from separate constitutive promoters. The transfected cells were selected for hygromycin resistance in 200 µg/ml hygromycin (Life Technologies). The stable, hygromycin-resistant clones were assayed for their ability to-take up and express reporter virus (MSCVPLAP). Fixation and staining for cell-bound alkaline phosphatase was performed by standard techniques. CHO clone 4B was chosen because it transduced most efficiently at the highest dilution tested (i.e., 1:10,000), and was expanded for further analysis. Transduction of CHO4B with ecotropic retroviruses is equal to that achievable with NIH3T3 cells. Low passage number (passage 2–5), primary mouse neonatal cardiac endothelial cells (MNE) were prepared by standard techniques. MNE cells were cultured in a 1:1 vol./vol. admixture of EGM:EGM-2 (CLONETICS) in a 37° C., humidified, 5.0% $CO_2$ incubator. MNE cells were subcultured once weekly at a split ratio of approximately 1:3 in a 37° C., humidified, 5.0% $CO_2$ incubator.

Northern blot analysis. Total RNA was prepared from confluent T-80 flasks of each of the transduced and untransduced cells using the QIAGEN RNAeasy kit with QIASHREDDER. 10 µg of total cellular RNA was denatured and resolved by electrophoresis in a 1.5% agarose gel, and then blotted onto GENE-Screen+ (DuPont NEN) with 2×SSPE. The membrane was then UV cross-linked using a STRATAlinker. $^{32}P$-radiolabeled cDNA probes were prepared from the fragments of DNA used for cloning the mouse 3-OST-1 and SEAP as described above. Radiolabeled probes were prepared using 25 ng of each template and the Amersham Megaprime kit, and α $^{32}P$ dCTP from DuPont NEN according to the manufacturer's directions. Hybridizations were performed in sealable plastic bags at 68° C. with $1 \times 10^6$ cpm of probe/ml in 10 ml of QUICKHYB (Stratagene, La Jolla, Calif.), following the manufacturer's instructions. Post-hybridization washes were: once for 15 minutes in 1×SSPE, 1.0% SDS at 45° C.; and then twice for 15 minutes each in 0.2×SSPE, 0.5% SDS 650C. After washing, the blots were briefly air dried, placed in sealable plastic bags then exposed to Kodak XAR-MS film with intensifying screens at −80° C. for from overnight to five days. Quantitation of hybridizing signal intensity was performed using a Betascope 603 blot analyzer. Transcripts derived from the 5' LTR of these engineered proviruses are large (ca. 7 kb). Since they are large, have multiple sites of transcriptional initiation provirus (5' LTR and pgk promoters), and the 3-OST-1 construct has more than one poly(A) addition signal, bona-fide hybridizable mRNA will appear as different sizes in northern blot analysis. The total amount of hybridizing material detected, per sample lane, with any one probe was used to calculate and compare mRNA expression levels.

Virion production. Virions were produced by programming ecotropic PHOENIX packaging cells with recombinant provirus plasmids using the calcium phosphate transfection technique. 10 µg/well of each recombinant retroviral construct plasmid was transfected via calcium precipitation with an overnight incubation period. Following the precipitation step, the cells were re-fed with 2 ml/well of fresh DMEM and incubated overnight. Each 2 ml of viral supernatant was collected and flash-frozen in liquid nitrogen and stored at −80° C., or used directly after a low-speed centrifugation.

Transduction Drotocol. Target cells were trypsinized, counted with a Coulter cell counter and then plated at 150,000 cells (NIH 3T3/CHO4B) or 50,000 cells (MNE) per well of a cluster-6 well plate. 24 hours later, target cells (<70% confluent) were incubated overnight with viral supernatants containing as adjuvants either 5 µg/ml polybrene for NIH3T3/CHO4B or 25 µg/ml DEAE-dextran (Pharmacia) for MNE. After 12 hours of virus exposure, the growth media was replaced. CHO cells destined for FACS sorting were exposed to recombinant retrovirus two times at a multiplicity of infection (MOI) of 0.3. MNE cells were transduced one time for 12 hours at an MOI of 0.74 for recombinant 3-OST-1 virus and 0.72 for recombinant SEAP virus. Transduced cells were allowed to incubate in fresh growth medium for 48 hours prior to FACS to allow for maximum proviral expression. Recombinant virus titers ranged from $1 \times 10^5 - 2 \times 10^6$ infectious particles per ml as measured with either NIH3T3 or CHO4B cells using. FACS analysis scoring for EGFP positive cells. Virus titers were reduced approximately eight to ten-fold on primary MNE cells relative to NIH3T3.

Cell-Free Synthesis of Mouse and Human r3-OST-1.

Synihetic capped mouse and human 3-OST-1 mRNAs were generated from NoII linearized pNWS228 and HinDIII linearized pNWS237, respectively, using $T_3$ polymerase and $m^7G(5')ppp(5')G$, as previously described (50). Unlabeled in vitro translation reactions (25 µl) contained 0.25 µg of synthetic mRNA, 1.8 µl canine pancreatic microsomal membranes (Promega), 0.5 µl each of Amino Acid Mixture Minus Leucine and Amino Acid Mixture Minus Methionine, and were performed with nuclease-treated reticulocyte lysate (Promega), according to the manufacturer's specifications.

Measurement of $HS^{act}$ Conversion Activity. The $HS^{act}$ conversion activity, a 3-OST-1 catalyzed reaction which requires unlabeled PAPS to convert $^{35}S\text{-}HS^{inact}$ into $^{35}S\text{-}HS^{act}$, of crude and purified r3-OST-1 samples was determined by comparison against a standard curve generated with 1 to 32 units of previously purified native 3-OST-1, as previously described (26). The $^{35}S\text{-}HS^{inact}$ substrate was purified from metabolically labeled cell surface HS of exponentially growing clone 33 cells, as previously described (35).

Identification of Enzymatic Reaction Products $^{35}S$-labeling of HS by r3-OST-1. $^{35}S$-labeled HS was generated by incubating the various forms of r3-OST-1 with [$^{35}S$]PAPS and unlabeled $HS^{inact}$, which were prepared as previously described (26, 35). Wild-type and Protein A tagged r3-OST-1 (2500 units of $HS^{act}$ conversion activity) purified from COS cell conditioned medium, were incubated in a 500 µl reaction mixture, as previously described (26), for 2 h at 37° C. and $^{35}S$-labeled polysaccharides were purified by DEAE-Sepharose chromatography as previously described (26). For cell-free synthesized r3-OST-1, $^{35}S$-labeling of HS was performed in a reticulocyte lysate based reaction mixture (35) except that 100 µl reactions contained 100 to 300 units of in vitro translated r3-OST, 180 nM unlabeled $HS^{inact}$, 5 µM PAPS ($60 \times 10^6$ cpm) and samples were incubated at 37° C. for 2 h. The reaction was quenched by the addition of 300 µl of 267 mM NaCl, 13.3 µg/ml glycogen and extraction against 600 µl of phenol/chloroform/isoamyl alcohol (25:24:1). $^{35}S$-labeled GAGs were ethanol precipitated (35) and then isolated by DEAE chromatography as previously described (26).

Identification of the Site of Sulfation on $HS^{act}$ and $HS^{inact}$. The DEAE eluates containing $^{35}S$-labeled polysaccharide were vacuum concentrated to 1/5 volume, then desalted at a flow rate of 0.9 ml/min on TSK G3000 $PW_{XL}$ (0.78×30 cm) and TSK G2500 $PW_{XL}$ (0.78×30 cm) (TosoHaas) columns connected in series equilibrated in 0.1 M ammonium bicarbonate. The desalted product was then affinity fractionated using AT/ConA gel to obtain $HS^{act}$ and $HS^{inact}$ as described previously (26). Analysis of labeled products by treatment with GAG lyases and low pH nitrous acid were performed as previously described (42). In addition, the $HS^{act}$ and $HS^{inact}$ samples were each subjected to hydrazinolysis, high pH nitrous acid (pH 5.5), low pH nitrous acid (pH 1.5), and sodium borohydride reduction with the resultant disaccharides characterized on reverse phase ion pairing HPLC (RPIP-HPLC) as previously reported (33, 34). The identification of [$^{35}S$]GlcA→AMN-3-O—$SO_3$ and [$^{35}S$] GlcA→AMN-3,6-O—$(SO_3)_2$ Was confirmed by co-chromatography on RPIC-HPLC with the appropriate $^3H$-labeled disaccharide standards, as described in prior publications (33,34).

Northern Blot Analysis

Total RNA from RFPEC and primary mouse CME cells was isolated by the method of Chomczynski and Sacchi (51I), whereas poly(A)+ RNA was isolated from HUVEC cells as described above for LTA cells. Total RNA from the mast cell line CI.MC/C57.1 (C57.1) (52) was from Dr. Stephen J. Galli (Beth Israel Hospital). Samples were resolved on 1.2% formaldehyde-agarose gels and subjected to Northern blot analysis as previously described (50). Mouse and human samples were hybridized with mouse or human probes, respectively, and washed as described for library screening, above, except hybridizations were performed at 60° C.

Peptide Sequencing and PCR Generation of a Mouse 3-O-Sulfotransferase-1 (3-OST-1)

1) Probe

The information necessary for the molecular cloning of mouse heparan sulfate D-glucosaminyl 3-O-sulfotransferase-1 (3-OST-1) was obtained by sequencing the amino terminus and Lys-C generated peptides of the enzyme that we had previously purified from large quantities of serum-free tissue culture medium conditioned by an L cell line (26). These studies established the structures of 14 partially overlapping peptides which encompass 185 amino acid residues. Degenerate PCR primers were synthesized based on the sequence of the amino terminus (primer 1S) and two endopeptidase derived fragments (primers 2S, 2A, and 3A). When PCR was performed on an LTA first strand cDNA template, products of about 210 (primers 1S/2A) and 780 (primers 1S/3A) and 610 (primers 2S/3A) bp were obtained, which suggests that all of the primer sites are contained within a single cDNA. To confirm this supposition, the two largest fragments were cloned into pCR-Script Amp SK(+) and inserts were sequenced, which revealed that the 1S/3A product is 779 bp and contains the 611 bp 2S/3A product. The 779 bp insert encodes 12 of the sequenced peptide fragments and so was $^{32}P$-labeled, as described above, and used as a probe for cDNA library screening.

Isolation and Characterization of Mouse 3-OST-1 cDNAs

An amplified λ Zap Express LTA cDNA library of 1.5× $10^6$ primary recombinants was constructed and $1.3 \times 10^6$ plaques were screened with the above described probe, which revealed 40 positives that were plaque purified and in vivo excised into plasmids. The cDNA inserts of each plasmid were characterized to eliminate duplicated recombinants due to library amplification. Size was determined by liberating cDNA inserts with digestion at flanking EcoRI and XhoI restriction sites followed by agarose gel electrophoresis; furthermore, the sequence at both ends of each insert was obtained from flanking vector primer sites. This analysis revealed 25 unique primary recombinants which predominantly contained inserts of approximately 1.7, 2.3, or 3.3 kb. These different species were considered to reflect natural size variants of the mouse message since northern blots of LTA poly(A)$^+$ RNA hybridized with 3-OST-1 probe revealed the same three size categories of message. The complete sequencing of 9 distinct primary recombinants, at least 2 from each size category, in conjunction with the partial sequencing of the remaining 16 clones showed that the size variants result from differences in the length of 5' untranslated region due to the insertion of 0–1629 bp at a single common internal point, the splice variant site. Most importantly, all clones shared identical protein coding regions and, therefore. the characterization and analysis of only the shortest species, the Class 1 cDNA, which lacks additional sequence at the splice variant site, is described below.

Sequence data was obtained from 2 essentially full length Class 1 cDNAs, and 5 partial length cDNAs to create a composite cDNA structure of 1685 bp (SEQ ID NO: 1), excluding the 3' poly(A) tract. The 5' untranslated region is 322 bp with the splice variant site occurring between nucleotides 216 and 217. This region contains 6 ATG sites which do not conform to consensus initiation sites (53) and are followed by near in-frame termination codons. An open reading frame of 933 bp begins at position 323 with the first consensus initiation ATG (a purine occurs at −3) (53). The length of the 3' untranslated region from all of the cDNA clones analyzed ranged from 301–430 bp. Within this terminal 129 bp, 5 distinct polyadenylation sites were observed and 13–18 bp upstream from each site is a variant of the consensus polyadenylation signal. Poly(A) tails were most frequently observed at the first site (position 1556, ~50% of clones).

Isolation and Characterization of Human 3-OST-1 cDNAs

Three clones containing partial length human 3-OST-1 cDNAs were identified by EST database searching (48) and were obtained from the TIGR/ATCC Special Collection, as described above. Sequencing of the insert ends revealed the clones to be essentially equivalent, as each contained the same 947 bp region of the human 3-OST-1 cDNA. The insert of I.M.A.G.E. Consortium CloneID 220372 was $^{32}$P-labeled and used to screen 5×10$^5$ plaques from a λ TriplEx Brain cDNA library. Three positives were identified and isolated as TriplEx plasmids, and the largest cDNA 1.3 kb was sequenced completely.

The nucleic acid sequence of mouse and human 3-OST-1 cDNAs are ~85% identical. The largest isolated human clone contains 118 bp of 5' untranslated region with 2 nonconsensus ATG sites. The sequences of human and mouse cDNAs ranking the splice variant site on the 5' limit are distinct (positions 211–216 of SEQ ID NO: 1 and positions 5–10 of SEQ ID NO: 3), but on the 3' limit are identical (positions 217–222 of SEQ ID NO: 1 and positions 11–16 of SEQ ID NO: 3), which raises the possibility that human 3-OST-1 mRNA may also exhibit 5' splice variants. The first consensus ATG (with a purine occurring at −3 and a G at +4) (53) initiates an open reading frame of 921 bp. For all 4 human cDNA clones examined, only a single polyadenylation site was observed resulting in a 3' untranslated region of 266 bp, which is 26 bp less than the most frequently observed 3' limit for the mouse cDNAs.

Predicted Protein Structures of Mouse and Human 3-OST-1

The mouse and human cDNAs encode novel 311 and 307 amino acid proteins of 35,876 and 35,750 daltons, respectively, that exhibit 93% similarity. The deduced mouse primary structure contains regions corresponding to all 13 sequenced peptides and the amino terminus. For both types of 3-OST-1, the encoded protein is predicted to be an intraluminal resident. Kyte-Doolittle hydropathy analysis reveals only a single major hydrophobic region which begins at the amino terminus and lacks sufficient length for a membrane spanning domain. Moreover, the hydrophobic region differs from a membrane anchor in that it contains two glutamine residues and is not flanked by cationic residues. Thus, the above stretch of 18 residues constitutes a hydrophobic leader signal, and this region is followed by a signal peptidase cleavage site between amino acids 20 and 21, as determined by the method of von Heijne (54). The possibility of signal peptidase cleavage is supported by the amino-terminal analysis of mouse 3-OST-1, which began with His$^{21}$. Given that heparan biosynthesis is considered to occur in the trans-Golgi, the above data suggest that the 3-OST-1 is an intraluminal enzyme. Just past the signal peptidase cleavage site, the mouse 3-OST-1 contains an extra 4 residues (ASp$^{24}$-Pro$^{25}$-Gly$^{26}$-Pro$^{27}$) not found in the human form. Both 3-OST-1 proteins exhibit 5 potential N-glycosylation sites which account for the apparent discrepancy between the molecular weights of the predicted amino terminus trimmed enzyme (34 kDa) and the previously purified enzyme (a broad band of 46 kDa was observed on SDS-PAGE) (26). Only two cysteine residues are present, and these closely spaced residues are likely to form a disulfide bond which generates a peptide loop of 10 amino acids. Interestingly, the carboxy 140 residue region is extremely basic (25% H, K, R; 12% E, D); however, this region does not exhibit previously recognized heparin binding motifs.

Recombinant Expression of Mouse and Human 3-OST-1 Enzyme (r3-OST-1)

Three distinct expression approaches were employed to confirm that the isolated cDNAs encode 3-OST-1 enzyme. The resulting recombinantly expressed 3-OST-1 enzyme was designated as r3-OST-1, to distinguish this form from the previously purified native 3-OST-1 enzyme. First, the vector pCMV-3-OST (a pcDNA3 derivative in which the CMV promoter transcribes the mouse 3-OST-1 cDNA) was transiently expressed in COS-7 cells and the resulting level of HS$^{act}$ conversion activity accumulated in Serum-Free Medium over 32 h was measured, as described above. HS$^{act}$ conversion activity is a 3-OST-1 catalyzed reaction which requires unlabeled PAPS to convert $^{35}$S-HS$^{inact}$ into $^{35}$S-HS$^{act}$. Before or after pcDNA3 transfection, typically COS-7 conditioned Serum-Free Medium contained a low but detectable amount of HS$^{act}$ conversion activity, whereas transfection by pCMV-3-OST elevated levels ~2,000-fold.

Second, to exclude the remote possibility that the expression of the mouse 3-OST-1 cDNA indirectly induces, rather than directly encodes, HS$^{act}$ conversion activity, a Protein A/3-OST-1 fusion protein was analyzed. COS-7 cells were transiently transfected with pCMV-ProA3-OST, a pCMV-3-OST derivative in which the amino-terminal 26 residues of the mouse 3-OST-1 are replaced with a Protein A tag, and Protein A tagged mouse r3-OST-1 was extracted with IgG agarose beads from 155 ml of conditioned Serum-Free Medium, as described above. The affinity purification recovered undetectable and less than 0.5% of initial $HS^{act}$ conversion activity from control pcDNA3 and pCMV-3-OST transfection samples, respectively, whereas ~7,000 units (10% recovery) were extracted from pCMV-ProA3-OST transfection samples. Thus, the mouse 3-OST-1 cDNA directly encodes $HS^{act}$ conversion activity.

Third, the activities of cell-free synthesized mouse and human r3-OST-1 were examined. Synthetic capped mouse and human 3-OST-1 mRNAs were generated by in vitro transcription and then in vitro translated with reticulocyte lysate in the presence and absence of canine pancreatic microsomal membranes, as described above. $HS^{act}$ conversion activity was undetectable in the control in vitro translation reactions which lacked mRNA template, with or without microsomal membranes. A low level $HS^{act}$ conversion activity resulted from the addition of synthetic 3-OST-1 mRNA templates to translation reactions lacking microsomal membranes (mouse, 0.86±0.028 units/µl, n=3; human, 2.1±0.063 units/µl, n=3); however, ~15-fold greater levels occurred when microsomal membranes were included in translation reactions (mouse, 14.3±0.27 units/µl, n=3; human, 32.4±2.1 units/µl, n=3). The apparent activation of nascent r3-OST-1 by co-translational processing within microsomes may result from signal peptidase cleavage, N-linked glycosylation, and/or a facilitation of correct protein folding. The slightly greater production from the human 3-OST-1 cDNA may reflect the more favorable context of the human initiation codon, or the reduced length of the human 5' untranslated region. Independent of the above considerations, the above data confirm that isolated mouse and human cDNAs encode $HS^{act}$ conversion activity.

Next, the biochemical specificity of the $HS^{act}$ conversion activity generated from each expression approach was examined by incubating crude or purified enzyme with [$^{35}$S]PAPS and unlabeled $HS^{inact}$, recovering radiolabeled GAG by DEAE chromatography and characterizing the resultant products. The $HS^{act}$ conversion activity of the wild-type mouse r3-OST-1 produced by transfecting COS-7 cells with pCMV-3-OST (1.35×10$^6$ units in 240 ml of conditioned Serum-Free Medium) was first purified away from potential contaminating sulfotransferase activities by heparin-AF Toyopearl chromatography followed by 3',5'-ADP-agarose chromatography, which yielded ~1 µg of protein containing 340,000 units (~20,000-fold purification with 25% overall recovery); whereas, the IgG agarose-purified Protein A tagged r3-OST-1 and in vitro translation reactions of mouse and human 3-OST-1 mRNA templates were directly analyzed, as described above. About 0.5–1× 10$^6$ cpm of product was generated with purified wild-type r3-OST-1, purified Protein A tagged r3-OST-1, and nonpurified in vitro translation reactions containing mouse and human r3-OST-1, respectively. Portions of each labeled product were incubated with purified heparitinase (0.5 units/ml) or chondroitinase ABC (0.5 units/ml) and HPLC-GPC analysis indicated that in all cases label was exclusively incorporated into HS. Portions of the labeled HS samples were also N-desulfated with nitrous acid at pH 1.5, and analyzed by P-2 polyacrylamide gel filtration to determine the amounts of liberated free [$^{35}$S]sulfate, as described above: The results demonstrated no increased generation of free [$^{35}$S]sulfate. Finally, portions of the labeled samples were AT affinity fractionated, which revealed that in each case ~40% of the $^{35}$S-label was incorporated in $HS^{act}$ and approximately ~60% of the $^{35}$S-label was incorporated in $HS^{inact}$. The labeled $HS^{act}$ and $HS^{inact}$ generated by the wild-type purified r3-OST-1 were chemically cleaved to disaccharides with nitrous acid treatment, appropriate 3H-labeled disaccharides standards were added, and the $^{35}$S- and $^3$H-labeled species were coresolved by RPIP-HPLC as outlined above. The results show that the $^{35}$S-label coelutes with [3H]GlcA→AMN-3-O—SO$_3$ and [$^3$H]GlcA→AMN-3,6-O—(SO$_3$)$_2$, respectively. This approach also revealed that Protein A tagged r3-OST-1, and in viiro translation derived mouse and human r3-OST-1 generated $^{35}$S-HS which only contained $^{35}$S-labeled disaccharides that coeluted with [$^3$H]GlcA→AMN-3-O—SO$_3$ and [$^3$H]GlcA→AMN-3,6-O—(SO$_3$)$_2$, respectively. It was previously shown that $^{35}$S-labeled GlcA→AMN-3,6-O—(SO$_3$)$_2$ generated by purified 3-OST-1 enzyme contains $^{35}$S solely in the 3-O-position (26). Thus, the expressed $HS^{act}$ conversion activities exclusively catalyze the transfer of sulfate to the 3-O-position of glucosamine units in $HS^{act}$ and $HS^{inact}$.

Northern Analysis of Rodent and Human 3-OST-1 Expression

Northern blot analysis reveals the presence of 3-OST-1 message in different kinds of endothelial cells as well as a mast cell line. Both cell types have previously been shown to form $HS^{act}$ and anticoagulant heparin, respectively (6, 8, 55). Three size categories of rodent 3-OST-1 mRNA (about 1.7, 2.3, 3.3 kb) and a single size species of the human message (about 1.7 kb) were evident. As described above, the mouse forms arise from differential splicing within the 5' untranslated region. Similar size categories are also expressed by rat (RFPEC) endothelial cells, suggesting a similar mechanism of origin. The abundance of each category varies with each cell line, which suggests that a mechanism exists to regulate such differential splicing. The immortalized mouse mast cell line, C57.1, expresses high levels of the same three size categories, which suggests that expression of a single 3-OST-1 gene is required for the synthesis of both $HS^{act}$ and anticoagulant heparin.

The 3-OST-1 Sequence Defines a Heparan Sulfotransferase Family

Extensive computer-aided data bank searching revealed the 3-OST-1 protein to be a previously unidentified protein; furthermore, the carboxy-terminal 250 residues exhibit a low homology (~30% similarity) to many previously identified sulfotransferases (which are typically ~300 residues in length) including chondroitin-, aryl-/phenol-, N-hydroxyarylamine-, alcohol-lhydroxysteroid-, flavonol-, and nodulation factor sulfotransferases. We also observed a slightly greater homology (~40% similarity) to a functionally unidentified open reading frame of 247 amino acids from Aeromonas salmonicida (GenBank accession number L37077). More importantly, the 3-OST-1 protein exhibits 50% similarity with all previously identified forms of the heparan biosynthetic enzyme N-deacetylase/N-sulfotransferase (NST). In particular, extensive homology exists across the entire 250–270 carboxy-terminal residues of these enzymes. Thus, it appears that a common sulfotransferase structure is shared by two distinct types of heparan biosynthetic enzyme. Given that NST is a bifunctional enzyme, the above observation suggests that NST enzymes possess sulfotransferase activity within a ~270 residue carboxy-terminal domain, whereas dcacetylase activity would be contained within the remaining ~560 luminal residues. Interestingly, the region of consensus Lys$^{302}$-Arg$^{323}$, which encompasses the presumptive cysteine bridged peptide loop (described above), exhibits complete conservation for 12 of the 22 residues (including both cysteines) among all 3-OST-1 and NST species.

Identification and Molecular Cloning of 3-OST-2, 3-OST-3A, 3-OST-3B and 3-OST-4

The 3-OST-1 protein exhibits a COOH-terminal region of ~260 residues which was determined to be a sulfotransferase (ST) domain based on homology to all known sulfotransferases. The National Center for Biotechnology Information data bank of expressed sequence tags (ESTs) was searched with amino acid sequences of the ST domain from the human 3-OST-1 cDNA to reveal seven human cDNAs encoding three novel related species. The forms were subsequently designated as 3-OST-2 (I.M.A.G.E. Consortium (LLNL) CloneID c-20d10), 3-OST-3 (Clone ID 284542) and 3-OST-4 (Clone IDs HIBCX69, IB727, 166466, 23279, and c-3ie01). These EST clones were obtained from the TIGRI-ATCC Special Collection, and the inserts were completely sequenced, revealing that all clones were of partial length.

To obtain full length clones, isoform specific probes were generated from the EST clones and used to screen λ TriplEx human cDNA libraries. 7 and 4 additional 3-OST-2 and 3-OST-4 cDNAs were isolated from a brain library, and 8 new 3-OST-3 cDNAs were recovered from a liver library. The cDNA inserts were completely sequenced, revealing the full length form for 3-OST-2 as well as 2 distinct full length forms for 3-OST-3 (3-OST-3A and 3-OST-3B). The additional 3-OST-4 clones were also of partial length.

3-OST-2, 3-OST-3A, 3-OST-3B and 3-OST-4 Protein Structures and Activities

The 3-OST-2, 3-OST-3A, and 3-OST-3B proteins are 367, 406, and 390 amino acids in length, respectively. All three proteins conform to the architecture of a type-II integral membrane protein. These proteins and the partial length 3-OST-4 share a common (85% similarity) ST domain region of ~260 amino acid at their COOH-terminus. To characterize the encoded HS sulfotransferase activities, the 3-OST-2, 3-OST-3A, and 3-OST-3B cDNAs were individually expressed in COS-7 cells.

The analysis of transfected cell extracts demonstrated that each enzyme transfers sulfate specifically to the 3-O position of glucosamine residues within HS; however distinct specificities occur. 3-OST-2 preferentially sulfates regions containing GlcA 2S→GlcNS to generate GlcA 2S→GlcNS 3S; whereas both 3-OST-3A, and 3-OST-3B recognize regions with IdoA 2S→GlcNS to generate IdoA 2S→GlcNS 3S.

Expression Patterns Indicate Biological Function

The biologic function of these novel enzymes was elucidated by performing northern blot analysis. 3-OST-4 is exclusively expressed in the brain, whereas 3-OST-2 mRNA predominantly occurs in the brain with minor levels also found in heart, lung, skeletal muscle and placenta. 3-OST-3 forms occur in virtually all tissues but with barely detectable levels in brain, low levels in heart, lung, skeletal muscle and kidney, and extremely abundant expression in liver and placenta. Thus 3-OST-2 and 3-OST-4 appear to be the brain counterparts of 3-OST-3. The product of 3-OST-3 (IdoA 2S→GlcNS 3S) has previously been shown to be extremely abundant in HSPGs isolated from the glomerular basement membrane (GBM) of the kidney. These HSPGs are critical to regulating the permselectivity of the GBM. This function occurs through interactions with extracellular matrix components that regulate the pore size of the matrix. Given that the liver, placenta, and kidney glomerulus are all responsible for the filtration of macromolecular components from blood and all exhibit high 3-OST-3 expression, it appears that 3-OST-3 serves a common function in each situation: to regulate macromolecular permeability. In this functional regard, the high brain expression of 3-OST-2 and 3-OST-4 correlates with the major molecular permeability barrier of the central nervous system, the blood brain barrier.

Therapeutic Utilities

The 3-OST heparan biosynthetic enzymes may be generated by recombinant expression of the isolated cDNAs to generate novel glycosaminoglycan drugs of specific structure through an in vitro biochemical synthesis approach. Specifically, 3-OST-1 may be used to generate anticoagulant pentasaccharides, which may be administered subcutaneously to treat thrombotic disorders such as deep vein thrombosis and pulmonary embolism. The 3-OST-1 enzyme may also be used to generate an orally absorbable form of pentasaccharide from an appropriate carbohydrate substrate linked to a hydrophobic group. In an analogous fashion, specific glycosaminoglycan products may be generated from 3-OST-2, 3-OST-3 and 3-OST-4, which may be used as therapeutics to alter macromolecular permeability of various vascular beds. Drugs which reduce capillary permeability may, at the very least, be used to treat (1) microproteinurea and macroproteinurea of renal diseases including diabetic nephropathy and the various forms of glomerulonephritis; (2) neoplastic growths by limiting nutrient supply to tumors; and (3) inflammatory diseases were macromolecular constituents of the plasma are required for initiating and maintaining a localized inflammation. Conversely, drugs which enhance capillary permeability may be used (1) as an adjunctive treatment to facilitate pharmacological access to vascular beds, which exhibit highly selective drug entry, such as the blood brain barrier and the placental barrier; and (2) to enhance nutrient supply to under-perfused tissues such as the myocardium after an infarct.

Specific heparan sulfate structures regulate additional biologic processes by interacting with numerous protein effector molecules including growth and differentiation factors (e.g., FGF family members, HB-EGF, HGF/SF, interferon γ, PDGF, SDGF, and VEGFNVPF), chemokines (e.g., MIP-1β, RANTES, and GRO), receptors (e.g., TGF-β receptors), mast cell proteases, protease inhibitors (e.g., AT, heparin cofactor II, leuserpin, plasminogen activator inhibitor-1, protease nexins), degradative enzymes (e.g., elastase, acetylcholinesterase, extra cellular superoxide dismutase, thrombin, tissue plasminogen activator, lipoprotein lipase. hepatic and pancreatic triglyceride lipase, and cholesterol esterase), apolipoproteins (e.g., apoB and apoE), matrix components (e.g., fibronectin, wnt-1, interstitial collagens, laminin, pleiotropin, tenascin, thrombospondin, and vitronectin) viral coat proteins (e.g., gC and gB of HSV types I and II, gC-II of CMV, and gp120 of HIV), nuclear proteins (e.g., c-fos, c-jun, RNA and DNA polymerases, and steroid receptors), cellular adhesion molecules (e.g., L-selectin, P-selectin, PECAM-1, and N-CAM) and other molecules (e.g., HB-GAM/pleiothrophin, amphoterin, and PF4).

Using routine methods (e.g., site-directed mutagenesis) the available 3-OST cDNAs may be selectively mutated to alter substrate recognition properties so as to produce enzymes that generate novel glycosaminoglycan structures which modulate the biologic processes regulated by the above effector molecules. Thus, novel drugs may also be biochemically synthesized from recombinantly expressed mutated enzymes. Such substances may serve to (1) enhance growth or regeneration of specific cell types such as the endothelial cells of the heart after infarction, or neurons in neurodegenerative diseases; (2) suppress undesirable cell growth in conditions such as cancer (either directly by acting on the cancers cells or indirectly by preventing endothelial cells from neovascularizing the tumor), atherosclerosis (by preventing smooth muscle cell growth), and inflammatory diseases characterized by cellular proliferation; (3) prevent metastasis of tumors by modulating cell/matrix interactions; (4) reduce the destructive side effects of inflammatory reactions by inhibiting degradative enzymes or by activating inhibitory molecules (e.g. protease inhibitors) which may be directly or indirectly protective by limiting extravasation of lymphocytes; (5) modulate serum lipid levels by enhancing or reducing the cellular or tissue uptake or degradation of specific lipoprotein classes; (6) treat viral infections by preventing viral entry into cells; and (7) facilitate axon regeneration subsequent to nerve severing.

Bacterial expression of 3-OST-1. The human and mouse 3-OST-1 proteins have been expressed as active, soluble protein in *E. coli*, This has been achieved using the pET system from NOVEGEN (Madison, Wis.). The human and mouse 3-OST-1 cDNA's were PCR amplified with pfu DNA polymerase and purified cloned plasmids as template. The primers that were used were designed to amplify a cDNA fragment starting, in frame, after the native signal sequence and including the native translational termination codon. Additionally, the PCR primers were designed to include restriction sites that would facilitate cloning into the vectors described below in the correct transcriptional/translational reading frames. 3-OST-1 was cloned into vectors pET12a, 15B and 28a according to the manufacturer's instructions. This places the 3-OST-1 cDNA downstream of a powerful, inducible T7 transcription site and includes an efficient Shine-Dalgamo sequence at the appropriate distance from the initiator methionine of the construct.

Good yields of active protein result from IPTG induction at room temperature. The specific activity appears to be less than purified, or Baculovirus/sf9 produced material. The exact magnitude of the diminution of activity is unclear at this time; however, it may be 10–1000 fold. The presently preferred purification scheme is: (1) Induction at 22° C. (2) Sonication of bacteria, centrifugation to remove inclusion bodies and cell debris, purification of crude bacterial sonicate on heparin sepharose as described eslewhere. (3) PAP column chromatography. (4) Gel permeation chromatography. Step (4) is only needed for obtaining monomeric, pure 3-OST-1, and not for active protein preparation.

References

1. Morawitz, P. (1958) *The Chemistry of Blood Coagulation.*, Charles C Thomas, Springfield, Ill.
2. Rosenberg, R. D., and Damus, P. S. (1973) *J. Biol. Chem.* 248, 6490–6505
3. Damus, P. S., Hicks, M., and Rosenberg, R. D. (.1973) *Nature* 246, 355–357
4. Marcum, J. A., McKenney, J. B., Galli, S. J., Jackman, R. W., and Rosenberg, R. D. (1986) *Am. J. Physiol.* 250, H879-H888
5. Marcum, J. A., McKenney, J. B., and Rosenberg, R. D. (1984) *Journal of Clinical Investigation* 74, 341–350
6. Marcum, J. A., Atha, D. H., Fritze, L. M. S., Nawroth, P., Stern, D., and Rosenberg, R. D. (1986) *J. Biol. Chem.* 261, 7507–7517
7. Marcum, J. A., and Rosenberg, R. D. (1985) *Biochem. Biophys. Res. Commun.* 126, 365–372
8. Kojima, T., Leone, C. W., Marchildon, G. A., Marcum, J. A., and Rosenberg, R. D. (1992) *J. Biol. Chem.* 267, 4859–4869
9. Lindahl, U., and Kjellén, L. (1987) in *The Biology of the Extracellular Matrix Proteoglycans* (Wight, T. N., and Mecham, R., eds), pp. 59–104, Academic, New York
10. Atha, D. H., Stevens, A. W., Rimon, A., and Rosenberg, R. D. (1984) *Biochemistry* 23, 5801–5812
11. Atha, D. H., Lormeau, J. C., Petitou, M., Rosenberg, R. D., and Choay, J. (1985) *Biochemistry* 24, 6723–6729
12. Atha, D. H., Lormeau, J. C., Petitou, M., Rosenberg, R. D., and Choay, J. (1987) *Biochemistry* 26, 6454–6461
13. Choay, J., Petitou, M., Lormeau, J. C., Sinaÿ, P., Casu, B., and Gatti, G. (1983) *Biochem. Biophys. Res. Commun.* 116, 492–499
14. Lindahl, U., Bäckström, G., Thunberg, L., and Leder, I. G. (1980) *Proc. Nat. Acad. ci. U.S.A.* 77, 6551–6555
15. Lindahl, U., Bäckström, G., and Thunberg, L. (1983) *J. Biol. Chem.* 258, 9826–9830
16. Rosenberg, R. D., and Lam, L. (1979) *Proc. Nat. Acad. Sci. USA.* 76, 1218–1222
17. Rosenberg, R. D., Armand, G., and Lam, L. (1978) *Proc. Nat. Acad. Sci. U.S.A.* 75, 3065–3069
18. Oosta, G. M., Gardner, W. T., Beeler, D. L., and Rosenberg, R. D. (1981) *Proc. Nat. Acad. Sci. U.S.A.* 78, 829–833
19. Stone, A. L., Beeler, D. L., Oosta, G. M., and Rosenberg, R. D. (1982) *Proc. Nat. Acad. Sci. U.S.A.* 79, 7190–7194
20. Lind, T., Lindahl, U., and Lidholt, K. (1993) *J. Biol. Chem.* 268, 20706–20708
21. Brandan, E., and Hirschberg, C. B. (1988) *J. Biol. Chem.* 263, 2417–2422
22. Pettersson, I., Kusche, M., Linger. E., Wiad, H., Nylund, L., Lindahl, U., and Kjellén, L. (1991) *J. Biol. Chem.* 266, 8044–8049
23. Campbell, P., Hannesson, H. H., Sandbäck, D., Rodén, L., Lindhal, U., and Li, J.-P. (1994) *J. Biol. Chem.* 269, 26953–26958
24. Kobayashi, M. Habuchi, H., Habuchi, O., Saito, M., and Kimata, K. (1996) *J. Biol. Chem.* 271, 7645–7653
25. Habuchi, H., Habuchi, O., and Kimata, K. (1995) *J. Biol. Chem.* 270, 4172–4179
26. Liu, J., Shworak, N. W., Fritze, L. M. S., Edelberg, J. M., and Rosenberg, R. D. (1996) *J. Biol. Chem.* 271, 27072–27082
27. Orellana, A., Hirschberg, C. B., Wei, Z., Swiedler, S. J., and Ishihara, M. (1994) *J. Biol. Chem.* 269, 2270–2276
28. Hashimoto, Y. Orellana, A., Gil, G., and Hirschberg, C. B. (1992) *J. Biol. Chem.* 267, 15744–15750
29. Eriksson, I., Sandbäck, D., Ek, B., Lindahl, U., and Kjellén, L. (1994) *J. Biol. Chem.* 269, 10438–10443
30. Ishihara, M., Guo, Y., Wei, Z., Yang, Z., Swiedler, S. J., Orellana, A., and Hirschberg, C. B. (1993) *J. Biol. Chem.* 268, 20091–20095
31. Cheung, W.-F. Eriksson, I., Kusche-Gullberg, M., Lindahl, U., and Kjellén, L. (1996) *Biochemistry* 35, 5250–5256
32. Casu, B. (1985) *Adv. Carbohydr. Chem. Biochem.* 43, 51–134
33. Shworak, N. W., Shirakawa, M., Colliec-Jouault, S., Liu, J., Mulligan, R. C., Birinyi, L. K., and Rosenberg, R. D. (1994) *J. Biol. Chem.* 269, 24941–24952
34. Colliec-Jouault, S., Shworak, N. W., Liu, J., de Agostini, A. I., and Rosenberg, R. D. (1994) *J. Biol. Chem.* 269, 24953–24958
35. Shworak, N. W., Fritze, L. M. S., Liu, J., Butler, L. D., and Rosenberg, R. D. (1996) *J. Biol. Chem.* 271, 27063–27071
36. Lam, L. H., Silbert, J. E., and Rosenberg, R. D. (1976) *Biochem. Biophys. Res. Commun.* 69, 570–577
37. Linhardt, R. J., Wang, H., Loganathan, D., and Bae, J. (1992) *J. Biol. Chem.* 267, 380–2387
38. Kusche, M., Torri, G., Casu. B., and Lindahl, U. (1990) *J. Biol. Chem.* 265, 7292–7300
39. Montgomery, R., Lidholt, K., Flay, N., Liang, J., Vertel, B., Lindahl, U., and Esko, J. (1992) *Proc. Nat. Acad. Sci. U.S.A.* 89, 11327–11331

40. Razi, N., and Lindahl, U. (1995) *J. Biol. Chem.* 270, 11267–11275
41. de Agostini, A. L., Lau, H. K., Leone, C., Youssoufian, H., and Rosenberg, R. D. (1990) *Proc. Nat. Acad Sci. U.S.A.* 4, 87, 9784–9788
42. Shworak, N. W., Shirakawa, M., Mulligan, R. C., and. Rosenberg, R. D. (1994) *J. Biol. Chem.* 269, 21204–21214
43. Fernandez, J., DeMott, M., Atherton, D., and Mische, S. M. (1992) *Anal. Biochem.* 201, 255–264
44. Stone, K. L., Elliott, J. I., Peterson, G., McMurray, W., and Williams, K. R. (1990) *Methods Enzymol.* 193, 389–412
45. Favaloro, J., Treisman, R., and Kamen, R. (1980) *Methods Enzymol.* 65, 718–749
46. Hecker, K. H., and Roux, K. H. (1996) *BioTechniques* 20, 478–485
47. Don, R. H., Cox, P. T., Wainwright, B. J., Baker, K., and Mattick, J. S. (1991) *Nucleic Acids Res.* 19, 4008
48. Lennon, G. Auffray, C., Polymeropoulo, M., and Soares, M. B. (1996) *Genomics* 33, 151–152
49. Wei, Z., Swiedler, S. J., Ishihara, M., Orellana, A., and Hirschberg, C. B. (1993) *Proc. Nat. Acad. Sci. U.S.A.* 90, 3885 –3888
50. Kojima, T., Shworak, N. W., and Rosenberg, R. D. (1992) *J. Biol. Chem.* 267, 4870–4877
51. Chomczynski, P., and Sacchi, M. (1987) *Anal. Biochem.* 162, 156–159
52. Young, J. D.-E., Liu. C.-C., Butler, G., Cohn, Z. A., and Galli, S. J. (1987) *Proc. Nat. Acad. Sci. U.S.A.* 84, 9175–9179
53. Kozak. (1989) *J. Cell Biol.* 108, 229–241
54. von Heijne, G. (1986) *Nucleic Acids Res.* 14, 4683–4690
55. Robinson, H. C., Horner, A. A., Höök, M., Ögren, S., and Lindahl, U. (1978) *J. Biol. Chem.* 253, 6687–6693
56. Andres, D. A., Rhodes, J. D., Meisel, R. L., and Dixon, J. E. (1991) *J. Biol. Chem.* 266, 14277–14282
57. Munro, S., and Pelham, H. R. (1987) *Cell* 48, 899–907
58. Weis, K., Griffiths, G., and Lamond, A. I. (1994) *J. Biol. Chem.* 269, 19142–19150
59. Scherer, P. E., Lederkremer, G. Z., Williams, S., Fogliano, M., Baldini, G., and Lodish, H. F. (1996) *J. Cell Biol.* 133, 257–268
60. Hong, W., and Tang, B. L. (1993) *BioEssays* 15, 231–238
61. Machamer, C. E. (1991) *Trends Cell Biol.* 1, 141–144
62. Weinshilboum, R. M., Otterness, D. M., Aksoy, I. A., Wood, T. C., Her, C., and Raftogianis, R. B. (1997) *FASEB J.* 11, 3–14
63. Walker, J. E., Saraste, M., Runswick, M. J., and Gay, N. J. (1982) *EMBO J.* 1, 945–951
64. Saraste, M., Sibbald, P. R., and Wittinghofen, A. (1990) *Trenids Biochem. Sci.* 15, 430–434
65. Zheng, Y., Bergold, A., and Duffel, M. W. (1994) *J. Biol. Chem.* 269, 30313–30319
66. Habuchi, O., Tsuzuki, M., Takeuchi, I., Hara, M., Matsui, Y., and Ashikari, S. (1991) *Biochim. Biophys. Acta* 1133, 9–16
67. Nishinaga, M., Ozawa, T., and Shimada, K. (1993) *J. Clin. Invest.* 92, 1381–1386
68. Wilson, R., et al. (1994) *Nature* 368, 32–38
69. Hogan, et al. (1986) *Manipulating the Mouse Embryo*, Cold Spring Harbor Laboratory Press, Cold Spring Harbor, N.Y.
70. Shworak et al. (1997) *J. Biol. Chem.* 272, 28008–28019

What is claimed is:

1. An isolated nucleic acid molecule comprising a nucleic acid sequence consisting of nucleotides 323 to 1255 of SEQ ID NO: 1, wherein said nucleic acid sequence encodes a polypeptide having 3-O-sulfotransferase activity.

2. The isolated nucleic acid molecule of claim 1, wherein said nucleic acid sequence encodes a polypeptide comprising amino acid residues 53–311 or 21–307 of SEQ ID NO: 2, and wherein said polypeptide has 3-O-sulfortransferase activity.

3. An isolated nucleic acid molecule, wherein said nucleic acid molecule comprises the nucleotide sequence in SEQ ID NO: 1.

4. An isolated nucleic acid molecule, comprising a nucleic acid sequence that has at least 90% nucleotide sequence identity with nucleotides 323–1255 of SEQ ID NO: 1, wherein said nucleic acid sequence encodes a polypeptide having 3-O-sulfotransferase activity.

5. An isolated nucleic acid molecule, wherein said nucleic acid molecule comprises the nucleotide sequence of SEQ ID NO: 3, and wherein said nucleic acid molecule encodes a polypeptide having 3-O-sulfotransferase activity.

6. An isolated nucleic acid molecule comprising a nucleic acid sequence encoding a polypeptide comprising the amino acid sequence set forth in SEQ ID NO: 2, wherein said polypeptide has 3-O-sulfotransferase activity.

7. An isolated nucleic acid molecule comprising a nucleic acid sequence encoding a polypeptide comprising amino acid residues 53–311 of SEQ ID NO: 2, wherein said polypeptide has 3-O-sulfotransferase activity.

8. An isolated nucleic acid molecule, comprising a nucleic acid sequence consisting of nucleotides 119–1039 of SEQ ID NO: 3, wherein said nucleic acid sequence encodes a polypeptide having 3-O-sulfotransferase activity.

9. The isolated nucleic acid of claim 8, wherein said nucleic acid sequence encodes a polypeptide comprising amino acid residues 21–303 or 49–307 of SEQ ID NO: 4, wherein said polypeptide has 3-O-sulfotranferase activity.

10. An isolated nucleic acid molecule, comprising a nucleic acid encoding a polypeptide comprising amino acid residues 49–307 of SEQ ID NO: 4, wherein said polypeptide has 3-O-sulfotransferase activity.

11. An isolated nucleic acid molecule comprising a nucleic acid sequence that has at least 90% nudeotide sequence identity with nucleotides 119 to 1039 of SEQ ID NO: 3, wherein said nucleic acid sequence encodes a polypeptide having 3-O-sulfotransferase activity.

12. An isolated nucleic acid molecule comprising a nucleic acid sequence that encodes a polypeptide comprising the amino acid sequence set forth in of SEQ ID NO: 4, wherein said polypeptide has 3-O-sulfotransferase activity.

13. An isolated host cell comprising a nucleic acid of claim 1, 4, 7, 8, 9 or 12.

14. The isolated host cell of claim 13, wherein said host cell is selected from the group consisting of bacterial cells, yeast cells and insect cells.

15. The isolated host cell of claim 13, wherein said cell is a mammalian cell.

16. The isolated host cell of claim 13, wherein said cell is selected from the group consisting of COS-7 cells, CHO cells, murine primary cardiac microvascular endothelial cells, murine mast cell line C57.1, human primary endothelial cells of umbilical vein, F9 embryonal carcinoma cells, rat fat pad endothelial cells, and L cells.

17. A vector comprising the isolated nucleic acid of claim 1, 4, 6, 7, 8, 9, 11 or 12.

18. An isolated host cell comprising the vector of claim 17.

* * * * *